(12) United States Patent
Kawata et al.

(10) Patent No.: US 7,153,815 B2
(45) Date of Patent: Dec. 26, 2006

(54) INSECTICIDE CONTAINING HYDRAZONE DERIVATIVE AS THE ACTIVE INGREDIENT AND NOVEL HYDRAZONE DERIVATIVE

(75) Inventors: Shinji Kawata, Machida (JP); Shuko Okui, Chuo-ku (JP); Shigeru Suzuki, Kawachinagano (JP); Toshiki Fukuchi, Kawachinagano (JP); Akiyuki Suwa, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 120 days.

(21) Appl. No.: 10/500,925

(22) PCT Filed: Jan. 10, 2003

(86) PCT No.: PCT/JP03/00152

§ 371 (c)(1),
(2), (4) Date: Jul. 27, 2004

(87) PCT Pub. No.: WO03/059064

PCT Pub. Date: Jul. 24, 2003

(65) Prior Publication Data

US 2005/0203149 A1   Sep. 15, 2005

(30) Foreign Application Priority Data

Jan. 10, 2002 (JP) ............... 2002-003830
Jul. 8, 2002 (JP) ............... 2002-198275
Sep. 9, 2002 (JP) ............... 2002-262256

(51) Int. Cl.
| | | |
|---|---|---|
| A01N 35/08 | (2006.01) | |
| A01N 43/54 | (2006.01) | |
| A01N 43/58 | (2006.01) | |
| A01N 43/40 | (2006.01) | |
| A01N 43/08 | (2006.01) | |
| A01N 43/10 | (2006.01) | |
| A01N 37/18 | (2006.01) | |
| A01N 37/20 | (2006.01) | |
| C07C 239/22 | (2006.01) | |
| C07C 239/20 | (2006.01) | |
| C07D 333/28 | (2006.01) | |
| C07D 277/10 | (2006.01) | |
| C07D 277/12 | (2006.01) | |
| C07D 213/81 | (2006.01) | |
| C07D 213/82 | (2006.01) | |
| C07D 413/12 | (2006.01) | |
| C07D 239/24 | (2006.01) | |

(52) U.S. Cl. ............ 504/344; 504/209; 504/254; 504/239; 504/294; 504/289; 504/269; 504/236; 564/148; 564/149; 549/77; 549/493; 548/161; 548/204; 548/247; 546/300; 546/312; 546/332; 546/194; 546/270.1; 544/131; 544/334; 544/409; 544/410; 544/336; 544/242; 544/332

(58) Field of Classification Search ............... 544/131, 544/334, 409, 410, 336, 242, 332; 546/300, 546/312, 330, 332, 335, 194, 270.1; 548/161, 548/204, 247; 549/77, 493; 564/148, 149
See application file for complete search history.

(56) References Cited

U.S. PATENT DOCUMENTS

| 5,304,573 A | 4/1994 | Hino et al. |
| 5,358,965 A | 10/1994 | Hino et al. |
| 5,990,171 A | 11/1999 | Seitz et al. |

FOREIGN PATENT DOCUMENTS

| JP | 05-262712 | 10/1993 |
| JP | 2001-072516 | 3/2001 |
| WO | WO 01/01781 | 1/2001 |

OTHER PUBLICATIONS

Bel'skaya et al. (Chemistry of Heterocyclic Compounds, 2001, 36(9), 1066-1076).*
Waldsheim et al. (Journal fuer Praktische Chemie/Chemiker-Zeitung 1995, 337(3), p. 222). **CAS Abstract attached.*
Larsen et al. (Journal of Organic Chemistry 1981, 46(12), p. 2465-2466.*

(Continued)

Primary Examiner—Joseph K. McKane
Assistant Examiner—Jason M. Nolan
(74) Attorney, Agent, or Firm—Oliff & Berridge, PLC

(57) ABSTRACT

A insecticide characterized by containing as active ingredient a hydrazone derivative of formula (I)

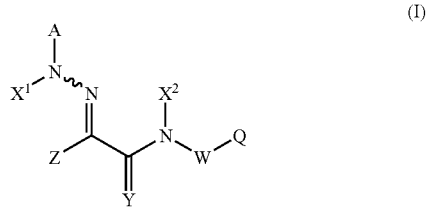

wherein A and Q are an aryl or a heterocyclic group, W is oxygen atom, an aminylene, an alkylene group, an oxyalkylene group or an alkyleneoxy, $X^1$ and $X^2$ are hydrogen atom, an alkyl, an alkenyl, an alkynyl, an aryl, a heterocyclic group, formyl, an acyl, an alkoxycarbonyl, an aryloxycarbonyl, a heterocyclic oxycarbonyl, an alkylsulfinyl, an arylsulfinyl, a heterocyclic sulfinyl, an alkylsulfonyl, an arylsulfonyl or a heterocyclic sulfonyl, Y is oxygen atom or sulfur atom, Z is hydrogen atom, a halogen atom, cyano, an alkyl, an alkenyl, an alkynyl, an amino, an alkoxy or an alkylthio, the substituents may be substituted; and novel hydrazon derivatives.

17 Claims, No Drawings

OTHER PUBLICATIONS

Abstract of M. O. Lozinskii et al., "Amides and Hydrazides of Arylazochloroacetic Acids," Zhurnal Obshchei Khimii, 1(10), pp. 1871-1875, (1965).

Abstract of M. O. Lozinskii et al., "Condensation and Cyclization of Arylazochloroacetic Acids v. Chlorides, Arylamides, and Acylhydrazides of Acylazochloroacetic Acids," Zhurnal Obshchei Khimii, 1(11), pp. 1976-1980, (1965).

Abstract of Alexander B. A. Jansen et al., "Synthesis of Methyl Benzylpenillonate," Monatshefte Fuer Chemie, 98 (3), pp. 1017-1026, (1967).

Abstract of Yasuhiro Chigira et al., "Reaction of N-(.alpha.-acetoxycinnamoyl)-N-hydroxy derivatives of DL-alanine esters. Formation of imidazolidinone and its transformations into pyrrolidinedione and oxazolidinone," Bulletin of the Chemical Society of Japan, 42(1), pp. 228-232, (1969).

Abstract of Klaus Hartke et al., "Thione and Dithioesters. XVIII. Reaction of Dithionooxalates with Phenylhydrazine," Chemiker-Zeitung, 98 (12), pp. 618-619, (1974).

Abstract of Franz Alfred Neugebauer et al., "The Structure of 'diformazyl':5-bis(phenylazo)methylene-1,3-diphenyltetrazoline betaine," Chemische Berichte, 112(7), pp. 2369-2379, (1979).

Abstract of I.M. Bazavova et al., "Study of a Series of Dithiocarbamic Acid Derivatives. VI. Methyl N-benzyldithiocarbamate in aralkylthiocarbamoylation. Reaction of the Benzylamide of Carbarnoylcyanothioacetic acid with aryldiazonium salts," Zhurnal Organicheskoi Khimii, 15(6), pp. 1213-1217, (1979).

Abstract of R. G. Dubenko et al., "Fungicidal Properties of Arylhydrazones of Glyoxylic Acid Substituted Derivatives," Fiziologicheski Aktivnye Veshchestva, 13, pp. 33-37, (1981).

Abstract of John C. Gilbert et al., "Reactions of alkylidenecarbenes derived from N,N-distributed-2-oxopropanamides: the formation of 3-pyrrol-2-ones and 2-butynamides," Journal of Organic Chemistry, 51(19), pp. 3656-3663, (1986).

Abstract of Sandor Karady, et al., "1, 2, 5-Thiadiazole 1-oxides. IV. Ring transformation to 1,2,3,5-thiatriazole and 1,2,4,6-thiatriazine 1-oxide," Tetrahedron Letters, 26(50), pp. 6155-6158, (1985).

Abstract of G. Waldheim et al., "The Coloring Constituent of the Spectrophotometric Determination of Phenylbutazone After Reaction with p-nitrophenyldiazonium Chloride," Pharmazie, 42(1), pp. 11-15, (1987).

Abstract of G. Waldeim et al., "Studies of Ring Cleavage of Some 4-(4-nitrophenylazo)-substituted pyrazolidine-3,5-dione derivatives," Journal Fuer Praktische Chemie, 332(5), pp. 783-790, (1990).

Abstract of Masato Saito et al., "Antiviral Peptides with Non-natural Amino Acids," Akita Kogyo Koto Senmon Gakko Kenkyu Kiyo, 36, pp. 40-43, (2001).

Abstract of R. Haessner et al., "Studies of the photochemical bleaching behavior of tautomeric monoazo dyes. III. Photochemical degradation of malononitrile 2- and acetylacetone 3-phenylhydrazones and their derivatives in polymer matrix," Journal Signalaufzeichnungsmaterialien, 1982, 10(5), 373-376: Chemical Abstracts, vol. 98, No. 22, May 30, 1983, p. 79.

Yoshiharu Yagi, "Absorption spectra of azo dyes and their metal complexes. V. The electronic absorption spectra of metal-complexed hydroxyphenylazoacetbenzylamides," Bull. Chem. Soc. Japan, 1963, vol. 36, No. 5, pp. 492 to 517.

* cited by examiner

INSECTICIDE CONTAINING HYDRAZONE DERIVATIVE AS THE ACTIVE INGREDIENT AND NOVEL HYDRAZONE DERIVATIVE

TECHNICAL FIELD

The present invention to insecticides containing hydrazone derivatives as active ingredient, specifically insecticides for agricultural and horticultural use, clothing, food and housing-related use, or livestock and pet use, and to novel hydrazone derivatives useful as the insecticide.

BACKGROUND ART

There are many researches for insecticides having hydrazone skeleton, and some hydrazone derivatives are put in practical use as insect pest control agents. However, they are insufficient in control effect, limited in use due to appearance of insects with resistance thereto, occur chemical injury to plants or pollution, or have a strong toxicity to man and beast, and to fishes. Therefore, there are few control agents to be satisfied. Consequently, it has been strongly demanded to overcome these defects and to provide novel agents that can be safely used.

On the other hand, it is disclosed in Japanese Patent Laid-open Nos. Hei 5-32603, Hei 5-262712 and 2001-72516 that hydrazono acetic acid amide derivatives represented by the compound indicated below have an insecticidal activity. However, they are compounds which a substituent on the nitrogen atom of the amide group is a phenyl group, and insufficient in insecticidal spectrum.

In addition, Japanese Patent Laid-open No. Hei 11-503134 discloses that hydrazono phenylacetic acid amide derivatives represented by the compound indicated below are useful as fungicides, but does not disclose at all insecticidal activity of these compounds.

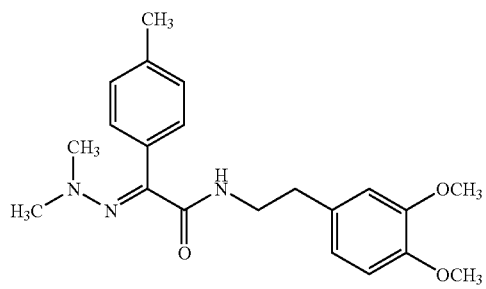

Consequently, it is demanded to successively provide insecticides having a new structure in the field of insecticides because of acquisition of resistance to insecticides. Thus, it is an object of the present invention to find compounds with a stable effect as insecticide and to find compounds with a high safety to mammals and fishes.

DISCLOSURE OF INVENTION

The present inventors have conducted extensive studies with the aim of solving the problems mentioned above to find that hydrazone derivatives having specific structure have broad insecticidal spectrum and excellent insecticidal activity, and are extremely high in safety to mammals and fishes. Based on this finding, the present invention has been accomplished.

That is, the gist of the resides in an insecticide characterized by containing as active ingredient a hydrazone derivative of formula (I)

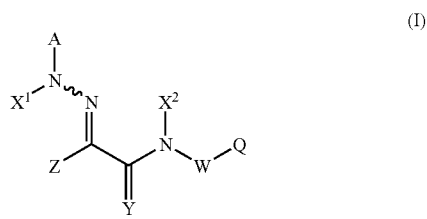

(I)

wherein A and Q independently of the other are an unsubstituted or substituted aryl, or an unsubstituted or substituted heterocyclic group, W is oxygen atom, an unsubstituted or substituted aminylene group, an unsubstituted or substituted alkylene group, an unsubstituted or substituted oxyalkylene group, or an unsubstituted or substituted alkyleneoxy, $X^1$ and $X^2$ independently of the other are hydrogen atom, an unsubstituted or substituted alkyl, an unsubstituted or substituted alkenyl, an unsubstituted or substituted alkynyl, an unsubstituted or substituted aryl, an unsubstituted or substituted heterocyclic group, formyl, an unsubstituted or substituted acyl, an unsubstituted or substituted alkoxycarbonyl, an unsubstituted or substituted aryloxycarbonyl, an unsubstituted or substituted heterocyclic oxycarbonyl, an unsubstituted or substituted alkylsulfinyl, an unsubstituted or substituted arylsulfinyl, an unsubstituted or substituted heterocyclic sulfinyl, an unsubstituted or substituted alkylsulfonyl, an unsubstituted or substituted arylsulfonyl, or an unsubstituted or substituted heterocyclic sulfonyl, Y is oxygen atom or sulfur atom, Z is hydrogen atom, a halogen atom, cyano, an unsubstituted or substituted alkyl, an unsubstituted or substituted alkenyl, an unsubstituted or substituted alkynyl, an unsubstituted or substituted amino, an unsubstituted or substituted alkoxy, or an unsubstituted or substituted alkylthio;

and a novel compound that is a hydrazone derivative of formula (II)

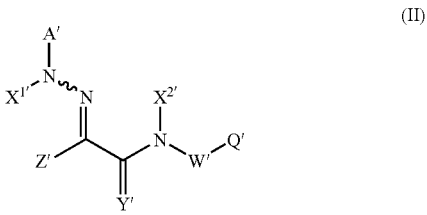

(II)

wherein A' and Q' independently of the other are an aryl or a heterocyclic group which is unsubstituted or substituted by a substituent selected from $G^5$ wherein $G^5$ is a halogen atom, hydroxy, cyano, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl, a haloalkylsulfonyl, an aryl, an aryloxy, an arylthio, a heterocyclic group, a heterocyclic oxy or a heterocyclic thio (the aryl, aryloxy, arylthio, heterocyclic group, heterocyclic oxy and heterocyclic thio are optionally substituted by a substituent selected from the group consisting of a halogen atom, hydroxy, cyano, nitro, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl), W' is oxygen atom, —$(C(R^1)(R^2))_n$—, —$O(C(R^1)(R^2))_n$—, or —$(C(R^1)(R^2))_n O$— wherein n is an integer of 1 to 5, and $R^1$ and $R^2$ independently of the other are hydrogen atom, an alkyl, an alkenyl or alkynyl, or $R^1$ and $R^2$ together form an alkylidene group, or —$N(R^3)$— wherein $R^3$ is hydrogen atom, an alkyl, an alkenyl or an alkynyl, $X^{1'}$ and $X^{2'}$ independently of the other are hydrogen atom, formyl, or an alkyl, an alkenyl, an alkynyl, an aryl, a heterocyclic group, an acyl, an alkoxycarbony, an aryloxycarbonyl, a heterocyclic oxycarbonyl, an alkylsulfinyl, an arylsulfinyl, a heterocyclic sulfinyl, an alkylsufonyl, an arylsulfonyl or a heterocyclic sulfonyl which is unsubstituted or substituted by a substituent selected from $G^2$ wherein $G^2$ is a halogen atom, hydroxy, cyano, an alkyl, a haloalkyl, an alkenyl, a haloalkenyl, an alkynyl, a haloalkynyl, an alkoxy, a haloalkoxy, an alkoxyalkoxy, formyl, an acyl, an acyloxy, an alkoxycarbonyl, an alkylthio, a haloalkylthio, an alkylsulfinyl, a haloalkylsulfinyl, an alkylsulfonyl, a haloalkylsulfonyl, an aryl, an aryloxy, an arylthio, a heterocyclic group, a heterocyclic oxy or a heterocyclic thio (the aryl, aryloxy, arylthio, heterocyclic group, heterocyclic oxy and heterocyclic thio are optionally substituted by a substituent selected from the group consisting of a halogen atom, hydroxy, cyano, an alkyl, a haloalkyl, an alkenyl, a haloalkenyl, an alkynyl, a haloalkynyl, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl), Y' is oxygen atom or sulfur atom Z' is a linear or branched alkyl, a linear or branched alkenyl, or a linear or branched alkynyl which is unsubstituted or substituted by a substituent selected from $G^6$ wherein $G^6$ is a halogen atom, an alkoxy, a haloalkoxy, an alkylthio or a haloalkylthio.

Hereinafter, the present invention will be described in detail.

The hydrazone derivatives which are active ingredients in the insecticides of the present invention are represented by the formula (I).

In the formula (I), A and Q independently of the other are an aryl such as phenyl or naphthyl; or a heterocyclic group such as tetrahydrofuranyl, furyl, thienyl, pyrrolyl, oxazolyl, oxazolinyl, isoxazolyl, isoxazolinyl, thiazolyl, thiazolinyl, isothiazolyl, isothiazolinyl, imidazolyl, imidazolinyl, pyrazolyl, pyrazolinyl, oxadiazolyl, ozadiazolinyl, thiadiazolyl, thiadizolinyl, oxadiazolonyl, pyridyl, pyrazyl, pyrimidyl, pyridazyl, triazyl, benzoxazolyl or benzothiazolyl. They may be substituted by arbitrary substituents.

Substituents on the above-mentioned A and Q are not specifically limited so long as the compound has an insecticidal activity. Concretely, they include the groups of $G^1$.

The groups of $G^1$ include a halogen atom such as fluorine atom, chlorine atom or bromine atom; hydroxy; cyano; nitro; a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl; a linear, branched or cyclic haloalkyl such as trifluoromethyl, pentafluoroethyl, difluoromethyl, trichloromethyl or dichlorodifluoroethyl; a linear, branched or cyclic alkenyl such as vinyl, propenyl, butenyl, or hexenyl; a linear, branched or cyclic haloalkenyl such as difluorovinyl or trifluorovinyl; an alkynyl such as ethynyl, butynyl or pentynyl; a haloalkynyl such as fluorobutynyl or chlorobutynyl; amino; an alkylamino such as methylamino or ethylamino: a linear or cyclic dialkylamino such as dimethylamino, diethylamino, ethylmethylamino or piperidyl; an alkoxy such as methoxy, ethoxy or n-butoxy; a haloalkoxy such as trifluoromethoxy, difluoromethoxy or trifluoroethoxy; formyl; an acyl such as acetyl, trifluoroacetyl, benzoyl or phenylacetyl; an acyloxy such as acetoxy or propanoyloxy; an alkoxycarbonyl such as methoxycarbonyl or ethoxycarbonyl; an alkylthio such as methylthio, ethylthio, n-propylthio, iso-propylthio or n-butylthio; a haloalkylthio such as trifluoromethylthio or trifluoroethylthio; an alkylsulfinyl such as methylsulfinyl, ethylsulfinyl, n-propylsulfinyl, iso-propylsulfinyl or n-butylsulfinyl; a haloalkylsulfinyl such as trifluoromethylsulfinyl or trifluoroethylsulfinyl; an alkylsulfonyl such as methylsulfonyl, ethylsulfonyl, n-propylsulfonyl, iso-propylsulfonyl or n-butylsulfonyl; a haloalkylsulfonyl such as trifluoromethylsulfonyl or trifluoroethylsulfonyl; or an aryl such as phenyl or naphthyl; an aryloxy such as phenoxy or naphthyloxy; an arylthio such as phenylthio; a heterocyclic group such as pyridyl; heterocyclic oxy such as pyridyloxy; or a heterocyclic thio such as pyridylthio.

The above-mentioned alkyl, haloalkyl, alkenyl, haloalkenyl, alkynyl, haloalkynyl, alkylamino, dialkylamino, alkoxy, haloalkoxy, alkylthio haloalkylthio, alkylsulfinyl, haloalkylsufinyl, alkylsulfonyl and haloalkylsulfonyl of $G^1$ contain preferably carbon atom of 1 to 6, and the acyl, acyloxy and alkoxycarbonyl contain preferably carbon atom of 2 to 10.

The above-mentioned aryl, aryloxy, arylthio, heterocyclic group, heterocyclic oxy and heterocyclic thio of $G^1$ may be further substituted by a substituent selected from the group consisting of a halogen atom, hydroxy, cyano, nitro, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl. Among them, the alkyl, haloalkyl, alkylamino, alkoxy, haloalkoxy, alkylthio, haloalkylthio, alkylsulfinyl, haloalkylsufinyl, alkylsulfonyl and haloalkylsulfonyl contain preferably carbon atom of 1 to 10, and the alkenyl, haloalkenyl, alkynyl, haloalkynyl, dialkylamino, acyl, acyloxy and alkoxycarbonyl contain preferably carbon atom of 2 to 10.

Further, in $G^1$ a substituent together with the adjacent substituent may form methylenedioxy, ethylenedioxy or the like, or it may form a fused ring together with the aryl or heterocyclic group of Q or A.

Among them, substituent A is preferably an unsubstituted or substituted aryl or nitrogen-containing heterocycle, more preferably an unsubstituted or substituted aryl, and particularly preferably an unsubstituted or substituted phenyl.

In A, $G^1$ which is a substituent of the aryl or heterocyclic group is preferably a halogen atom, cyano, nitro, an alkyl, a haloalkyl, an alkoxy, a haloalkoxy, alkylthio or a haloalkylthio, more preferably a halogen atom, an alkyl, a haloalkyl, an alkoxy or a haloalkoxy, further preferably a halogen atom, an alkyl, a haloalkyl or a haloalkoxy, and particularly preferably fluorine atom, a chlorine atom, bromine atom or trifluoromethyl. It is most preferable that the substituent at the 4-position on the benzene ring is trifluoromethyl. Further, one having at least a fluorine atom and trifluoromethyl is preferable.

In addition, in case where the aryl or heterocyclic group of A is substituted by a substituent selected from the above-mentioned $G^1$, the number of the substituents is preferably 1 to 3.

Q is preferably an unsubstituted or substituted phenyl or heterocyclic group, more preferably an unsubstituted or substituted nitrogen-containing heterocyclic group, particularly preferably unsubstituted or substituted pyridyl or thiazolyl.

In Q, $G^1$ which is a substituent of the aryl or heterocyclic group is preferably a halogen atom, an alkyl, a haloalkyl, an alkylamino, a dialkylamino, an alkoxy, a haloalkoxy, alkylthio and a haloalkylthio, more preferably a halogen atom, an alkyl, a haloalkyl or an alkoxy, and particularly preferably fluorine atom, a chlorine atom, bromine atom or trifluoromethyl.

In addition, in case where the aryl or heterocyclic group of Q is substituted by substituents selected from the above-mentioned $G^1$, the number of the substituents is preferably 1 to 3.

W is oxygen atom; aminylene; an alkylene such as methylene, ethylene or propylene; an oxyalkylene such as oxymethylene or oxyethylene; or an alkyleneoxy such as ethyleneoxy or propyleneoxy.

The above-mentioned aminylene, alkylene, oxyalkylene and alkyleneoxy may be arbitrarily substituted. The substituents are not specifically limited as long as the compound has an insecticidal activity. Concretely, they include for example a monovalent group of hydrocarbon.

Among them, W is preferably oxygen atom, —C($R^1$)($R^2$))$_n$—, or —N($R^3$)—.

The above-mentioned n is an integer of 1 to 5, preferably 1 to 3 and particularly preferably 1.

$R^1$ and $R^2$ independently of the other are hydrogen atom; a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl; a linear, branched or cyclic alkenyl such as vinyl, propenyl, butenyl, or hexenyl; an alkynyl such as ethynyl, butynyl or pentynyl. In addition, $R^1$ together with $R^2$ may form an alkylidene such as ethylidene or propylidene.

In addition, in case where n is 2 or more, the plural $R^1$s or $R^2$s bonded to each carbon atom may be same or different each other.

$R^3$ is hydrogen atom; a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl; a linear, branched or cyclic alkenyl such as vinyl, propenyl, butenyl or hexenyl; an alkynyl such as ethynyl, butynyl or pentynyl.

Further preferably, W is oxygen atom, —$CH_2$— or —NH—, and particularly preferably —$CH_2$— or —NH—.

$X^1$ and $X^2$ independently of the other are hydrogen atom; formyl; a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl; a linear, branched or cyclic alkenyl such as vinyl, propenyl, butenyl, or hexenyl; an alkynyl such as ethynyl, butynyl or pentynyl; an aryl such as phenyl or naphthyl; a heterocyclic group such as tetrahydrofuranyl, furyl, thienyl, pyrrolyl, oxazolyl, oxazolinyl, isoxazolyl, isoxazolinyl, thiazolyl, thiazolinyl, isothiazolyl, isothiazolinyl, imidazolyl, imidazolinyl, pyrazolyl, pyrazolinyl, oxadiazolyl, ozadiazolinyl, thiadiazolyl, thiadiazolinyl, oxadiazolonyl, pyridyl, pyrazyl, pyrimidyl, pyridazyl, triazyl, benzoxazolyl or benzothiazolyl; an acyl such as acetyl, benzoyl or phenylacetyl; an alkoxycarbonyl such as methoxycarbonyl, ethoxycarbonyl or t-butoxycarbonyl; an aryloxycarbonyl such as phenyloxycarbonyl; heterocyclic oxycarbonyl such as pyridyloxycarbonyl; an alkylsulfinyl such as methylsulfinyl, ethylsulfinyl, n-propylsulfinyl, iso-propylsulfinyl or n-butylsulfinyl; an arylsulfinyl such as phenylsulfinyl or naphthylsulfinyl; a heterocyclic sulfinyl such as pyridylsulfinyl; an alkylsulfonyl such as methylsulfonyl, ethylsulfonyl, n-propylsulfonyl, iso-propylsulfonyl or n-butylsulfonyl; an arylsulfonyl such as phenylsulfonyl or naphthylsulfonyl; a heterocyclic sulfonyl such as pyridylsulfonyl.

Among $X^1$ and $X^2$, the alkyl, alkenyl, alkynyl, aryl, heterocyclic group, acyl, alkoxycarbonyl, aryloxycarbonyl, heterocyclic oxycarbonyl, alkyksulfinyl, arylsulfinyl, heterocyclic sulfinyl, alkylsulfonyl, arylsulfonyl and heterocyclic sulfonyl may be substituted by arbitrary substituents. The substituents are not specifically limited so long as the compound has an insecticidal activity. Concretely, they include the groups of $G^2$.

The groups of $G^2$ include a halogen atom such as fluorine atom, chlorine atom or bromine atom; hydroxy; cyano; a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl; a linear, branched or cyclic haloalkyl such sd trifluoromethyl, pentafluoroethyl, difluoromethyl, trichloromethyl or dichlorodifluoroethyl; a linear, branched or cyclic alkenyl such as vinyl, propenyl, butenyl or hexenyl; a linear, branched or cyclic haloalkenyl such as difluorovinyl or trifluorovinyl; an alkynyl such as ethynyl, butynyl or pentynyl; a haloalkynyl such as fluorobutynyl or chlorobutynyl; an alkoxy such as methoxy, ethoxy, iso-propoxy, iso-butoxy or n-butoxy; a haloalkoxy such as trifluoromethoxy, difluoromethoxy or trifluoroethoxy; alkoxyalkoxy such as methoxyethoxy; formyl; an acyl such as acetyl, trifluoroacetyl, benzoyl or phenylacetyl; an acyloxy such as acetoxy or propanoyloxy; an alkoxycarbonyl such as methoxycarbonyl, ethoxycarbonyl or t-butoxycarbonyl; an alkylthio such as methylthio, ethylthio, n-propylthio, iso-propylthio or n-butylthio; a haloalkylthio such as trifluoromethylthio or trifluoroethylthio; an alkylsulfinyl such as methylsulfinyl, ethylsulfinyl, n-propylsulfinyl, iso-propylsulfinyl or n-butylsulfinyl; a haloalkylsulfinyl such as trifluoromethylsulfinyl or trifluoroethylsulfinyl; an alkylsulfonyl such as methylsulfonyl, ethylsulfonyl, n-propylsulfonyl, iso-propylsulfonyl or n-butylsulfonyl; a haloalkylsulfonyl such as trifluoromethylsulfonyl or trifluoroethylsulfonyl; or an aryl such as phenyl or naphthyl; an aryloxy such as phenoxy or naphthyloxy; an arylthio such as phenylthio; a heterocyclic group such as pyridyl; heterocyclic oxy such as pyridyloxy; or a heterocyclic thio such as pyridylthio.

The above-mentioned alkyl, haloalkyl, alkenyl, haloalkenyl, alkynyl, haloalkynyl, alkoxy, haloalkoxy, alkoxyalkoxy, alkylthio, haloalkylthio, alkylsulfinyl, haloalkylsufinyl, alkylsulfonyl and haloalkylsulfonyl of $G^2$ contain preferably carbon atom of 1 to 6, and the acyl, acyloxy and alkoxycarbonyl contain preferably carbon atom of 2 to 10.

The above-mentioned aryl, aryloxy, arylthio, heterocyclic group, heterocyclic oxy and heterocyclic thio of $G^2$ may be further substituted by a substituent selected from the group consisting of a halogen atom, hydroxy, cyano, an alkyl, a haloalkyl, an alkenyl, a haloalkenyl, an alkynyl, a haloalkynyl, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl. Among them, the alkyl, haloalkyl, alkoxy, haloalkoxy, alkylthio, haloalkylthio, alkylsulfinyl, haloalkylsufinyl, alkylsulfonyl and haloalkylsulfonyl contain preferably carbon atom of 1 to 10, and the alkenyl, haloalkenyl, alkynyl, haloalkynyl, acyl, acyloxy and alkoxycarbonyl contain preferably carbon atom of 2 to 10.

$X^1$ is preferably hydrogen atom, an alkenyl having 1 to 4 carbon atoms, an acyl having 1 to 10 carbon atoms, or an alkyl having 1 to 10 carbon atoms which is unsubstituted or substituted by a substituent selected from the group consisting of a halogen atom, cyano, an alkoxy, an alkylthio, an alkoxycarbonyl and an unsubstituted or substituted aryl, and more preferably hydrogen atom, an alkenyl having 1 to 4 carbon atoms or an alkyl having 1 to 4 carbon atoms.

$X^2$ is preferably hydrogen atom, an alkyl or an alkoxycarbonyl, more preferably hydrogen atom or an alkyl having 1 to 4 carbon atom, and particularly preferably hydrogen atom.

Y is oxygen atom or sulfur atom, and preferably oxygen atom.

Z is hydrogen atom; a halogen atom such as fluorine atom, chlorine atom or bromine atom; cyano; a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl; a linear, branched or cyclic alkenyl such as vinyl, propenyl, butenyl or hexenyl; an alkynyl such as ethynyl, butynyl or pentynyl; amino; an alkoxy such as methoxy, ethoxy, iso-butoxy or n-butoxy; an alkylthio such as methylthio, ethylthio, n-propylthio, iso-propylthio or n-butylthio.

The alkyl, alkenyl, alkynyl, alkoxy and alkylthio of the above-mentioned Z are preferably ones having carbon atoms of 6 or less. The alkyl, alkenyl, alkynyl, amino, alkoxy and alkylthio of the above-mentioned Z may be arbitrarily substituted. The substituents are not specifically limited as long as the compound has an insecticidal activity. Concretely, the substituents of the alkyl, alkenyl, alkynyl, alkoxy and alkylthio include the groups of $G^3$, and the substituents of the amino include the groups of $G^4$.

The groups of $G^3$ include a halogen atom such as fluorine atom, chlorine atom or bromine atom; hydroxy; cyano; nitro; a haloalkyl such as trifluoromethyl, pentafluoroethyl, difluoromethyl, trichloromethyl or dichlorodifluoroethyl; a linear, branched or cyclic alkenyl such as vinyl, propenyl, butenyl or hexenyl; a linear, branched or cyclic haloalkenyl such as difluorovinyl or trifluorovinyl; an alkynyl such as ethynyl, butynyl or pentynyl; a haloalkynyl such as fluorobutynyl or chlorobutynyl; an alkoxy such as methoxy, ethoxy, iso-propoxy, iso-butoxy or n-butoxy; a haloalkoxy such as trifluoromethoxy, difluoromethoxy or trifluoroethoxy; an alkylthio such as methylthio, ethylthio, n-propylthio, iso-propylthio or n-butylthio; or a haloalkylthio such as trifluoromethylthio or trifluoroethylthio.

The alkyl, haloalkyl, alkenyl, haloalkenyl, alkynyl, haloalkynyl, alkoxy, haloalkoxy, alkylthio and haloalkylthio of $G^3$ include preferably carbon atoms of 3 or less.

The groups of $G^4$ include hydroxy; cyano; a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl; a linear, branched or cyclic haloalkyl such as trifluoromethyl, pentafluoroethyl, difluoromethyl, trichloromethyl or dichlorodifluoroethyl; a linear, branched or cyclic alkenyl such as vinyl, propenyl, butenyl or hexenyl; a linear, branched or cyclic haloalkenyl such as difluorovinyl or trifluorovinyl; an alkynyl such as ethynyl, butynyl or pentynyl; a haloalkynyl such as fluorobutynyl or chlorobutynyl; an alkoxy such as methoxy, ethoxy, is-propoxy, iso-butoxy or n-butoxy; or a haloalkoxy such as trifluoromethoxy, difluoromethoxy or trifluoroethoxy.

The alkyl, haloalkyl, alkenyl, haloalkenyl, alkynyl, haloalkynyl, alkoxy and haloalkoxy of $G^4$ include preferably carbon atoms of 3 or less.

In addition, in case where the above-mentioned amino is substituted by two substituents selected from $G^4$, the $G^4$s may be same or different each other, and further two $G^4$s together form a ring such as pyrrolidinyl, piperidyl, piperadinyl or morphoryl.

Z is preferably hydrogen atom, cyano, an amino unsubstituted or substituted by one or two alkyl groups having 1 to 4 carbon atoms, or an alkyl unsubstituted or substituted by a substituent selected from the group consisting of a halogen atom, an alkoxy and an alkylthio, more preferably a halogen atom, an alkyl, cyano or amino, further preferably an alkyl or cyano, and particularly preferably methyl or ethyl.

Although the hydrazone derivatives of the formula (I) have geometrical isomers (E/Z) based on the double bond C=N, both ingredients are effective and can be used as the insecticide of the present invention. Preferably, the E form is effective as the insecticide of the present invention.

The hydrazone derivatives of the formula (I) have generally a molecular weight of 1000 or less, and more preferably a molecular weight of 750 or less.

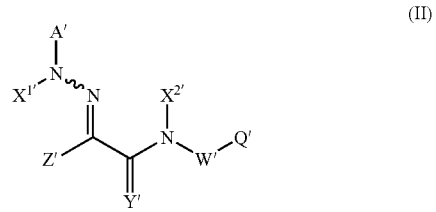

(II)

Further, the compounds of the formula (II) are a group of particularly preferable novel compounds among the hydrazone derivatives used as the insecticides of the present invention.

The aryl and heterocyclic group unsubstituted or substituted by a substituent selected from $G^5$ which are A' and Q' in the formula (II) include groups similar to ones exemplified for A and Q in the formula (I).

$G^5$ is a halogen atom, hydroxy, cyano, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl, a haloalkylsulfonyl, an aryl, an aryloxy, an arylthio, a heterocyclic group, a heterocyclic oxy or a heterocyclic thio, and the aryl, aryloxy arylthio, heterocyclic group, heterocyclic oxy and heterocyclic thio are optionally substituted by a halogen atom, hydroxy, cyano, nitro, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl or a haloalkylsulfonyl.

The halogen atom, alkyl, haloalkyl, alkenyl, haloalkenyl, alkynyl, haloalkynyl, amino, alkylamino, dialkylamino, alkoxy, haloalkoxy, acyl, acyloxy, alkoxycarbonyl, alkylthio, haloalkylthio, alkylsulfinyl, haloalkylsulfinyl, alkylsulfonyl, haloalkylsulfonyl, aryl, aryloxy, arylthio, heterocyclic group, heterocyclic oxy and heterocyclic thio that are substituent $G^5$, include groups similar to ones exemplified for $G^1$ in the formula (I).

The A' is preferably phenyl or a nitrogen-containing heterocyclic group unsubstituted or substituted by a substituent selected from the group consisting of a halogen atom, an alkyl, a haloalkyl, an alkoxy, a haloalkoxy, an alkylthio and a haloalkylthio, more preferably phenyl unsubstituted or substituted by a substituent selected from the group consisting of a halogen atom, an alkyl, a haloalkyl and a haloalkoxy.

The Q' is preferably an aryl or a heterocyclic group unsubstituted or substituted by a substituent selected from the group consisting of a halogen atom, an alkyl, a haloalkyl, an alkylamino, a dialkylamino, an alkoxy, a haloalkoxy; an alkylthio and a haloalkylthio, more preferably a heterocyclic group unsubstituted or substituted by a substituent selected from the group consisting of a halogen atom, an alkyl and a haloalkyl.

W' is oxygen atom, —$(C(R^1)(R^2))_n$—, —$O(C(R^1)(R^2))_n$—, or —$(C(R^1)(R^2))_nO$— wherein n is an integer of 1 to 5, and $R^1$ and $R^2$ independently of the other are hydrogen atom, an alkyl, an alkenyl or alkynyl, or $R^1$ and $R^2$ together form an alkylidene group, or —$N(R^3)$— wherein $R^3$ is hydrogen atom, an alkyl, an alkenyl or an alkynyl.

The groups —$(C(R^1)(R^2))_n$—, —$O(C(R^1)(R^2))_n$—, —$(C(R^1)(R^2))_nO$— and —$N(R^3)$— in the W' include groups similar to ones exemplified for W in the formula (I).

The W' is preferably oxygen atom, —$(C(R^1)(R^2))_n$—, —$(C(R^1)(R^2))_nO$— or —$N(R^3)$—, more preferably oxygen atom, —$CH_2$— or —NH— and particularly preferably —$CH_2$— or —NH—.

$X^{1'}$ and $X^{2'}$ independently of the other are hydrogen atom, formyl, or an alkyl, an alkenyl, an alkynyl, an aryl, a heterocyclic group, an acyl, an alkoxycarbony, an aryloxycarbonyl, a heterocyclic oxycarbonyl, an alkylsulfinyl, an arylsulfinyl, a heterocyclic sulfinyl, an alkylsulfonyl, an arylsulfonyl or a heterocyclic sulfonyl which is unsubstituted or substituted by a substituent selected from $G^2$.

The alkyl, alkenyl, alkynyl, aryl, heterocyclic group, acyl, alkoxycarbony, aryloxycarbonyl, heterocyclic oxycarbonyl, alkylsulfinyl, arylsulfinyl, heterocyclic sulfinyl, alkylsulfonyl, arylsulfonyl or heterocyclic sulfonyl which is unsubstituted or substituted by a substituent selected from $G^2$ in the $X^{1'}$ and $X^{2'}$, include groups similar to ones exemplified for $X^1$ and $X^2$ in the formula (I).

Further, the substituent $G^2$ also include groups similar to ones exemplified in the formula (I).

The $X^{1'}$ is preferably hydrogen atom, an alkenyl having 1 to 4 carbon atoms, an acyl having 1 to 10 carbon atoms, or an alkyl having 1 to 10 carbon atoms which is unsubstituted or substituted by a substituent selected from the group consisting of a halogen atom, cyano, an alkoxy, an alkylthio, an alkoxycarbonyl and an unsubstituted or substituted aryl, and $X^{2'}$ is preferably hydrogen atom, an alkyl or an alkoxycarbonyl.

Y' is oxygen atom or sulfur atom, and preferably oxygen atom.

Z' is a linear or branched alkyl such as methyl, ethyl, n-propyl, iso-propyl, n-butyl, sec-butyl, t-butyl, n-pentyl or n-hexyl; a linear or branched alkenyl such as vinyl, propenyl, butenyl or hexenyl; or a linear or branched alkynyl such as ethynyl, butynyl or pentynyl, and the alkyl, alkenyl and alkynyl may be substituted by a substituent selected from $G^6$.

The alkyl, alkenyl and alkynyl of the above-mentioned Z' are preferably ones having carbon atoms of 6 or less.

The groups of $G^6$ include a halogen atom such as fluorine atom, chlorine atom or bromine atom; an alkoxy such as methoxy, ethoxy, iso-propoxy, iso-butoxy or n-butoxy; a haloalkoxy such as trifluoromethoxy, difluoromethoxy or trifluoroethoxy; an alkylthio such as methylthio, ethylthio, n-propylthio, iso-propylthio or n-butylthio; or a haloalkylthio such as trifluoromethylthio or trifluoroethylthio. The alkoxy, haloalkoxy, alkylthio and haloalkylthio of $G^6$ include preferably carbon atoms of 1 to 3.

Z' is preferably a linear or branched alkyl unsubstituted or substituted by a substituent selected from the group consisting of a halogen atom, an alkoxy and an alkylthio, more preferably a linear or branched alkyl, and particularly preferably methyl or ethyl.

Although the hydrazone derivatives of the formula (II) have geometrical isomers (E/Z) based on the double bond C=N, both ingredients are effective and can be used as the insecticide of the present invention. Preferably, the E form is effective as the insecticide of the present invention.

The hydrazone derivatives of the formula (I) have generally a molecular weight of 1000 or less, and more preferably a molecular weight of 750 or less.

The compounds of the formulae (I) and (II) that can be used as the insecticide of the present invention can be produced by a combination of the known reactions. For example, the production processes indicated in Schemes 1–7 described below can efficiently afford the compounds.

In the schemes described below, L is a leaving group, for example a halogen atom such as chlorine atom, bromine atom or iodine atom; an alkylsulfonyloxy such as methanesulfonyloxy or ethanesulfonyloxy; a haloalkylsulfonyloxy such as trifluoromethylsulfonyloxy or chloromethylsulfonyloxy; or an arylsulfonyloxy such as benzenesulfonyloxy or p-toluenesulfonyloxy, and preferably chlorine atom, bromine atom, methanesulfonyloxy, p-toluenesulfonyloxy or trifluoromethylsulfonyloxy.

$L^1$ is a halogen atom such as chlorine atom, bromine atom or iodine atom, and preferably chlorine atom.

R is a linear, branched or cyclic alkyl such as methyl, ethyl, n-propyl, iso-propyl, n-butyl, sec-butyl, t-butyl, n-pentyl, n-hexyl, cyclopropyl, cyclobutyl, cyclopentyl or cyclohexyl.

A, Q, W, $X^1$, $X^2$, Z and $G^4$ are the same groups as ones defined for the above-mentioned formula (I).

Scheme 1

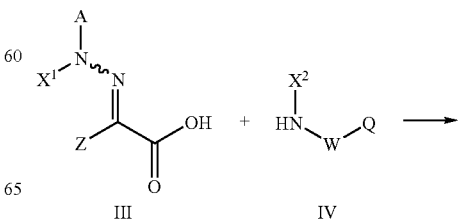

-continued

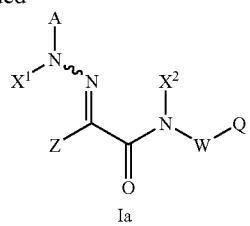

Ia

The hydrazone derivative of formula (Ia) is obtained by reacting carboxylic acid derivative (III) with amine derivative or hydrazine derivative (IV) in the presence of a condensation agent as indicated in Scheme 1.

The amount of amine derivative or hydrazine derivative (IV) used is generally 0.7 to 1.5 equivalent to the carboxylic acid derivative (III). In addition, the reaction temperature is 0 to 150° C. and preferably 10 to 100° C.

The condensation agent used is not specifically limited if it is a condensation agent generally used for a condensation reaction of a carboxylic acid with an amine, and concretely include a carbodiimide condensation agent such as dicyclohexylcarbodiimide (DCC) or 1-ethyl-3-(3-dimethylaminopropyl)carbodiimide hydrochloride (EDC.HCl); a dehydration condensation agent such as carbonyldiimidazole (CDI), BOP-Cl, HATU or diphenylphosphoryl azide (DPPA); sulfonylchloride such as methane sulfonylchloride or p-toluene sulfonylchloride; a halogenation agent such as thionyl chloride or oxazaryl chloride; acid chloride such as 2,4,6-trichlorobenzoyl chloride, pivalic acid chloride, isobutyloxycarbonyl chloride or ethyl chloroformate.

The amount of the condensation agent used is generally 0.5 to 10 times, preferably 1 to 3 times that of carboxylic acid derivative (III).

In addition, if necessary, an alkaline metal alkoxide such as sodium methoxide; an alkaline metal carbonate such as potassium carbonate; an alkaline metal carboxylate such as sodium acetate; an alkaline metal hydroxide such as potassium hydroxide; a tertiary amine such as N-methylmorpholine or triethylamine; an aromatic base such as pyridine or picoline may be added in an amount 0.01 to 1 time that of the condensation agent.

Further, if necessary, 1-hydroxybenzotriazole; N-hydroxysuccinimide; pentafluorophenol; a sulfonic acid such as methanesulfonic acid, p-toluenesulfonic acid or camfor sulfonic acid may be added in an amount 0.01 to 1 time that of the condensation agent.

The reaction is carried out by optionally using solvents. The solvent used is selected depending on reagents used, and includes for example aromatic hydrocarbons such as benzene, toluene or xylene; halogenated hydrocarbons such as dichloromethane, chloroform or 1,2-dichloroethane; ethers such as diethyl ether, tetrahydrofuran or dioxane; esters such as ethyl acetate; alcohols such as methanol, ethanol or propanol; ketones such as acetone or methyl ethyl ketone; aprotic polar solvents such as N,N-dimethylformamide, N-methylpyrrolidone, dimethylsulfoxide or acetonitrile; or water, which is used as a single solvent or a mixed solvent. Among them, toluene, dichloromethane or N,N-dimethylformamide is preferable.

The amount of the solvent used is generally 1 to 100 times by weight, preferably 4 to 40 times by weight of that carboxylic acid derivative (III).

Scheme 2

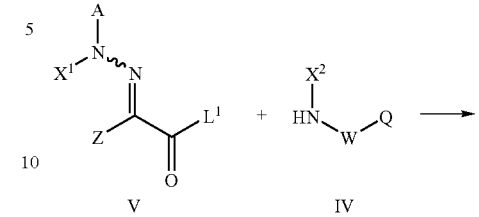

V    IV

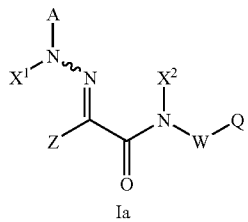

Ia

The hydrazone derivative of formula (Ia) is obtained by reacting carboxylic acid halide derivative (V) with amine derivative or hydrazine derivative (IV) in the presence of a base as indicated in Scheme 2.

The amount of amine derivative or hydrazine derivative (IV) used is generally 0.7 to 1.5 equivalent to the carboxylic acid halide derivative (V). In addition, the reaction temperature is 0 to 150° C. and preferably 10 to 100° C.

Examples of the base used include an alkaline metal alkoxide such as sodium methoxide; an alkaline metal carbonate such as potassium carbonate; an alkaline metal carboxylate such as sodium acetate; an alkaline metal hydroxide such as potassium hydroxide; a tertiary amine such as N-methylmorpholine or triethylamine; and an aromatic base such as pyridine or picoline.

The amount of the base used is generally 0.5 to 10 times, preferably 1 to 3 times that of carboxylic acid halide derivative (V) or amine derivative or hydrazine derivative (IV).

The reaction is carried out by optionally using solvents. The solvent used includes for example aromatic hydrocarbons such as benzene, toluene or xylene; halogenated hydrocarbons such as dichloromethane, chloroform or 1,2-dichloroethane; ethers such as diethyl ether, tetrahydrofuran or dioxane; esters such as ethyl acetate; ketones such as acetone or methyl ethyl ketone; aprotic polar solvents such as N,N-dimethylformamide, N-methylpyrrolidone, dimethylsulfoxide or acetonitrile; or water, which is used as a single solvent or a mixed solvent. Among them, toluene or dichloromethane is preferable.

The amount of the solvent used is generally 1 to 100 times by weight, preferably 4 to 40 times by weight of that carboxylic acid halide derivative (V).

Scheme 3

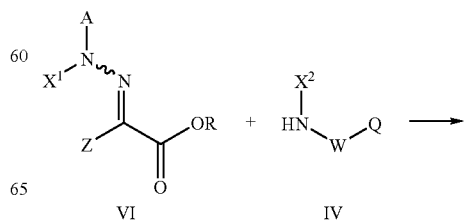

VI    IV

-continued

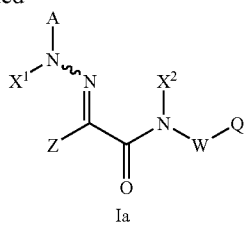

Ia

The hydrazone derivative of formula (Ia) is obtained by reacting carboxylic acid ester derivative (VI) with amine derivative or hydrazine derivative (IV) as indicated in Scheme 3.

The amount of amine derivative or hydrazine derivative (IV) used is generally 0.7 to 1.5 equivalent to the carboxylic acid ester derivative (VI). In addition, the reaction temperature is 0° C. to a boiling point of the solvent used and preferably 10 to 150° C.

The reaction is optionally carried out by using solvents, for example aromatic hydrocarbons such as benzene, toluene or xylene; halogenated hydrocarbons such as dichloromethane, chloroform or 1,2-dichlroethane; ethers such as diethyl ether, tetrahydrofuran or dioxane; alcohols such as methanol, ethanol or propanol; aprotic polar solvents such as N,N-dimethylformamide, N-methylpyrrolidone, dimethylsulfoxide or acetonitrile; or water, which is used as a single solvent or a mixed solvent. Among them, aromatic hydrocarbon solvents such as toluene or xylene are preferable.

The amount of the solvent used is generally 1 to 100 times by weight, preferably 4 to 40 times by weight of that carboxylic acid ester derivative (VI).

Scheme 4

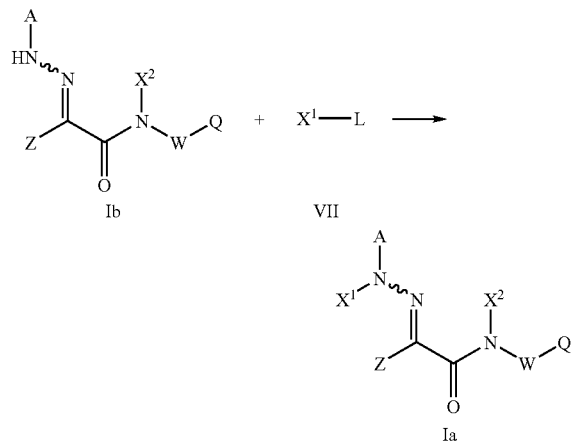

The hydrazone derivative of formula (Ia) is obtained by reacting hydrazone derivative (Ib) with halogen derivative or sulfonate derivative (VII) in the presence of a base as indicated in Scheme 4.

The amount of halogen derivative or sulfonate derivative (VII) used in the reaction is generally 0.5 to 10 times equivalent to that of the chydrazone derivative (Ib). In addition, the reaction temperature is −70 to 150° C. and preferably −20 to 100° C.

Examples of the base used include an alkyl lithium reagent such as butyl lithium; an alkaline metal hydride such as sodium hydride; an alkaline metal alkoxide such as sodium methoxide; and an alkaline metal carbonate such as sodium carbonate;.

The amount of the base used is generally 0.5 to 10 times equivalent, preferably 1 to 3 times equivalent to that of hydrazone derivative (Ib).

In addition, if necessary, a catalyst for example quaternary ammonium salt such as tetra-n-butyl ammonium bromide, or crown ether such as 18-crown-6-ether may be added in an amount of 0.01 to 1 time equivalent to that of hydrazone derivative (Ib).

The reaction is carried out by optionally using solvents. The solvent used includes for example aromatic hydrocarbons such as benzene, toluene or xylene; halogenated hydrocarbons such as dichloromethane, chloroform or 1,2-dichlroethane; ethers such as diethyl ether, tetrahydrofuran or dioxane; or aprotic polar solvents such as N,N-dimethylformamide, N-methylpyrrolidone, dimethylsulfoxide or acetonitrile, which is used as a single solvent or a mixed solvent. Among them, a polar solvent such as N,N-dimethylformamide or tetrahydrofuran is preferable.

The amount of the solvent used is generally 1 to 100 times by weight, preferably 4 to 40 times by weight of that compound (Ib).

Scheme 5

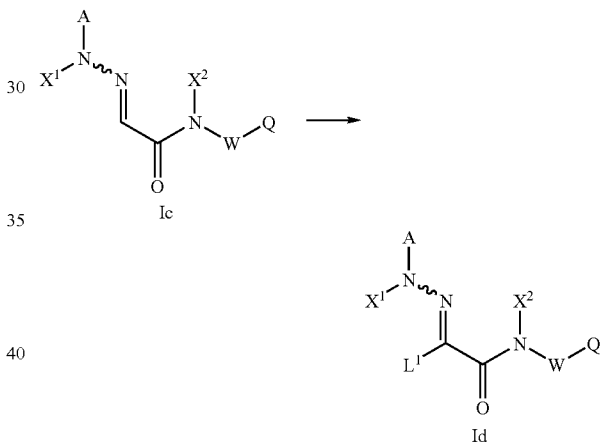

The hydrazone derivative of formula (Id) is obtained by halogenating hydrazone derivative (Ic) with a halogenation agent generally at a reaction temperature of 0 to 150° C., preferably 0 to 80° C. as indicated in Scheme 5.

Examples of the halogenation agent used include chlorine, bromine, N-chlorosuccinic acid imide, N-bromosuccinic imide and sulfuryl chloride.

The amount of the halogenation agent is generally 0.5 to 10 times equivalent, preferably 1 to 3 times equivalent to that of the hydrazone derivative (Ic).

The reaction is carried out by optionally using solvents. The solvent used includes for example aromatic hydrocarbons such as benzene, toluene or xylene; halogenated hydrocarbons such as dichloromethane, chloroform or 1,2-dichlroethane; ethers such as diethyl ether, tetrahydrofuran or dioxane; esters such as ethyl acetate; alcohols such as methanol, ethanol or propanol; ketones such as acetone or methyl ethyl ketone; aprotic polar solvents such as N,N-dimethylformamide, N-methylpyrrolidone, dimethylsulfoxide or acetonitrile; or water, which is used as a single solvent or a mixed solvent. Among them, N,N-dimethylformamide, tetrahydrofuran or toluene is preferable.

The amount of the solvent used is generally 1 to 100 times by weight, preferably 4 to 40 times by weight of that compound (Ib).

Scheme 6

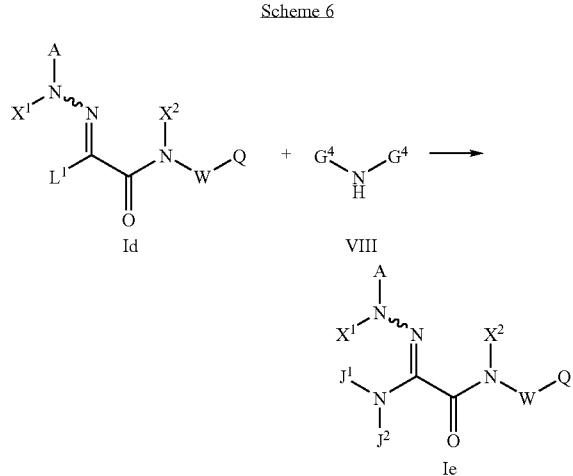

The amidine derivative of formula (Ie) is obtained by reacting hydrazone derivative (Id) with amine derivative (VIII) in the presence of a base generally at a reaction temperature of 0 to 150° C., preferably 10° C. to a boiling point of the solvent used as indicated in Scheme 6.

The amount of amine derivative (VIII) is generally 0.5 to 10 times equivalent, preferably 1 to 3 times equivalent to that of the hydrazone derivative (Id).

Examples of the base used include an alkaline metal hydride such as sodium hydride; an alkaline metal alkoxide such as sodium methoxide; an alkaline metal carbonate such as potassium carbonate; an alkaline metal carboxylate such as sodium acetate; an alkaline metal hydroxide such as potassium hydroxide; a tertiary amine such as N-methyl-morpholine or triethylamine; an aromatic base such as pyridine or picoline.

The amount of the base used is generally 0.5 to 10 times equivalent, preferably 1 to 3 times equivalent to that of the hydrazone derivative (Id).

In addition, if necessary, a catalyst for example quaternary ammonium salt such as tetra-n-butyl ammonium bromide, or crown ether such as 18-crown-6-ether may be added in an amount of 0.01 to 1 time equivalent to that of hydrazone derivative (Ib) to the reaction system.

Examples of the solvent used include for example aromatic hydrocarbons such as benzene, toluene or xylene; halogenated hydrocarbons such as dichloromethane, chloroform or 1,2-dichlroethane; ethers such as diethyl ether, tetrahydrofuran or dioxane; esters such as ethyl acetate; alcohols such as methanol, ethanol or propanol; aprotic polar solvents such as N,N-dimethylformamide, N-methylpyrrolidone, dimethylsulfoxide or acetonitrile; or a protic polar solvent such as water or acetic acid, which is used as a single solvent or a mixed solvent. Among them, ethers such as dietheylether, tetrahydrofuran or dioxane are preferable.

The amount of the solvent used is generally 1 to 100 times, preferably 4 to 40 times by weight of that compound (Id).

Scheme 7

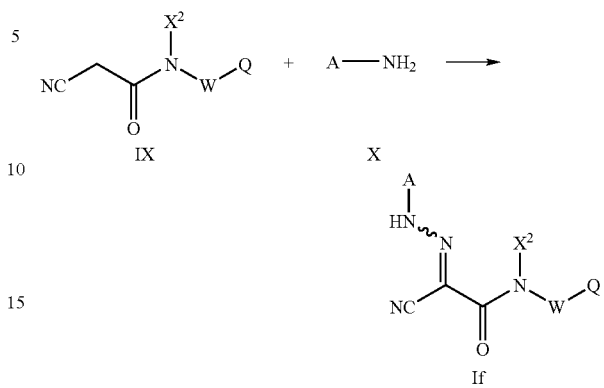

The hydrazone derivative of formula (If) is obtained by reacting diazonium salt derivative prepared by subjecting aniline derivative or heterocyclic amine (X) to diazotization with cyanoacetic acid amide (IX) in the presence of a base at a reaction temperature of 0 to 100° C., preferably 10° C. to a boiling point of the solvent used as indicated in Scheme 7.

Diazotization agents used for the diazotization of the aniline derivative or heterocyclic amine are not specifically limited if it is a diazotization agent that is generally used, and concretely include a metal nitrite such as sodium nitrite; and a nitrite such as isoamyl nitrite.

The amount of the diazotization agent is generally 0.5 to 10 times equivalent, preferably 1 to 3 times equivalent to that of the aniline derivative or heterocyclic amine (X).

The diazotization is generally carried out in the presence of an acid at a reaction temperature of −70 to 100° C., preferably −50 to 20° C.

Acids used are not specifically limited if it is an acid generally used in diazotization, and concretely include hydrochloric acid; sulfuric acid; sulfonic acid such as methanesulfonic acid or p-toluene sulfonic acid; carboxylic acid such as acetic acid or trifluoro acetic acid; Lewis acid such as boron trifluoride ether complex, and preferably hydrochloric acid, sulfuric acid or acetic acid.

The amount of the acid is generally 0.5 to 100 times equivalent, preferably 1 to 50 times equivalent to that of the aniline derivative or heterocyclic amine (X).

Examples of the base used for the reaction between diazonium salt derivative and cyanoacetic acid amide derivative (IX) are not specifically limited if it is a base generally used for coupling between diazonium salt and cyanoacetic acid derivative, and include an alkaline metal hydride such as sodium hydride; an alkaline metal alkoxide such as sodium methoxide; an alkaline metal carbonate such as potassium carbonate or sodium carbonate; an alkaline metal carboxylate such as sodium acetate; an alkaline metal hydroxide such as potassium hydroxide; a tertiary amine such as N-methylmorpholine or triethylamine; an aromatic base such as pyridine or picoline.

The amount of the base is generally 0.5 to 100 times equivalent, preferably 1 to 20 times equivalent to that of the cyanoacetic amide derivative (IX).

The reaction is generally carried out in the presence of solvent. Examples of the solvent used include for example aromatic hydrocarbons such as benzene, toluene or xylene; halogenated hydrocarbons such as dichloromethane, chloroform or 1,2-dichlroethane; esters such as ethyl acetate; alcohols such as methanol, ethanol or propanol; ketones such as acetone or methyl ethyl ketone; aprotic polar solvents such as N,N-dimethylformamide, N-methylpyrrolidone, dimethylsulfoxide or acetonitrile; or a protic polar solvent such as water or acetic acid, which is used as a single solvent or a mixed solvent. Among them, water, acetic acid and alcohols such as methanol, ethanol or propanol are preferable, and they may be mixed in an arbitrary proportion.

The amount of the solvent used is generally 1 to 100 times, preferably 4 to 40 times by weight of that compound (IX) or compound (X).

The insecticide containing the compound of the present invention as active ingredient has a control effect against insects or other pests, and is effective for repelling, exterminating or controlling pests in a wide range of scenes, such as agriculture, forestry, livestock industry, fishery and conservation scene of products in these industries, or public hygiene.

In particular, the compound of the present invention exerts an excellent effect in repellent, extermination and control of pests causing harm in agriculture or forestry, concretely in cultivation of agricultural crops or to harvest, trees or ornamental plants, etc., or pests in public hygiene scene.

Hereinafter, concrete application scenes, targeted pests, application method and the like are described, but the present invention is not limited thereto. Further, pests concretely exemplified are not limited as targeted pests, and the exemplified pests include adults, larvae, eggs and the like.

(A) Agriculture or Forestry Scene

The compounds of the present invention are effective for repellent or control of pests such as arthropods, molluscs or nematodes, or several fungi, particularly arthropods such as insects, which cause harm to agricultural crops such as food crops (rice, wheat, barley, rye or oats, corn, potato, sweet potato, leguminous plants, etc.), vegetables (rapes, cucumbers, egg plant, tomato, spring onions, etc.), fruit trees (oranges, apple, grape, peach, etc.), industrial crops (tobacco, tea, sugar beet, sugarcane, cotton, olive, etc.), forage crops and grasses (sorghums, gramineous forage grasses, leguminous forage grasses, etc.) or ornamental plants (herbaceous plants, flowers and ornamental plants, garden plants, etc) in the culturing scene thereof. In addition, the compounds of the present invention are effective also for repellent or extermination of pests in storage of harvests from the above-mentioned crops, such as cereals, fruits, nuts, spices or tobacco, or storage of the products prepared by subjecting the harvests to a process such as drying, disintegration or the like. Further, the compounds are effective for protecting standing trees, fallen trees, modified woods, stored woods or the like from harm by pests such as termites or beetles.

For example, concrete pests include the followings belonging to the phylum Arthropoda, Mollusca or Nematoda. The followings can be exemplified as pests belonging to the class Insecta in the phylum Arthropoda.

Pests of the order Lepidoptera include for example
the family Noctuidae such as common cutworm (*Spodoptera litura*), corn earworm (*Helicoverpa assulta*), cabbage armyworm (*Mamestra brassicae*) or beet semi-looper (*Plusia nigrisigna*);
the family Yponomeutidae such as diamondback (*Plutella xylostella*);
the family Tortricidae such as smaller tea tortrix (*Adoxophyes* sp.) or oriental fruit moth (*Grapholita molesta*);
the family Psychidae such as mulberry bagworm (*Canephora asiatica*),
the family Lyonetiidae such as *Lyonetia prunifoliella malinella;*
the family Gracillariidae such as apple leafminer (*Phyllonorycter ringoneela*);
the family Acrolepiidae such as allium leafminer (*Acrolepiopsis sapporensis*);
the family Aegeriidae such as cherry treeborer (*Conopia hector*);
the family Stathmopodidae such as persimmon fruit moth (*Stathmopoda masinissa*);
the family Gelechidae such as pink bollworm (*Pectinophora gossypiella*);
the family Carposinidae such as peach fruit moth (*Carposina niponensis*);
the family Heterogeneidae such as oriental moth (*Monema flavescens*);
the family Pyralidae such as rice leafroller (*Cnaphalocrocis medinalis*), Asiatic rice borer (*Chilo suppressalis*) or cotton caterpillar (*Diaphania indica*);
the family Hesperidae such as rice skipper (*Pamara guttata*);
the family Papilionidae such as smaller citrus dog (*Papilio xuthus*);
the family Pieridae such as common white (*Pieris rapae crucivora*);
the family Lygaenidae such as pea blue butterfly (*Lampides boeticus*);
the family Geometridae such as mugwort looper (*Ascotis selenaria*);
the family Sphingidae such as sweetpotato horn worm (*Agrius convolvuli*);
the family Notodontidae such as cherry caterpillar (*Phalera flavescens*);
the family Lymantridae such as tea tussock moth (*Euproctis pseudoconspersa*);
the family Arctiidae such as fall webworm (*Hyphantria cunea*); and the like.

Pests of the order Coleoptera include for example
the family Scarabaeidae such as cupreous chafer (*Anomala cuprea*), citrus flower chafer (*Oxycetonia jucunda*) or Japanese beetle (*Popillia japonica*);
the family Buprestidae such as flatheaded citrus borer (*Agrilus auriventris*);
the family Elateridae such as sweetpotato wireworm (*Melanotus fortnumi*);.
the family Coccinellidae such as twenty-eight-spotted ladybird (*Henosepilachna vigintioctopunctata*);
the family Cerambycidae such as white-spotted longicorn beetle (*Anoplophora malasiaca*) or grape borer (*Xylotrechus pyrrhoderus*);
the family Chrysomelidae such as cucurbit leaf beetle (*Aulacophora femoralis*), striped flea beetle (*Phyllotreta striolata*) or rice leaf beetle (*Oulema oryzae*);
the family Attelabidae such as peach curculio (*Rhynchites heros*);
the family Brentidae such as sweetpotato weevil (*Cylas formicarius*);
the family Curculionidae such as *Curculio dentipes* or rice water weevil (*Lissorhoptrus oryzophilus*); and the like.

Pests of the order Hemiptera include for example
the family Pentatomidae such as brown-winged green bug (*Plautia stali*) or *Halyomorpha mista;* the family Urostylidae such as pear stink bug (*Urochela luteovaria*);
the family Coreidae such as *Cletus punctiger;*
the family Alydidae such as rice bug (*Laptocorisa chinensis*);
the family Pyrrhocoridae such as cotton bug (*Dysdercus cingulatus*);
the family Tingidae such as pear lace bug (*Stephanitis nashi*);
the family Miridae such as *Lygocoris spinolai;*
the family Cidadidae such as *Platypleura kaempferi;*
the family Aphrophoridae such as grape spittlebug (*Aphrophora vitis*);
the family Tettigellidae such as rice leafhopper (*Cicadella spectra*);
the family Cicadellidae such as grape leafhopper (*Arboridia apicalis*) or tea green leafhopper (*Empoasca onukii*);
the family Deltocephalidae such as green rice leafhopper (*Nephotettix cincticeps*);
the family Delphacidae such as brown rice planthopper (*Nilaparvata lugens*);
the family Platidae such as green flatid planthopper (*Geisha distinctissima*);
the family Psyllidae such as pear sucker (*Psylla pyrisuga*);
the family Aleyrodidae such as greenhouse whitefly (*Trialeurodes vaporariorum*) or silver leaf whitefly (*Bemisia argentifolii*);
the family Phylloxera such as *Moritziella castaneivora;*
the family Pemphigidae such as woolly apple aphid (*Eriosoma lanigerum*);
the family Aphididae such as cotton aphid (*Aphis gossypii*), green peach aphid (*Myzus persicae*) or rice root aphid (*Rhopalosiphum rufiabdominalis*);
the family Margarodidae such as cottony cushion scale (*Icerya purchasi*);
the family Pseudococcidae such as citrus mealy bug (*Planococcus citri*);
the family Coccidae such as red wax scale (*Ceroplastes rubens*);
the family Diaspidiae such as San Jose scale (*Comstockaspis perniciosa*) or white peach scale (*Pseudaulacaspis pentagona*); and the like.
Pests of the order Thysanoptera include for example
the family Thripidae such as western flower thrips (*Frankliniella occidentalis*), yellow tea thrips (*Scirtothrips dorsalis*) or Thrips palmi;
the family Phlaeothripidae such as *Ponticulothrips disospyrosi* or rice aculeated thrips (*Haplothrips aculeatus*); and the like.
Pests of the order Hymenoptera include for example
the family Tenthredinidae such as cabbage sawfly (*Athalia rosae japonensis*),
the family Argidae such as apple argid sawfly (*Arge mali*);
the family Cynipidae such as chestnut gall wasp (*Dryocosmus kuriphilus*);
the family Megachilidae such as rose leafcutter (*Megachile nipponica*); and the like.
Pests of the order Diptera include for example
the family Cecidomyiidae such as soybean pod gall midge (*Asphondylia yushimai*);
the family Tephritidae such as melon fly (*Dacus cucurbitae*);
the family Ephydridae such as rice leafminer (*Hydrellia griseola*);
the family Dorosophilidae such as cherry drosophila (*Drosophila suzukii*)

the family Agromyzidae such as garden pea leafminer (*Phytomyza horticola*) or legume leafminer (*Liriomyza trifolii*);
the family Anthomyiidae such as onion maggot (*Hylemya antiqua*); and the like.
Pests of the order Orthoptera include for example
the family Tettigoniidae such as *Homorocoryphus lineosus;*
the family Gryllidae such as green tree criket (*Calyptotrypus hibinonis*);
the family Gryllotalpidae such as African mole cricket (*Gryllotalpa africana*);
the family Acrididae such as rice grasshopper (*Oxya yezoensis*); and the like.
Pests of the order Collembola include for example
the family Sminthuridae such as lucerne flea (*Sminthurus viridis*);
the family Onychiuridae such as *Onychiurus matsumotoi*; and the like.
Pests of the order Isoptera include for example the family Termitidae such as *Odontotermes formosanus* and pests of the order Dermaptera include for example the family Labiduridae such as *Labidura riparia* and the like.

The followings can be exemplified as pests belonging to the classes Crustacea and Arachnida in the phylum Arthropoda.

Pests of the order Isopoda in the class Crustacea include for example the family Armadillidae such as pillbug (*Armadillidium vulgare*).

Pests of the order Acarina in the class Arachnida include for example
the family Tarsonemidae such as broad mite (*Polyphagotarsonemus latus*) or cyclamen mite (*Steneotarsonemus pallidus*);
the family Europidae such as winter grain mite (*Penthaleus major*);
the family Tenuipalpidae such as citrus flat mite (*Brevipalpus lewisi*);
the family Tetranychidae such as European red mite (*Panonychus ulmi*);
the family Eriophyidae such as pink citrus rust mite (*Aculops pelekassi*), *Aculus schlechtendali* or *Eriophyes chibaensis*; and the like.

Pests of the class Gastropoda in the phylum Mollusca include the order Mesogastropoda such as apple snail (*Pomacea canaliculata*), the order Stylommatophora such as giant African snail (*Achatina fulica*), *Incilaria bilineata, Milax gagates*, giant garden slug (*Limax marginatus*) or *Acusta despecta*; and the like.

The followings can be exemplified as pests belonging to the classes Secernentea and Adenophorea in the phylum Nematoda.

Pests of the order Tylenchida in the class Secernentea include for example
the family Anguinidae such as *Ditylenchus destructor;*
the family Tylebchorhynshidae such as tobacco stunt nematode (*Tylebchorhynchus claytoni*);
the family Pratylenchidae such as Cobb root-lesion nematode (*Pratylenchus penetrans*) or coffee root-lesion nematode (*Pratylenchus coffee*);
the family Hoplolaimidae such as Cobb spiral nematode (*Helicotylenchus dihystera*);
the family Heteroderidae such as potato cyst nematode (*Globodera rostochiensis*);
the family Meloidogynidae such as southern-root-knot nematode (*Meloidogyne incognita*);
the family Criconematidae such as ring nematode (*Criconemoides* sp.);

the family Nothotylenchidae such as strawberry bud nematode (*Nothotylenchus acris*);
the family Aphelenchoididae such as strawberry nematode (*Aphelenchoides fragariae*); and the like.

Pests of the order Dorylaimida in the class Adenophorea include for example
the family Longidoridae such as dagger nematode (*Xiphinema* sp.);
the family Trichodoridae such as stubby root nematode (*Trichodorus* sp.); and the like.

The compounds of the present invention are effective for repellent, control or extermination of pests that injure natural forests, artificial forests and trees in city green space or have an effect on vital force of these trees. In such a scene concrete pests include the followings.

The followings can be exemplified as pests belonging to the classes Insecta and Arachnida in the phylum Arthropoda.

Pests of the order Lepidoptera include for example
the family Lymantriidae such as ceder tussock moth (*Dasychira abietis*) or gypsy moth (*Lymantria dispar japonica*);
the family Lasiocampidae such as pine caterpillar (*Dendrolimus spectabilis*) or hemlock caterpillar (*Dendrolimus superans*);
the family Pyralidae such as larch pyralid (*Cryptoblabes angustipennella*);
the family Noctuidae such as cutworm (*Agrotis segetum*),
the family Tortricidae such as larch webworm (*Ptycholomoides aeriferana*), nut fruit tortrix (*Cydia kurokol*) or cryptomeria conemoth (*Cydia cryptomeriae*);
the family Arctiidae such as fall webworm (*Hyphantria cunea*);
the family Nepticulidae such as *Stigmella castanopsiella*;
the family Heterogeneidae such as *Latoia lepida*; and the like.

Pests of the order Coleoptera include for example
the family Scarabaeidae such as soybean beetle (*Anonala rufocuprea*) or *Heptophylla picea;*
the family Buprestidae such as flatheaded zelkova borer (*Agrilus spinipennis*);
the family Cerambycidae such as pine sawyer (*Monochamus grandis*);
the family Chrysomelidae such as *Basilepta pallidulum;*
the family Curculionidae such as *Scepticus griseus* or *Shirahoshizo pini;*
the family Phynchophoridae such as *Sipalinus gigas;*
the family Scolytidae such as pine shoot beetle (*Tomicus piniperda*) or maple timber beetle (*Trypodendron aceris*);
the family Bostrychidae such as *Rhizopertha dominica*; and the like.

Pests of the order Hemiptera include for example
the family Aphididae such as *Cinara todocola;*
the family Adelgidae such as *Adelges japonicus;*
the family Coccoidea such as *Aspidiotus cryptomeriae;*
the family Coccidae such as Indian wax scale (*Ceroplastes ceriferus*); and the like.

Pests of the order Hymenoptera include for example
the family Tenthredinidae such as larch sawfly (*Pachynematus itoi*),
the family Diprionidae such as pine sawfly (*Neodiprion sertifer*);
the family Cynipidae such as chestnut gall wasp (*Dryocosmus kuriphilus*); and the like.

Pests of the order Diptera include for example
the family Tipulidae such as rice crane fly (*Tipula aino*);
the family Anthomyiidae such as larch corn maggot (*Hylemya laricicola*);
the family Cecidomyiidae such as cryptomeria needle gall midge (*Contarinia inouyei*) or pine bud gall midge (*Contarinia matsusintome*); and the like.

Pests of the order Acarina in the class Arachnida include for example spruce spider mite (*Oligonychus ununguis*).

Pests of the order Tylenchida in the class Secernentea in the phylum Nematoda include for example the family Philomycidae such as pine wood nematode (*Bursaphelenchus lignicolus*); and the like.

The insecticide containing the compound of the present invention as active ingredient can be used as a formulation effective in the above-mentioned scene of agriculture or forestry, or in any arbitrary application form prepared from the formulation, alone or by a simultaneous use of other active compounds such as an insecticide, acaricide, nematicide, fungicide, synergist, plant growth regulator, herbicide or poison bait, etc., or in an admixture therewith. More concrete active compounds include for example the followings to Which the present invention is not limited.

Active Compounds of Insecticides or Acaricides:

Organophosphorus compounds include for example dichlorvos, fenitrothion, malathion, naled, chlorpyrifos, diazinon, tetrachlorvinphos, fenthion, isoxathion, methidathion, salithion, acefate, dimeton-S-methyl, disulfoton, monocrotophos, azinphos-methyl, parathion, phosalone, pirimiphos-methyl, prothiofos and the like.

Carbamate compounds include for example metolcarb, fenocarb, propoxur, carbaryl, ethiofencarb, pirimicarb, bendiocarb, carbosulfan, carbofuran, methomyl, thiodicarb and the like.

Organochlorine compounds include for example lindane, DDT, endosulfan, aldrin, chlordane and the like.

Pyrethroids include for example permethrin, cypermethrin, deltamethrin, cyhalothrin, cyfluthrin, acrinathrin, fenvalerate, etofenprox, silafluofen, fluvalinate, flucythrinate, bifenthrin, allethrin, phenothrin, fenpropathrin, cyphenothrin, furamethrin, resmethrin, transfluthrin, prallethrin, flufenprox, halfenprox, imiprothrin and the like.

Neonicotinoids include for example imidacloprid, nitenpyram, acetamiprid, dinotefuran, thiamethoxam, thiacloprid, clothianidin and the like.

Insect growth regulators such as phenyl benzoyl ureas include for example diflubenzuron, chlorfluazuron, triflumuron, flufenoxuron, hexaflumuron, lufemuron, teflubenzuron, novaluron, buprofezin, tebufenozide, chromafenozide, methoxy fenozide, cyromazine and the like.

Juvenile hormone mimics include for example pyriproxyfen, fenoxycarb, methoprene, hydroprene and the like.

Insecticidal materials produced by microorganisms include for example abamectin, milbemectin, nikkomycins, emamectin benzoate, ivermectin, spinosad and the like.

Other insecticides include for example cartap, bensultap, chlorfenapyr, diafenthiuron, nicotine sulfate, metaldehyde, fipronil, ethiprole, pymetrozin, indoxacarb, tolfenpyrad, pyridalyl, flurimfen, BT agents and the like.

Active compounds of acaricides include for example dicofol, phenisobromolate, benzomate, tetradifon, polynactin-complex, amitraz, propargite, fenbutatin oxide, tricyclohexyltin hydroxide, tebufenpyrad, pyridaben, fenpyroximate, pyrimidifen, fenazaquin, clofentezine, hexythiazox, acequinocyl, quinomethionat, fenothiocarb, etoxazole, bifenazate, fluacrypyrim and the like.

Active compounds of nematicides include for example methyl isocyanate, fosthiazate, cadusafos, oxamyl, mesulfenfos and the like.

Poison baits include for example monofluoroacetate, warfarin, coumatetralyl, diphacin and the like.

Active compounds of fungicides include for example an inorganic copper, an organic copper, sulfur, maneb, thiuram, thiadiazine, captan, chlorothalonil, iprobenfos, thiophanatamethyl, benomyl, thiabendazole, iprodione, procymidone, pencycuron, metalaxyl, sandofan, baileton, triflumizole, fenarimol, triforine, dithianon, triazine, fluazinam, probenazole, diethofencarb, isoprothiolane, pyroquilon, iminoctadine acetate, echlomezol, dazomet, kresoxim-methyl and the like.

Active compounds of herbicides include for example bialaphos, sethoxydim, trifluralin, mefenacet and the like.

Active compounds of plant growth regulators include for example indoleacetic acid, ethephon, 4-CPA and the like.

Active compounds of repellents include for example carane-3,4-diol, N,N-diethyl-m-triamide (Deet), limonene, linalool, citronellal, menton, hinokitiol, menthol, graniol, eucalyptole and the like.

Active compounds of synergists include for example bis-(2,3,3,3-tetrachloropropyl) ether, N-(2-ethylhexyl)bicyclo[2.1.1]hept-5-en-2,3-dicarboxy imide, α-[2-(2-butoxyethoxy)ethoxy]-4,5-methylenedioxy-2-propyl toluene and the like.

The insecticide of the present invention can be used in any arbitrary application form, and be formulated for example in a form of wettable powders, water dispersible granules, water soluble powders, emulsifiable concentrates, liquid formulations, flowables such as suspension concentrate in water or emulsifiable concentrate in water, encapsulations, dusts, granules, aerosols and the like, after adding any auxiliary substances to the compound of the present invention. These formulations may contain the active ingredients such as the compounds of the present invention, etc. in any arbitrary amount, and generally the total amount of the active ingredients is selected from a range of 0.001 to 99.5% by weight depending on several conditions such as a formulation form or application method, etc. For example, it is suitable to prepare formulations so as to contain the active ingredients in an amount of about 0.01 to 90% by weight, preferably 1 to 50% by weight in case of wettable powders, water dispersible granules, water soluble powders, emulsifiable concentrates, liquid formulations, flowables, encapsulations or the like, in an amount of 0.1 to 50% by weight, preferably 1 to 10% by weight in case of dusts, granules or the like, and in an amount of about 0.001 to 20% by weight, preferably 0.01 to 2% by weight in case of aerosols or the like.

As the auxiliary substance, for example a carrier (diluent), a spreader, an emulsifier, a wetting agent, a dispersing agent, a disintegrator or the like may be used in order to improve repellent effect, control effect or extermination effect of pests and improve stability or dispersibility.

Liquid carriers include water, aromatic hydrocarbons such as toluene or xylene, alcohols such as methanol, butanol or glycol, ketones such as acetone, amides such as dimethylformamide, sulfoxides such as dimethylsulfoxide, methyl naphthalene, cyclohexane, animal and vegetable oils, fatty acids and the like. In addition, solid carriers include clay, kaolin, talc, diatomaceous earth, silica, calcium carbonate, montmorillonite, bentonite, feldspar, quartz, alumina, sawdust, nitrocellulose, starch, gum arabic and the like.

As the emulsifier or dispersing agent, surfactants can be generally used. The surfactants include for example anionic, cationic, non-ionic oramphoteric surfactants such as higher alcohol sodium sulfate, stearyl trimethyl ammonium chloride, polyoxyethylene alkyl phenyl ethers or lauryl betaine.

The followings may be used: a spreader such as polyoxyethylene nonyl phenyl ether or polyoxyethylene lauryl phenyl ether; a wetting agent such as dialkylsulfosuccinate; an adhesive agent such as carboxymethyl cellulose or polyvinyl alcohol; a disintegrator such as sodium lignin sulfonate or sodium lauryl sulfonate.

For example, in case of wettable powders, raw powders are prepared by mixing the compound of formula (I) as active ingredient, a solid carrier and a surfactant, etc. Further, the raw powders can be applied by diluting it with water to a prescribed concentration when it is used.

In case of emulsifiable concentrates, they can be prepared by mixing a solvent and a surfactant to the active ingredient. Further, the concentrate can be applied by diluting it with water to a prescribed concentration when it is used.

In case of dusts, they can be applied as such after mixing the active ingredient, a solid carrier and the like. In case of granules, they can be applied as such after mixing and granulating the active ingredient, a solid carrier, a surfactant and the like.

In the meanwhile, the preparation method of each of the above-mentioned formulations is not limited to the above-mentioned ones, and those skilled in the art can select suitably depending on the kind of active ingredient, the object of application or the like.

The application method is selected depending on the kind or population of pests, or the kind, cultivating form or growth condition of crops or trees to be objected, and for example in case where pests to be controlled are arthropods, gastropods or nematodes, etc., generally the area where injury due to the pests occurs or the area where such an injury is predicted is treated with the insecticide in an active ingredient amount of 0.1 to 1000 g, preferably 1 to 100 g per 10 are (a).

A concrete application method comprise diluting for example the above-mentioned wettable powders, water dispersible granules, water soluble powders, emulsifiable concentrates, liquid formulations, flowables such as suspension concentrate in water or emulsifiable concentrate in water, encapsulations, or the like with water, and spraying it to crops or trees to be objected in an amount of 10 to 1000 liter per 10 a depending on the kind, cultivating form or growth condition of the crops or trees. In addition, in case of dusts, granules or aerosols, they may be applied to crops or trees in a form of the formulations in the above-mentioned application rate.

In case where pests to be objected injure crops or trees mainly in soil, for example wettable powders, water dispersible granules, water soluble powders, emulsifiable concentrates, liquid formulations, flowables such as suspension concentrate in water or emulsifiable concentrate in water, encapsulations, or the like are diluted with water to obtain a diluted formulation, and the diluted formulation is sprayed in an application rate of 5 to 500 liter per 10 a. In this case, the diluted formulation may be sprayed on the surface of soil in a manner that it is dispersed evenly on the whole application area or drenched in soil. In case where formulations are dusts or granules, the formulation may be sprayed as such on the surface of soil in a manner that it is dispersed evenly on the whole application area. When spraying or drench is carried out, the formulation may be applied only the periphery of seeds, crops, trees or the like to be protected from the injury of pests, or during or after spraying the soil is cultivated thereby dispersing the active ingredients mechanically.

Further, the insecticide containing the compound of the present invention as active ingredient may be adhered on plant seeds by any known methods. Such a treatment provides not only a protection from injury by pests in soil after sowing the seeds but also a protection of stems or flowers of plants or fruits after growing from injury by pests, In case where the above-mentioned trees or fallen trees, processed woods, stored woods or the like are protected from injury by termites or beetles, application methods include spraying, injection, drench or coating of an oil solution, an emulsifiable concentrate, a wettable powder or a sol, or spraying of a dust or granule to the periphery soil of trees or woods. In such a scene, the pest control agent containing the compound of the present invention as active ingredient may be used alone or by a simultaneous use of other active compounds such as insecticides, acaricides, nematicides, fungicides, repellents, synergists or the like, or in an admixture therewith.

These formulations may contain the active ingredients such as the compounds of the present invention, etc. in any arbitrary amount, and generally the amount of the active ingredients is selected from a range of 0.0001 to 95% by weight, preferably 0.005 to 10% by weight in oil solutions, dusts or granules, or 0.01 to 50% by weight in emulsifiable concentrates, wettable powders or sols. Concretely, in case where for example termites or beetles are exterminated or controlled, the formulation is sprayed on soil or the surface of woods at 0.01 to 100 g of the active ingredients per 1 $m^2$.

(B) Livestock Industry, Fishery Scene

The insecticides containing the compounds of the present invention are effective for repellent, extermination or control of pests such as arthropods, nematodes, trematodes, tapeworms, protozoans or the like which parasitize internally or externally animals fed in livestock industry or fishery, or house such as pets, or household, and do a direct harm, such as skin-eating or blood-sucking or do an injury, such as spreading of diseases. They can be also used for prevention and treatment diseases in related with the pests. Animals to be objected include vertebrates, for example livestock such as cattle, sheep, goat, horses, pigs that are warm-blood vertebrates, cultured fishes; further domestics, dogs or cats or rodents such as mice, rats, hamsters or squirrels; and pets or laboratory animals that are carnivores such as ferrets and fishes.

Among the pests, the followings can be exemplified as ones belonging to the classes Insecta and Arachnida in the phylum Arthropoda.

Pests of the order Diptera include for example
the family Tabanidae such as *Tabanus rufidens, Odagmia ornata* or *Tabanus chrysurus*;
the family Muscidae such as *Calliphora nigribarbis, Musca domestica* or *Stomoxys calcitans*;
the family Gasterophilidae such as *Gasterophilus intestinalis*;
the family Hypodermatidae such as *Hypoderma bovis*;
the family Calliphoridae such as *Lucilia cuprina*;
the family Phoridae such as *Megaselia spiracularis*;
the family Sepsidae such as *Sepsis monostigma*;
the family Psychodidae such as *Clogmia albipunctata* or *Tinearia alternata*;
the family Culicidae such as *Anopheles sinensis, Culex tritaeniorhynchus* or *Aedes albopictus*;
the family Simuliidae such as black fly (*Prosimulium hirtipes*);
the family Ceratopogonidae such as *Culicoides oxystoma* or *Culicoides arakawae*; and the like.

In addition, pests of the order Siphonaptera include for example the family Pulicidae such as *Ctenocephalides felis* or *Ctenocephalides canis*; and the like.

Pests of the order Anoplura include for example the family Echinophthiriidae such as *Haematopinus suis* or *Haematopinus eurysternus*;
the family Trichodectidae such as *Haematopinus asini*;
the family Linognathidae such as *Linognathus vituli*;
the family Menoponidae such as *Menopon gallinae*; and the like.

Pests of the order Acarina in the class Arachnida in the phylum Arthropoda include for example
the family Metastigmata such as *Haemaphysalis longicornis, Ixodes ovatus, Boophilus microplus* or *Amblyomma testudinarium*;
the family Macronyssidae such as *Ornithonyssus sylviarum*;
the family Dermanyssidae such as chicken mite (*Dermanyssus gallinae*);
the family Demodicidae such as *Demodex phylloides*;
the family Sarcoptidae such as *Notoedres cati* or *Sarcoptes scabiei*;
the family Psoroptidae such as *Otodectes cynotis* or *Psoroptes communis*; and the like.

The followings can be exemplified as pests of the class Secernentea in the phylum Nematoda.

The order Strongylida include for example cattle hookworm (*Bunostomum phlebotomum*), *Stephanurus dentatus, Metastrongylus apri, Trichostrongylus colubriformis* or *Oesophagostomum radiatum*.

The order Ascaridida include for example *Toxocara suum* or *Ascaridia galli*, etc.

The class Trematoda in the phylum Plathelminthes include for example oriental blood fluke (*Schistosoma japonicum*), liver fluke (*Fosciola hepatica*), *Paramphistomum cervi, Paragonimus westermanii* or *Prosthogonimus ovatus*, etc.

The class Cestoda include for example *Anoplocephala perfoliata, Moniezia expansa, Moniezia benedeni, Raillietina tetragona* or *Raillietina cesticillus*, etc.

The class Mastigophorea in the phylum Protozoa include the order Rhizomastigida such as *Histomonas*, the order Protomastigida such as *Leishmania* or *Trypanosoma*, the order Polymastigida such as *Giardia*, the order Trichomonadida such as *Trichomonas*, and the like.

The order Amoebida in the class Sarcodinea include for example *Entamoeba* and the like, the subclass Piroplasmia in the class Sporozoea include for example *Theilaria, Babesia* and the like, and the subclass Telosporidia such as *Eimeria, Plasmodium, Toxoplasma* and the like.

The insecticide containing the compound of the present invention as active ingredient can be used as a formulation effective in the above-mentioned livestock industry or fishery scene, or in any arbitrary application form prepared from the formulation, alone or by a simultaneous use of other active compounds such as an insecticide, acaricide, nematicide, fungicide, synergist, plant growth regulator, herbicide or poison bait, etc., or in an admixture therewith. More concrete active compounds include for example the compounds listed in the item "(A) Agriculture or forestry scene" to which the present invention is not limited.

Concrete application methods comprise for example blending the insecticide in feeds for livestock or pets, or orally administrating a medical preparation that can be orally ingested, such as tablets, balls, capsules, paste, gel, beverage, medicinal feeds, medicinal drinking water, medicinal additional feeds, gradual-releasing large balls or other gradual-releasing devices prepared in such a manner to be stayed in the intestine, for example containing pharmaceutically acceptable carriers or coating materials, or percutaneously administrating in a form of a spray, a powder, grease, cream, ointment, emulsifiable concentrate, lotion, spot-on, pour-on, shampoo, etc.

The percutaneous or topical administration can be carried out by use of a device (for example a collar, a medallion, an ear-tag, etc.) attached to animals so that arthropods should be controlled locally or systematically.

Although concrete methods for oral or percutaneous administration in case where the insecticide of the present invention is used as antiparasitic agent will hereinafter be described, the present invention is not limited to these methods. In case where a medicinal beverage preparation is orally administered, the preparation is prepared by dissolving the active ingredient together with a suspending agent such as bentonite, a moistening agent or other excipients in a non-poisonous solvent or water to obtain a suspension or a dispersion. The preparation contains optionally an antifoaming agent. The beverage preparations generally contain the active ingredient in an amount of 0.01 to 1.0% by weight, preferably 0.01 to 0.1% by weight.

In case where the insecticide is orally administered in a form of dried solid unit, generally capsules, balls or tablets containing a prescribed amount of the active ingredient are used. They are prepared by homogeneously mixing the active component with suitably milled diluents, fillers, disintegrators or binders, such as starch, lactose, talc, magnesium stearate, plant gum or the like. For the prescription of the unit, the weight and content of antiparasitic agents may be determined depending on the kind of host animals to be treated, the level of infection, the kind of parasites and the body weight of the hosts.

In case where an active compound is administered, through a feed, the active compound may be used by homogeneously dispersing it in the feed, or be used as top-dressing or in a form of pellet. In order to accomplish antiparasitic effect, the active compound is contained in an amount of 0.0001 to 0.05% by weight, preferably 0.0005 to 0.01% by weight in the final feed.

In case where an active compound is dissolved or dispersed in a liquid excipient, the insecticide may be parenterally administered by intraproventriculus, intramuscular, endotracheal or subcutaneous injection. As it is parenterally administrated, it is preferable to mix the active compound with vegetable oil such as peanut oil or cotton seed oil. The formulation generally contains the active compound in an amount of 0.05 to 50% by weight, preferably 0.1 to 0.2% by weight. The formulation in which a carrier such as dimethylsulfoxide or hydrocarbon solvent, etc. is mixed can be administered directly or locally to the outer surface of livestock or pets by a spray or direct pouring.

(C) Public Hygiene Scene, etc.

Also, the insecticides of the present invention are effective for repellent, extermination or control of pests in public hygiene scene which exert an adverse effect on the environment of clothing, food and housing, cause harm to human body or transport or mediate pathogens, or the like, in order to maintain good public hygiene state. Concretely, the pesticides of the present invention are effective for repellent, extermination or control of pests belonging to Lepidoptera, Coleoptera, Thysanura, Blattariae, Cyclorhapha and Acarina. The pests in the public hygiene scene concretely include the followings.

The followings can be exemplified as the class Insecta in the phylum Arthropoda.

The pests of the order Lepidoptera include for example the family Lymantriidae such as brown tail moth (*Euproctis similis*);
the family Lasiocampidae such as quercus lasiocampid (*Dendrolimus undans flaveola*);
the family Heterogeneidae such as green cochlid (*Latoia consocia*);
the family Zygaenidae such as bamboo zygaenid (*Artona funeralis*);
the family Pyralidae such as almond moth (*Ephestia cautella*), Mediterranean flour moth (*Anagasta kuehniella*) or Indian meal moth (*Plodia interpunctella*);
the family Gelechiidae such as grain moth (*Sitotroga cerealella*);
the family Tineidae such as casemaking clothes moth (*Tinea pellionella*) or webbing clothes moth (*Tineola bisselliella*); and the like.

The pests of the order Coleoptera include for example the family Oedemeridae such as *Xanthochroa waterhousei;*
the family Meloidae such as *Epicauta gorhami;*
the family Staphylinidae such as *Paederus fuscipes;*
the family Rhynchophoridae such as maize weevil (*Sitophilus zeamais*) or rice weevil (*Sitophilus oryzae*);
the family Bruchidae such as adzuki bean weevil (*Callosobruchus chinensis*), pee weevil (*Bruchus pisorum*) or broadbean weevil (*Bruchus rufimanus*);
the family Tenebrionida such as red flour beetle (*Tribolium castaneum*);
the family Cucujidae such as sawtoothed grain beetle (*Oryzaephilus surimamensis*) or flat grain beetle (*Cryptolestes pusillus*);
the family Anobiidae such as cigarette beetle (*Lasioderma serricorne*) or biscuit beetle (*Stegobium paniceum*);
the family Dermestidae such as black carpet beetle (*Attagenus unicolor*), varied carpet beetle (*Anthrenus verbasci*) or hide beetle (*Dermestes maculatus*);
the family Ptinidae such as *Gibbium aequinoctiale;*
the family Bostrychidae such as bamboo powder post beetle (*Dinoderus minutus*) or *Rhizopertha dominica;*
the family Lyctidae such as powder post beetle (*Lyctus brunneus*); and the like.

The pests of the order Hymenoptera include for example the family Vespidae such as *Vespa xanthoptera;*
the family Formicidae such as *Pachycondyla chinensis;*
the family Pompilidae such as *Cyphononyx dorsalis*; and the like.

The pests of the order Diptera include for example the family Culicidae such as *Ochlerotatus japonicus;*
the family Ceratopogonidae such as *Culicoides melleuss;*
the family Chironomidae such as *Chironomus yoshimatsui;*
the family Simuliidae such as *Simulium japonicum;*
the family Tabanidae such as;
the family Muscidae such as *Musca domestica;*
the family Anthomyiidae such as *Fannia canicularis;*
the family Calliphoridae such as *Phormiaregina;*
the family Sarcophagidae such as *Boettcherisca peregrina;*
the family Drosophilidae such as *Drosophila melanogaster,*
the family Piophilidae such as cheese skipper (*Piophila casei*); and the like.

The pests of the order Siphonaptera include for example the family Pulicidae such as *Pulex irritans*; and the like.

The pests of the order Collembola include for example the family Hypogastruridae such as *Ceratophysella communis;* and the like.

The pests of the order Blattaria include for example the family Blattellidae such as *Blattella germanica* or *Asiablatta kyotensis;* the family Blattidae such as American cockroach (*Periplaneta americana*), smokybrown cockroach (*Periplaneta fuliginosa*) or Japanese cockroach (*Periplaneta japonica*); and the like.

The pests of the order Orthoptera include for example the family Gryllacrididae such as Japanese camel cricket (*Diestrammena japonica*) or *Parudenus falklandicus*; and the like.

The pests of the, order Anoplura include for example the family Pediculidae such as *Pediculus humanus;* the family Pthiridae such as *Pthirus pubi*; sand the like.

The pests of the order Hemiptera include for example the family Cimicidae such as *Cimex lectularius;* the family Reduviidae such as *Isyndus obscurus*; sand the like.

The pests of the order Isoptera include for example the family Rhinotermitidae such as *Reticulitermes speratus* or *Coptotermes formosanus;* the family Kalotermitidae such as *Cryptotermes domesticus*; sand the like, and the pests of the order of Psocoptera include for example the family Atropidae such as reticulate winged book louse (*Lepinotus reticulatus*); the family Liposcelidae such as *Liposcelis bostrychophilus*; and the like.

The pests of the order Thysanura include for example the family Lepismatidae such as oriental silver fish (*Ctenolepisma villosa*) or silver fish (*Lepisma saccharina*); and the like.

The followings can be exemplified as the class Arachnida in the phylum Arthropoda.

The pests of the order Acarina include for example the family Ixodidae such as *Ixodes persulcatus;* the family Macronyssidae such as *Ornithonyssus bacoti;* the family Cheyletidae such as *Chelacaropsis moorei;* the family Pyemotidae such as *Pyemotes tritici;* the family Demodicidae such as *Demodex folliculorum;* the family Pyroglyphidae such as *Dermatophagoides pteronyssinus;* the family Scarcoptidae such as *Sarcoptes scabiei;* the family Trombiculidae such as *Leptotrombidium akamushi;* the family Acaridae such as mold mite (*Tyrophagus putrescentiae*) or *Lardoglyphus konoi;* the family Carpoglyphidae such as dried-fruit mite (*Carpoglyphus lactis*); and the like.

The pests of the order Araneae include for example the family Clubionidae such as *Chiracanthium japonicum;* the family Heteropodidae such as *Heteropoda venatoria;* the family Pholcidae such as *Spermophora amabilis* or *Pholcus phalangioides;* the family Urocteidae such as *Uroctea compactilis;* the family Salticidae such as *Plexippus paykulli* or *Plexippus setipes*; and the like.

The pests of the order Scoriones include for example the family Buthidae such as *Isometrus europaeus*; and the like.

Other pests belonging to the phylum Arthropoda include the order Scolopendromorpha for example the family Scolopendridae such as Japanese large centipede (*Scolopendra subspinipes japonica*); the order Scutigeromorpha for example the family Scutigeridae such as *Thereuonema tuberculata*; and the like. In addition, the pests belonging to the order Polydesmida in the class Diplopoda in the phylum Arthropoda include for example the family Paradoxosomatidae such as *Oxidus gracilis*; and the pests belonging to the order Isopoda in the class Crustacea in the phylum Athropoda include for example the family Porcellionidae such as *Porcellio* sp.; and the like.

Further, the pests belonging to the order Gnathobdellida in the class Hirudinea in the phylum Annelida include for example the family Haemadipsidae such as *Haemadipsa zeylanica*; and the like.

The insecticide containing the compound of the present invention as active ingredient can be used as a formulation effective in the above-mentioned public hygiene scene, or in any arbitrary application form prepared from the formulation, alone or by a simultaneous use of other active compounds such as an insecticide, acaricide, nematicide, fungicide, synergist, plant growth regulator, herbicide or poison bait, etc., or in an admixture therewith. More concrete active compounds include for example the compounds listed in the item "(A) Agriculture or forestry scene" to which the present invention is not limited.

The insecticide of the present invention can be used in any arbitrary application form, and for example in case where the above-mentioned animal or plant products are protected, the pests can be controlled by spraying the oil solution, emulsifiable concentrate, wettable powder or dust of the insecticide, by setting a resin transpiration agent, by treating with the smoking pesticide or fogging agent of the insecticide, by setting the granule, tablet or poison bait of the insecticide, or by atomizing the aerosol of the insecticide. These formulations preferably contain the active ingredients in an amount of 0.0001 to 95% by weight.

The application is carried out as follows, for example. When pests are arthropods which directly cause damage or are mediators of diseases, the application comprises spraying, injecting, pouring or coating an oil solution, emulsifiable concentrate, wettable powder or the like in the periphery where the arthropods may be present, spraying a dust there, or treating there with a fumigant, a heat-fogging agent such as a mosquito coil, a self-combustion type smoking agent or chemical reaction type fogging agent, a smoking agent such as a fogging, or a formulation such as ULV formulation. Alternatively, the application may be carried out by setting other types of formulations, such as a granule, tablet or poison bait, or adding dropwise a floating dust formulation or granule in a water channel, well, water reservoir or other flowing or retained water.

Further, the pests belonging to tussock moths that are pests also in agriculture or forestry can be controlled in a similar way as the methods described in the item "(A) Agriculture or forestry scene". In addition, for flies it is effective to mix the insecticide in the feed of livestock so that the active ingredient could be introduced into the feces, and for mosquitos it is effective to transpire the active ingredient in the air with an electric mosquito-repellent apparatus.

The formulations of these application types may be present as an admixture with other active compounds as mentioned above, such as an insecticide, acaricide, nematicide, fungicide, repellent or synergist, and it is preferable to contain the active compounds in an total amount of 0.0001 to 95% by weight in total therein. In the meanwhile, when the formulation is used, it may be simultaneously used with other active compounds.

In case where houses or wooden furnishings are protected against pests such as termites or beetles, the application comprises spraying, injecting, pouring or coating an oil solution, emulsifiable concentrate, wettable powder, sol agent or the like in the periphery where the pests are present, or spraying a formulation in a form of dust there. Also in such a scene, the compound of the present invention may be simultaneously used with other active compounds such as an insecticide, acaricide, nematicide, fungicide, repellent or synergist, etc., or be used in an admixture therewith.

The total content of the active compounds such as the compound of the present invention in these formulations is arbitrary, and generally is 0.0001 to 95% by weight. It is preferable to contain the active compounds in an amount of 0.005 to 10% by weight in an oil solution, dust or granule, etc. and in an amount of 0.01 to 50% by weight in an emulsifiable concentrate, wettable powder or sol agent. Concretely, for example in case where termites or beetles are exterminated or controlled, the formulation is sprayed in the periphery or directly the surface thereof at 0.01 to 100 g of the active ingredients per 1 m$^2$.

In repellent, extermination or control of pests that cause damage to human body or transport or mediate pathogen, in addition to the above-mentioned applications, it is able to orally administrate a medical preparation that can be orally ingested, such as tablets, balls, capsules, paste, gel, beverage, medicinal feeds, medicinal drinking water, medicinal additional feeds, gradual-releasing large balls or other gradual-releasing devices prepared in such a manner to be stayed in the intestine, for example containing pharmaceutically acceptable carriers or coating materials, or to percutaneously administrate in a form of a spray, a powder, grease, cream, ointment, emulsifiable concentrate, lotion, spot-on, pour-on, shampoo, etc.

Concrete prescriptions of the formulation and the like are similar to those described in the item "(B) Livestock industry, fishery scene".

BEST MODE FOR CARRYING OUT THE INVENTION

Next, the present invention will be more concretely described based on examples. However, the present invention is not limited to them unless it is beyond the gist of the present invention.

SYNTHETIC EXAMPLE 1

Synthesis of N-(4-chlorobenzyl)-2-(4-trifluoromethylphenyl hydrazono) propionic acid amide (Compound No. 62)

4-Trifluoromethylphenyl hydrazine (8.40 g, 47.7 mmol) was suspended in 1 N hydrochloric acid (130 ml) and fully stirred with a mechanical stirrer to obtain a suspension. A aqueous solution (50 ml) of pyruvic acid (4.20 g, 47.7 mmol) was added to the suspension and vigorously stirred to a mixture. 6 hours later, the mixture was extracted with ethyl acetate and washed with a saturated brine. The washed mixture was dried on sodium sulfate and then filtered. The residue obtained by concentrating the resulting filtrate was washed with a mixed solvent of hexane and chloroform (1:1) to obtain 2-(4-trifluoromethylphenyl hydrazono) propionic acid (10.47 g, 42.52 mmol, 89%). mp 190–191° C.; $^1$H NMR (400 MHz, CDCl$_3$) δ 2.19 (3H, s), 7.23 (2H, d), 7.60 (2H, d), 7.87 (1H, brs).

2-(4-Trifluoromethylphenyl hydrazono) propionic acid (0.74 g, 3.0 mmol) was dissolved in dichloromethane (15 ml), and 4-chlorobenzyl amine (0.42 g, 3.0 mmol) and 1-[3-(dimethylamino) propyl]-3-ethylcarbodiimide hydrochloric acid salt (0.58 g, 3.0 mmol) were added thereto. 20 hours later, the mixture was washed with 1N hydrochloric acid, a saturated sodium bicarbonate water and a saturated brine, and dried on sodium sulfate and then filtrated. The residue obtained by concentrating the resulting filtrate was suspended in a mixed solvent of hexane and chloroform (1:1) and filtered to obtain N-(4-chlorobenzyl)-2-(4-trifluoromethylphenyl hydrazono) propionic acid amide (Compound No. 62) (0.83 g, 2.2 mmol, 75%).

Compound No. 62: mp 124–125° C.; $^1$H NMR (400 MHz, CDCl$_3$) δ 2.16 (3H, s), 4.55 (2H, d), 7.15 (2H, d), 7.27 (2H, d), 7.32 (2H, d), 7.53 (2H, d), 7.69 (1H, brs).

SYNTHETIC EXAMPLE 2

Synthesis of N-(4-methoxybenzyl)-2-(4-chlorophenyl hydrazono) propionic acid amide (Compound No. 93)

2-(4-Chlorophenyl hydrazono) propionic acid (0.64 g, 3.0 mmol) was dissolved in tetrahydrofuran (3 ml), and carbonyl diimidazole (0.49 g, 3.0 mmol) was added under cooling with ice. After stirring at room temperature for 1 hour, a solution of 4-methoxybenzyl amine (0.41 g, 3.0 mmol) in tetrahydrofuran (3 ml) was added thereto. 15 hours later, the mixture was washed with 6N hydrocloric acid, 1N aqueous solution of sodium hydroxide and a saturated brine, dried on sodium sulfate and then filtered. The residue obtained by concentrating the resulting filtrate was suspended in a mixed solvent of hexane and chloroform (1:1) and filtered to obtain N-(4-methoxybenzyl)-2-(4-chlorophenyl hydrazono) propionic acid amide (Compound No. 93) (0.76 g, 2.3 mmol, 76%).

Compound No. 93: mp 156–158° C.; $^1$H NMR (400 MHz, CDCl$_3$) δ 2.13 (3H, s), 3.8 (3H, s), 4.50 (2H, d), 6.88 (2H, d), 7.00 (2H, d), 7.23 (2H, d), 7.26 (2H, d), 7.44 (1H, brs).

SYNTHETIC EXAMPLE 3

Synthesis of N-(6-chloro-3-pyridylmethyl)-2-(4-trifluoromethylphenyl hydrazono) propionic acid amide (Compound No. 63)

2-(4-Trifluoromethylphenyl hydrazono) propionic acid (12.31 g, 50.0 mmol) was dissolved in dichloromethane (250 ml) and N,N-dimethylformamide (25 ml), and 5-aminomethyl-2-chloropyridine (7.13 g, 50.0 mmol) and 1-[3-(dimethylamino)propyl]-3-ethylcarbodiimide hydrochloric acid salt (9.59 g, 50.0 mmol) were added thereto. 30 hours later, the mixture was washed with 1N hydrochloric acid, a saturated sodium bicarbonate water and a saturated brine, and dried on sodium sulfate and then filtrated. The residue obtained by concentrating the resulting filtrate was purified with a silica gel chromatography to obtain N-(6-chloro-3-pyridylmethyl)-2-(4-trifluoromethylphenyl hydrazono) propionic acid amide (Compound No. 63) (14.47 g, 39.02 mmol, 78%).

Compound No. 63: mp 184° C.; $^1$H NMR (400 MHz, CDCl$_3$) δ 2.16 (3H, s), 4.57 (2H, d), 7.15 (2H, d), 7.31 (2H, d), 7.35 (1H, brt), 7.54 (2H, d), 7.64 (1H, s), 7.66 (1H, dd), 8.38 (1H, d).

SYNTHETIC EXAMPLE 4

Synthesis of N'-(4-chlorophenyl)-2-(4-chlorophenyl hydrazono) propionic acid hydrazide (Compound Nos. 104 and 105)

Pyruvic acid (0.88 g, 10.0 mmol) was dissolved in tetrahydrofuran (20 ml), and carbodiimidazole (1.62 g, 10 mmol) was added under colling with ice. After stirring at room temperature for 1 hour, 4-chlorophenyl hydrazine hydrochloric acid salt (3.94 g, 22.0 mmol) and triethylamine (2.53 g, 25 mmol) were added thereto. 6 hours later, 1N hydrochloric acid was added, and the organic phase was extracted with ethyl acetate, and washed with a saturated sodium bicarbonate water and a saturated brine, dried on sodium sulfate and then filtered. The residue obtained by concentrating the resulting filtrate was purified with a silica gel chromatography to obtain (E)-N'-(4-chlorophenyl)-2-(4-chlorophenyl hydrazono) propionic acid hydrazide (Compound No. 104) (0.63 g, 1.9 mmol, 14%) and (Z)-N'-(4-chlorophenyl)-2-(4-chlorophenyl hydrazono) propionic acid hydrazide (Compound No. 105) (0.06 g, 0.44 mmol, 4%).

Compound No. 104: mp 169–171° C.; $^1$H NMR (400 MHz, CDCl$_3$) δ 2.09 (3H, s), 6.10 (1H, brs), 6.80 (2H, d, J=8.8 Hz), 7.08 (2H, d, J=8.8 Hz), 7.16 (2H, d, J=8.8 Hz), 7.28 (2H, d, J=8.8 Hz), 7.67 (1H, brs), 8.55 (1H, brs).

Compound No. 105: mp 160–162° C.; $^1$H NMR (400 MHz, CDCl$_3$) δ 2.27 (3H, s), 6.13 (1H, brs), 6.82 (2H, d, J=8.4 Hz), 7.05 (2H, d, J=8.8 Hz), 7.20 (2H, d, J=8.4 Hz), 7.22 (2H, d, J=8.8 Hz), 7.46 (1H, brs), 12.66 (1H, brs).

SYNTHETIC EXAMPLE 5

Synthesis of N-(6-chloro-3-pyridylmethyl)-2-[N-ethoxymethyl-N-(4-trifluoromethylphenyl hydrazono) propionic acid amide (Compound No. 127)

60% sodium hydride (0.060 g, 1.5 mmol) was added to a solution of N-(6-chloro-3-pyridylmethyl)-2-(4-trifluoromethylphenyl hydrazono) propionic acid amide (0.4 g, 1 mmol) in N,N-dimethylformamide (3 ml) and stirred for 10 minutes. Ethoxy methyl chloride (0.14 g, 1.5 mmol) was added thereto, and stirred at room temperature for 1 hour. The reaction mixture was purified with a silica gel chromatography to obtain N-(6-chloro-3-pyridylmethyl)-2-[N-ethoxymethyl-N-(4-trifluoromethylphenyl hydrazono) propionic acid amide (Compound No. 127) (0.24 g, 0.56 mmol, 56%).

Compound No. 127: mp 90–91° C.; $^1$H NMR (400 MHz, CDCl$_3$) δ 1.21 (3H, t), 1.96 (3H, s), 3.55 (2H, q), 4.55 (2H, d), 5.01 (2H, s), 7.04 (2H, d), 7.32 (1H, d), 7.55 (2H, d), 7.68 (2H, dd), 8.38 (1H, s).

SYNTHETIC EXAMPLE 6

Synthesis of N-(4-chlorobenzyl)-2-[N-methyl-N-(4-trifluoromethylphenyl) hydrazono]propionic acid amide (Compound No. 109)

A mixture of ethyl pyruvate (3.3 g, 28 mmol), 4-trifluoromethylphenyl hydrazine (5.0 g, 28 mmol) and ethanol (50 ml) was refluxed under heating for 5 hours. After cooling to room temperature, the solvent was distilled off, and ethyl acetate and water were added to the residue, and then the mixture was subjected to extraction. The organic phase was washed with a saturated brine, and then dried on anhydrous sodium sulfate. Filtration and next concentration gave crude ethyl 2-(4-trifluoromethylphenyl hydrazono) propionate (4.7 g, 17 mmol, 61%).

$^1$H NMR (400 MHz, CDCl$_3$) δ 1.39 (3H, t), 2.14 (3H, s), 4.33 (2H, q), 7.27 (2H, d), 7.55 (2H, d), 7.78 (1H, s).

60% sodium hydride (0.2 g, 5 mmol) was gradually added to a solution of ethyl 2-(4-trifluoromethylphenyl hydrazono) propionate (1.37 g, 5.00 mmol) in tetrahydrofuran (10 ml) and stirred for 30 minutes. Methyl iodide (0.85 g, 5.0 mmol) was gradually added, and stirred further for 1 hour. The solvent was distilled off, and ethyl acetate and water were added to the residue, and then the mixture was subjected to extraction. The organic phase was washed with a saturated brine, and then dried on anhydrous sodium sulfate. After filtrating and then concentrating, the residue was purified with a silica gel chromatography to obtain ethyl 2-[N-methyl-N-(4-trifluoromethylphenyl) hydrazono]propionate (1.0 g, 3.6 mmol, 72%).

mp 71–72° C.; $^1$H NMR (400 MHz, CDCl$_3$) δ 1.40 (3H, t), 2.22 (3H, s), 3.40 (3H, s), 4.36 (2H, q), 7.18 (2H, d), 7.54 (2H, d).

Ethyl 2-[N-methyl-N-(4-trifluoromethylphenyl) hydrazono]propionate (0.94 g, 3.3 mmol) was dissolved in tetrahydrofuran (10 ml), 1N aqueous solution of sodium hydroxide (6.5 ml, 6.6 mmol) was added thereto, and the resulting mixture was left at room temperature overnight. When the mixture was acidified with 1N hydrochloric acid, crystals were separated out. The crystals were dissolved in ethyl acetate and extracted therewith. The organic phase was washed with a saturated brine, and then dried on anhydrous sodium sulfate. Filtration and next concentration gave 2-[N-methyl-N-(4-trifluoromethylphenyl hydrazono) propionic acid (0.6 g, 2.4 mmol, 72%). mp 53–54° C.; $^1$H NMR (400 MHz, CDCl$_3$) δ 2.49 (3H, s), 3.54 (3H, s), 7.17 (2H, d), 7.61 (2H, d).

A mixture of 2-[N-methyl-N-(4-trifluoromethylphenyl hydrazono) propionic acid (0.59 g, 2.3 mmol), 4-chlorobenzyl amine (0.33 g, 2.3 mmol), 1-[3-(dimethylamino) propyl]-3-ethylcarbodiimide hydrochloric acid salt (0.44 g, 2.3 mmol) and dichloromethane (10 ml) was left at room temperature overnight. The mixture was extracted with chloroform, washed 1N hydrochloric acid, a saturated sodium bicarbonate water and a saturated brine, dried on sodium sulfate and then filtered. The residue obtained by concentrating the resulting filtrate was purified with a silica gel chromatography to obtain N-(4-chlorobenzyl)-2-[N-methyl-N-(4-trifluoromethylphenyl) hydrazono]propionic acid amide (Compound No. 109) (0.30 g, 0.78 mmol, 34%).

Compound No. 109: mp 112–113° C.; $^1$H NMR (400 MHz, CDCl$_3$) δ 2.24 (3H, s), 3.31 (3H, s), 4.53 (2H, d), 7.02 (2H, d), 7.30 (4H, m), 7.54 (2H, d).

SYNTHETIC EXAMPLE 7

Synthesis of N-(6-chloro-3-pyridylmethyl)-2-[N-methyl-N-(4-trifluoromethylphenyl) hydrazono]propionic acid amide (Compound No. 110)

60% sodium hydride (0.12 g, 3.0 mmol) was added to a solution of N-(6-chloro-3-pyridylmethyl)-2-(4-trifluoromethylphenyl hydrazono) propionic acid amide (Compound No. 63) (1.0 g, 2.7 mmol) in N,N-dimethylformamide (5 ml) and stirred for 10 minutes. Methyl iodide (0.40 g, 2.8 mmol) was gradually added thereto, and stirred at room temperature for 2 hours. To the reaction mixture, ice water and ethyl acetate were added, and subjected to extraction. The organic phase was washed with a saturated brine, then dried on anhydrous sodium sulfate and concentrated. The resulting residue was purified with a silica gel chromatography to obtain N-(6-chloro-3-pyridylmethyl)-2-[N-methyl-N-(4-trifluoromethylphenyl) hydrazono]propionic acid amide (Compound No. 110) (0.80 g, 2.1 mmol, 77%).

Compound No. 110: mp 141–142° C.; $^1$H NMR (400 MHz, CDCl$_3$) δ 2.23 (3H, s), 3.32 (3H, s), 4.55 (2H, d), 7.03 (2H, d), 7.31 (1H, d), 7.55 (2H, d), 7.60 (1H, brs), 7.67 (2H, dd), 8.37 (1H, s).

SYNTHETIC EXAMPLE 8

Synthesis of N-(6-chloro-3-pyridylmethyl)-3-ethoxy-2-(4-trifluoromethylphenyl hydrazono) propionic acid amide (Compound No. 170)

4-Trifluoromethylphenyl hydrazine (1.76 g, 10.0 mmol) was gradually added to a mixture of ethyl bromopyruvate (1.95 g, 10.0 mmol) and ethanol (2 ml) under cooling with water. The mixture was stirred at room temperature for 1 hour. The resulting solution was added dropwise under cooling with water to a solution obtained by gradually adding 60% sodium hydride (0.4 g, 10.0 mmol) to ethanol (20 ml). The resulting mixture was left at room temperature overnight, then the solvent was distilled off, and ethyl acetate and water were added to the residue, and then the mixture was subjected to extraction. The organic phase was washed with a saturated brine, and then dried on anhydrous sodium sulfate. After filtrating and then concentrating, the residue was purified with silica gel chromatography to obtain ethyl 3-ethoxy-2-(4-trifluoromethylphenyl hydrazono) propionate (0.57 g, 1.8 mmol, 18%).

$n_D^{25}$ 1.5250; $^1$H NMR (400 MHz, CDCl$_3$) δ 1.24 (3H, t), 1.38 (3H, t), 3.59 (2H, q), 4.32 (4H, m), 7.27 (2H, d), 7.54 (2H, d), 12.38 (1H, s).

Ethyl 3-ethoxy-2-(4-trifluoromethylphenyl hydrazono) propionate (0.5 g, 1.6 mmol) was dissolved in tetrahydrofuran (2 ml), 1N aqueous solution of sodium hydroxide (3.2 ml, 3.2 mmol) was added thereto, and the resulting mixture was left at room temperature overnight. The mixture was acidified with 1N hydrochloric acid, and then subjected to extraction by adding ethyl acetate and water. The organic phase was washed with a saturated brine, and then dried on anhydrous sodium sulfate. Filtration and next concentration gave 3-ethoxy-2-(4-trifluoromethylphenyl hydrazono) propionic acid (0.3 g, 1.0 mmol, 65%).

mp 96–99° C.; $^1$H NMR (400 MHz, CDCl$_3$) δ 1.31 (3H, t), 3.70 (2H, q), 4.46 (2H, s), 7.28 (2H, d), 7.56 (2H, d), 12.42 (1H, s).

A mixture of 3-ethoxy-2-(4-trifluoromethylphenyl hydrazono) propionic acid (0.3 g, 1 mmol), 5-aminomethyl-2-chloropyridine (0.21 g, 1.5 mmol), 1-[3-(dimethylamino) propyl]-3-ethylcarbodiimide hydrochloric acid salt (0.29 g, 1.5 mmol) and chloroform (10 ml) was left at room temperature overnight. The mixture was extracted with chloroform, washed 1N hydrochloric acid, a saturated sodium bicarbonate water and a saturated brine, dried on anhydrous sodium sulfate and then filtered. The residue obtained by concentrating the resulting filtrate was purified with a silica gel chromatography to obtain N-(6-chloro-3-pyridylmethyl)-3-ethoxy-2-(4-trifluoromethylphenyl hydrazono) propionic acid amide (Compound No. 170) (0.3 g, 0.72 mmol, 72%).

Compound No. 170: mp 98–99° C.; $^1$H NMR (400 MHz, CDCl$_3$) δ 1.20 (3H, t), 3.57 (2H, q), 4.36 (2H, s), 4.51 (2H, d), 6.22 (2H, d), 7.33 (1H, d), 7.37 (1H, d), 7.52 (2H, d), 7.52 (2H, d), 7.64 (1H, dd), 7.85 (1H, brt).

SYNTHETIC EXAMPLE 9

Synthesis of N-(6-chloro-3-pyridylmethyl)-2-chloro-2-(4-trifluoromethylphenyl hydrazono) acetic acid amide (Compound No. 5)

4-Trifluoromethylphenyl hydrazine (4.1 g, 23 mmol) was gradually added to a solution of concentrated hydrochloric acid (5 ml) in water (120 ml). 40% aqueous solution (4.3 g, 23 mmol) of glyoxylic acid was gradually added, and stirred at room temperature for 5 hours. After leaving it overnight, the mixture was extracted with ethyl acetate. The organic phase was washed with a saturated brine, and dried on anhydrous sodium sulfate. The solvent was distilled off, and the resulting crystals were washed with hexane and a little amount of ethyl acetate to obtain (4-trifluoromethylphenyl hydrazono) acetic acid (4.7 g, 20 mmol, 88%).

mp 125° C.; $^1$H NMR (400 MHz, DMSO-d$_6$) δ 7.21 (1H, s), 7.25 (2H, d), 7.62 (2H, d), 11.45 (1H, s), 12.55 (1H, s).

(4-Trifluoromethylphenyl hydrazono) acetic acid (2.3 g, 10 mmol), 5-aminomethyl-2-chloropyridine (1.4 g, 10 mmol) and 1-[3-(dimethylamino) propyl]-3-ethylcarbodiimide hydrochloric acid salt were added to dichloromethane (30 ml), and stirred at room temperature for 8 hours. After leaving it overnight, 1N hydrochloric acid and chloroform were added thereto, but they were not dissolved therein, and then crystals were filtered off. The resulting crystals were dried to obtain N-(6-chloro-3-pyridylmethyl)-4-trifluoromethylphenylhydrazono acetic acid amide (2.1 g, 5.9 mmol). Further, the filtrate was subjected to extraction, the organic phase was washed with a saturated brine and then dried on anhydrous sodium sulfate. The solvent was distilled off, and the resulting crystals were washed with hexane and a little amount of ethyl acetate to obtain N-(6-chloro-3-pyridylmethyl)-4-trifluoromethylphenyl hydrazono acetic acid amide (0.4 g, 1.1 mmol, 70%).

$^1$H NMR (400 MHz, DMSO-d$_6$) δ 4.41 (2H, d), 7.22 (1H, s), 7.34 (2H, d), 7.49 (1H, d), 7.58 (2H, d), 7.77 (1H, dd), 8.36 (1H, d), 8.81 (1H, t).

N-chlorosuccinimide (0.53 g, 4.0 mmol) was added to a solution of N-(6-chloro-3-pyridylmethyl)-4-trifluoromethylphenyl hydrazono acetic acid amide in N,N-dimethylformamide (6 ml), and left at room temperature overnight. To the reaction mixture, ice water and ethyl acetate were added, and subjected to extraction. The organic phase was washed with an aqueous solution of sodium thiosulfate and a saturated brine, then dried on anhydrous sodium sulfate. After concentrating it, hexan and a little amount of ethyl acetate were added thereto, and the resulting crystals were washed and filtered to obtain N-(6-chloro-3-pyridylmethyl)-2-chloro-2-(4-trifluoromethylphenyl hydrazono) acetic acid amide (Compound No. 5) (1.15 g, 2.95 mmol, 82%).

Compound No. 5: mp 172–173° C.; $^1$H NMR (400 MHz, CDCl$_3$) δ 4.61 (2H, d), 7.10 (1H, brs), 7.20 (2H, d), 7.33 (1H, d), 7.58 (2H, d), 7.70 (1H, dd), 8.33 (1H, s), 8.38 (1H, d).

SYNTHETIC EXAMPLE 10

Synthesis of N-(6-chloro-3-pyridylmethyl)-2-methylamino-2-(4-trifluoromethylphenyl) hydrazono]acetic acid amide (Compound No. 191)

40% aqueous solution of methylamine (78 mg, 1.0 mmol) was gradually added to a solution of N-(6-chloro-3-pyridylmethyl)-2-chloro-2-(4-trifluoromethylphenyl hydrazono) acetic acid amide (Compound No. 5) (0.4 g, 1 mmol) and triethylamine (0.1 g, 1 mmol) in tetrahydrofuran (10 ml) and left at room temperature overnight. Further, 40% aqueous solution of methylamine (10 mg, 0.13 mmol) was added and stirred at room temperature for 1 hour, and thereafter subjected to extraction by adding ethyl acetate and water. The organic phase was washed with a saturated brine, and then dried on anhydrous sodium sulfate. The resulting residue was purified with a silica gel chromatography to obtain N-(6-chloro-3-pyridylmethyl)-2-methylamino-2-(4-trifluoromethylphenyl hydrazono) acetic acid amide (Compound No. 191) (0.13 g, 0.34 mmol, 34%).

Compound No. 191: mp 156° C.; $^1$H NMR (400 MHz, CDCl$_3$) δ 2.96 (3H, d), 4.54 (2H, d), 5.11 (1H, brd), 7.05 (2H, d), 7.13 (1H, s), 7.32 (1H, d), 7.50 (2H, d), 7.65 (1H, dd), 8.37 (1H, d).

SYNTHETIC EXAMPLE 11

Synthesis of N-(6-chloro-3-pyridylmethyl)-2-cyano-2-(4-trifluoromethylphenyl hydrazono) acetic acid amide (Compounds No. 184 and 185)

Cyanoacetic acid (2.6 g, 0.030 mmol), 5-aminomethyl-2-chloropyridine (4.3 g, 0.030 mmol) and 1-[3-(dimethylamino) propyl]-3-ethylcarbodiimide hydrochloric acid salt (5.8 g, 0.030 mol) were added to dichloromethane (50 ml), and stirred overnight. Chloroform and 1N hydrochloric acid were added thereto, and crystals were separated out. The crystals were filtered off, dissolved in ethyl acetate, and water was added thereto and subjected to extraction. The organic phase was washed with a saturated sodium bicarbonate and a saturated brine, and then dried anhydrous sodium sulfate. The residue obtained by filtrating and concentrating was washed with hexane and a little amount of ethyl acetate to obtain N-(6-chloro-3-pyridylmethyl)-2-cyanoacetic acid amide (6.1 g, 0.029 mmol, 97%).

mp 119° C.; $^1$H NMR (400 MHz, DMSO-d$_6$) δ 3.72 (2H, s), 4.32 (2H, d), 7.50 (1H, d), 7.75 (1H, dd), 8.33 (1H, d), 8.80 (1H, brs).

4-Trifluoromethyl aniline (0.97 g, 6.0 mmol) was gradually added to acetic acid (3.5 ml), water (1.7 ml) and concentrated hydrochloric acid (1.7 ml) and dissolved, and cooled to 5° C. A solution of sodium nitrate (0.5 g, 7.2 mmol) in water (2 ml) was gradually added thereto at a temperature of 10° C. or less. The resulting solution was gradually added to a mixture of N-(6-chloro-3-pyridylmethyl)-2-cyanoacetic acid amide (1.3 g, 6.0 mmol), sodium acetate (1.23 g, 15.0 mmol), ethanol (30 ml) and 1N aqueous solution of sodium carbonate (40 ml). After stirring at room temperature for 5 hours, water and ethyl acetate were added thereto and subjected to extraction. The organic phase was washed with a saturated brine, and dried on anhydrous sodium sulfate. The residue obtained by filtering and concentrating was purified with a silica gel chromatography to obtain N-(6-chloro-3-pyridylmethyl)-2-cyano-2-(4-trifluoromethylphenyl hydrazono) acetic acid amide (Compound No. 184) (0.12 g, 0.30 mmol, 5%) (Compound No. 185) (1.15 g, 3.00 mmol, 50%). Geometrical isomerism (E/Z) was not determined.

Compound No. 184: mp 204–205° C.; $^1$H NMR (400 MHz, DMSO-d$_6$) δ 4.43 (2H, d), 7.53 (1H, d), 7.63 (2H, d), 7.74 (2H, d), 7.85 (1H, dd), 8.43 (1H, d), 9.23 (1H, t).

Compound No. 185: mp 205–206° C.; $^1$H NMR (400 MHz, DMSO-d$_6$) δ 4.46 (2H, d), 7.50 (1H, d), 7.72 (2H, d), 7.82 (3H, m), 8.39 (1H, d), 9.04 (1H, t), 12.04 (1H, s).

SYNTHETIC EXAMPLE 12

Compounds listed in the Tables 1 to 8 below were synthesized in a similar manner as the above-mentioned Synthetic Examples 1 to 11.

TABLE 1

| No. | U | V$^1$ | V$^2$ | W | X$^1$ | X$^2$ | Z | E/Z |
|---|---|---|---|---|---|---|---|---|
| 1 | CH | 4-Cl | 4-Cl | CH$_2$ | H | H | H | E |
| 2 | CH | 4-CF$_3$ | 4-Cl | CH$_2$ | H | H | H | E |
| 3 | N | 4-Cl | 3-CF$_3$ | CH$_2$ | CH$_2$C$_6$H$_5$-4-CN | H | H | E |
| 4 | CH | 4-Cl | 4-Cl | CH$_2$ | H | H | Cl | E |
| 5 | N | 4-Cl | 4-CF$_3$ | CH$_2$ | H | H | Cl | E |
| 6 | CH | H | H | CH$_2$ | H | H | Me | E |
| 7 | CH | H | 4-Cl | CH$_2$ | H | H | Me | E |
| 8 | CH | H | 4-CF$_3$ | CH$_2$ | H | H | Me | E |
| 9 | N | H | 4-CF$_3$ | CH$_2$ | H | H | Me | E |
| 10 | CH | 3-F | 4-Cl | CH$_2$ | H | H | Me | E |
| 11 | CH | 3,4-F | 4-Cl | CH$_2$ | H | H | Me | E |
| 12 | CH | 3,4-F | 4-CF$_3$ | CH$_2$ | H | H | Me | E |
| 13 | CH | 4-F | 4-Cl | CH$_2$ | H | H | Me | E |
| 14 | CH | 4-F | 2,4-Cl | CH$_2$ | H | H | Me | E |
| 15 | CH | 4-F | 4-Br | CH$_2$ | H | H | Me | E |
| 16 | CH | 4-F | 4-CF$_3$ | CH$_2$ | H | H | Me | E |
| 17 | N | 4-F | 4-CF$_3$ | CH$_2$ | H | H | Me | E |
| 18 | CH | 2-Cl | 4-Cl | CH$_2$ | H | H | Me | E |
| 19 | CH | 2,4-Cl | 4-CF$_3$ | CH$_2$ | H | H | Me | E |
| 20 | CH | 3-Cl | 4-Cl | CH$_2$ | H | H | Me | E |
| 21 | CH | 3-Cl | 4-Br | CH$_2$ | H | H | Me | E |

TABLE 1-continued

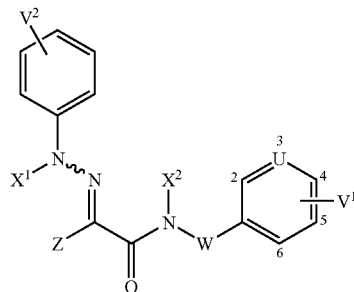

| No. | U | V¹ | V² | W | X¹ | X² | Z | E/Z |
|---|---|---|---|---|---|---|---|---|
| 22 | CH | 3,4-Cl | 4-CF$_3$ | CH$_2$ | H | H | Me | E |
| 23 | CH | 3,5-Cl | 4-CF$_3$ | CH$_2$ | H | H | Me | E |
| 24 | CH | 4-Cl | 2,5-F | CH$_2$ | H | H | Me | E |
| 25 | CH | 4-Cl | 3-F | CH$_2$ | H | H | Me | E |
| 26 | CH | 4-Cl | 3,4,5-F | CH$_2$ | H | H | Me | E |
| 27 | N | 4-Cl | 3,4,5-F | CH$_2$ | H | H | Me | E |
| 28 | CH | 4-Cl | 3,5-F | CH$_2$ | H | H | Me | E |
| 29 | N | 4-Cl | 3,5-F | CH$_2$ | H | H | Me | E |
| 30 | CH | 4-Cl | 3-F-4-CF$_3$ | CH$_2$ | H | H | Me | E |
| 31 | N | 4-Cl | 3-F-4-CF$_3$ | CH$_2$ | H | H | Me | E |
| 32 | CH | 4-Cl | 4-F | CH$_2$ | H | H | Me | E |
| 33 | N | 4-Cl | 4-F | CH$_2$ | H | H | Me | E |
| 34 | CH | 4-Cl | 3-CF$_3$-4-F | CH$_2$ | H | H | Me | E |
| 35 | N | 4-Cl | 3-CF$_3$-4-F | CH$_2$ | H | H | Me | E |
| 36 | CH | 4-Cl | 2-Cl | CH$_2$ | H | H | Me | E |
| 37 | N | 4-Cl | 2,4-Cl | CH$_2$ | H | H | Me | E |
| 38 | CH | 4-Cl | 3-Cl-4-CF$_3$ | CH$_2$ | H | H | Me | E |
| 39 | N | 4-Cl | 3-Cl-4-CF$_3$ | CH$_2$ | H | H | Me | E |
| 40 | CH | 4-Cl | 2,6-Cl-4-CF$_3$ | CH$_2$ | H | H | Me | E |
| 41 | N | 4-Cl | 2,6-Cl-4-CF$_3$ | CH$_2$ | H | H | Me | E |
| 42 | CH | 4-Cl | 3-Cl | CH$_2$ | H | H | Me | E |
| 43 | CH | 4-Cl | 3,4-Cl | CH$_2$ | H | H | Me | E,Z |
| 44 | N | 4-Cl | 3,4-Cl | CH$_2$ | H | H | Me | E |
| 45 | CH | 4-Cl | 3,4,5-Cl | CH$_2$ | H | H | Me | E |
| 46 | CH | 4-Cl | 3,4,5-Cl | CH$_2$ | H | H | Me | Z |
| 47 | N | 4-Cl | 3,4,5-Cl | CH$_2$ | H | H | Me | E |
| 48 | CH | 4-Cl | 3,5-Cl | CH$_2$ | H | H | Me | E |
| 49 | CH | 4-Cl | 4-Cl | CH$_2$ | H | H | Me | E |
| 50 | N | 4-Cl | 4-Cl | CH$_2$ | H | H | Me | E |
| 51 | CH | 4-Cl | 3-Br | CH$_2$ | H | H | Me | E |
| 52 | CH | 4-Cl | 4-Br | CH$_2$ | H | H | Me | E |
| 53 | N | 4-Cl | 4-Br | CH$_2$ | H | H | Me | E |
| 54 | CH | 4-Cl | 4-CN | CH$_2$ | H | H | Me | E |
| 55 | CH | 4-Cl | 4-Me | CH$_2$ | H | H | Me | E |
| 56 | CH | 4-Cl | 4-Et | CH$_2$ | H | H | Me | E |
| 57 | CH | 4-Cl | 4-t-Bu | CH$_2$ | H | H | Me | E |
| 58 | CH | 4-Cl | 2-CF$_3$ | CH$_2$ | H | H | Me | E |
| 59 | CH | 4-Cl | 3-CF$_3$ | CH$_2$ | H | H | Me | E |
| 60 | N | 4-Cl | 3-CF$_3$ | CH$_2$ | H | H | Me | E |
| 61 | N | 4-Cl | 3,5-CF$_3$ | CH$_2$ | H | H | Me | E |
| 62 | CH | 4-Cl | 4-CF$_3$ | CH$_2$ | H | H | Me | E |
| 63 | N | 4-Cl | 4-CF$_3$ | CH$_2$ | H | H | Me | E |
| 64 | CH | 4-Cl | 4-OCF$_3$ | CH$_2$ | H | H | Me | E |
| 65 | N | 4-Cl | 4-OCF$_3$ | CH$_2$ | H | H | Me | E |
| 66 | CH | 4-Cl | 4-SCF$_3$ | CH$_2$ | H | H | Me | E |
| 67 | CH | 4-Cl | 4-SCF$_3$ | CH$_2$ | H | H | Me | Z |
| 68 | N | 4-Cl | 4-SCF$_3$ | CH$_2$ | H | H | Me | E,Z |
| 69 | N | 4,5-Cl | 4-CF$_3$ | CH$_2$ | H | H | Me | E |
| 70 | CH | 4-Br | 3,4-Cl | CH$_2$ | H | H | Me | E |
| 71 | CH | 4-Br | 4-Cl | CH$_2$ | H | H | Me | E |
| 72 | CH | 4-Br | 4-Br | CH$_2$ | H | H | Me | E |
| 73 | CH | 4-Br | 4-CF$_3$ | CH$_2$ | H | H | Me | E |
| 74 | N | 4-Br | 4-CF$_3$ | CH$_2$ | H | H | Me | E |
| 75 | N | 5-Br | 4-CF$_3$ | CH$_2$ | H | H | Me | E |
| 76 | CH | 2,3-Me | 4-Cl | CH$_2$ | H | H | Me | E |
| 77 | CH | 2,3-Me | 4-Et | CH$_2$ | H | H | Me | E |
| 78 | CH | 4-Me | 4-Cl | CH$_2$ | H | H | Me | E |
| 79 | N | 4-Me | 4-CF$_3$ | CH$_2$ | H | H | Me | E |
| 80 | CH | 4-Et | 3,5-Me | CH$_2$ | H | H | Me | E |
| 81 | CH | 4-Et | 4-Cl | CH$_2$ | H | H | Me | E |

TABLE 1-continued

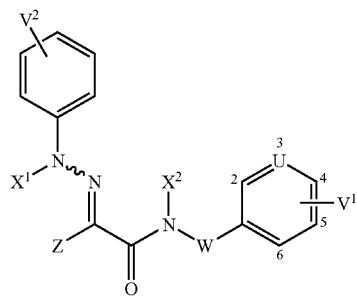

| No. | U | V¹ | V² | W | X¹ | X² | Z | E/Z |
|---|---|---|---|---|---|---|---|---|
| 82 | N | 4-Et | 4-CF₃ | CH₂ | H | H | Me | E |
| 83 | CH | 4-Pr | 4-Cl | CH₂ | H | H | Me | E |
| 84 | CH | 4-Pr | 4-Et | CH₂ | H | H | Me | E |
| 85 | N | 4-Bu | 4-CF₃ | CH₂ | H | H | Me | E |
| 86 | CH | 4-t-Bu | 4-Cl | CH₂ | H | H | Me | E |
| 87 | CH | 3-CF₃ | 4-Cl | CH₂ | H | H | Me | E |
| 88 | CH | 3,5-CF₃ | 4-Cl | CH₂ | H | H | Me | E |
| 89 | CH | 4-CF₃ | 3,4-Cl | CH₂ | H | H | Me | E |
| 90 | CH | 4-CF₃ | 4-Cl | CH₂ | H | H | Me | E |
| 91 | CH | 4-CF₃ | 4-CF₃ | CH₂ | H | H | Me | E |
| 92 | N | 4-CF₃ | 4-CF₃ | CH₂ | H | H | Me | E |
| 93 | CH | 4-OMe | 4-Cl | CH₂ | H | H | Me | E |
| 94 | N | 4-OMe | 4-CF₃ | CH₂ | H | H | Me | E |
| 95 | N | 4-OEt | 4-CF₃ | CH₂ | H | H | Me | E |
| 96 | CH | 4-OCF₃ | 4-CF₃ | CH₂ | H | H | Me | E |
| 97 | N | 4-NMe₂ | 4-CF₃ | CH₂ | H | H | Me | E |
| 98 | N | 4-NHMe | 4-CF₃ | CH₂ | H | H | Me | E |
| 99 | CH | 4-SCF₃ | 4-CF₃ | CH₂ | H | H | Me | E |
| 100 | CH | 4-Cl | 4-Cl | CHMe | H | H | Me | E |
| 101 | CH | 4-Cl | 4-Cl | CH₂CH₂ | H | H | Me | E |
| 102 | CH | 4-Cl | H | NH | H | H | Me | E |
| 103 | CH | 4-Cl | 4-Me | NH | H | H | Me | E |
| 104 | CH | 4-Cl | 4-Cl | NH | H | H | Me | E |
| 105 | CH | 4-Cl | 4-Cl | NH | H | H | Me | Z |
| 106 | N | 4-Cl | 4-CF₃ | NH | H | H | Me | E |
| 107 | CH | 4-CF₃ | 4-Cl | O | H | H | Me | E |
| 108 | CH | 4-CF₃ | 4-CF₃ | O | H | H | Me | E |
| 109 | CH | 4-Cl | 4-CF₃ | CH₂ | Me | H | Me | E |
| 110 | N | 4-Cl | 4-CF₃ | CH₂ | Me | H | Me | E |
| 111 | N | 4-Cl | 4-CF₃ | CH₂ | Me | Me | Me | E,Z |
| 112 | N | 4-Cl | 4-CF₃ | CH₂ | Me | CO₂Me | Me | E |
| 113 | N | 4-Cl | 4-CF₃ | CH₂ | Et | H | Me | E |
| 114 | N | 4-Cl | 4-CF₃ | CH₂ | Pr | H | Me | E |
| 115 | N | 4-Cl | 4-CF₃ | CH₂ | i-Pr | H | Me | E |
| 116 | N | 4-Cl | 4-CF₃ | CH₂ | Bu | H | Me | E |
| 117 | N | 4-Cl | 4-CF₃ | CH₂ | CH₂c-Pr | H | Me | E |
| 118 | N | 4-Cl | 4-CF₃ | CH₂ | i-Bu | H | Me | E |
| 119 | N | 4-Cl | 4-CF₃ | CH₂ | s-Bu | H | Me | E |
| 120 | N | 4-Cl | 4-CF₃ | CH₂ | CH₂CH=CH₂ | H | Me | E |
| 121 | N | 4-Cl | 4-CF₃ | CH₂ | CH₂CH(Me)=CH₂ | H | Me | E |
| 122 | N | 4-Cl | 4-CF₃ | CH₂ | CH₂CN | H | Me | E |
| 123 | N | 4-Cl | 4-CF₃ | CH₂ | CH₂CH₂F | H | Me | E |
| 124 | N | 4-Cl | 4-CF₃ | CH₂ | CH₂CF₃ | H | Me | E |
| 125 | N | 4-Cl | 4-CF₃ | CH₂ | CH₂OMe | H | Me | E |
| 126 | CH | 4-Cl | 4-CF₃ | CH₂ | CH₂OEt | H | Me | E |
| 127 | N | 4-Cl | 4-CF₃ | CH₂ | CH₂OEt | H | Me | E |
| 128 | N | 4-Cl | 4-CF₃ | CH₂ | CH₂Oi-Pr | H | Me | E |
| 129 | N | 4-Cl | 4-CF₃ | CH₂ | CH₂Oi-Bu | H | Me | E |
| 130 | N | 4-Cl | 4-CF₃ | CH₂ | CH₂OCH₂CH₂OMe | H | Me | E |
| 131 | N | 4-Cl | 4-CF₃ | CH₂ | CH₂CO₂Et | H | Me | E |
| 132 | N | 4-Cl | 4-CF₃ | CH₂ | Bn | H | Me | E |
| 133 | N | 4-Cl | 3-CF₃ | CH₂ | CH₂C₆H₅-4-CN | H | Me | E |
| 134 | N | 4-Cl | 4-CF₃ | CH₂ | CH₂C₆H₅-4-CN | H | Me | E |
| 135 | N | 4-Cl | 4-CF₃ | CH₂ | CH₂C₆H₅-4-Me | H | Me | E |
| 136 | N | 4-Cl | 4-CF₃ | CH₂ | COMe | H | Me | E |
| 137 | N | 4-Cl | 4-CF₃ | CH₂ | CH₂SMe | H | Me | E |
| 138 | N | 4-Cl | 4-CF₃ | CH₂ | CH₂CO₂Et | CH₂CO₂Et | Me | E |
| 139 | CH | H | 4-Cl | CH₂ | H | H | Et | E |
| 140 | CH | 4-Br | 4-Cl | CH₂ | H | H | Et | E |

TABLE 1-continued

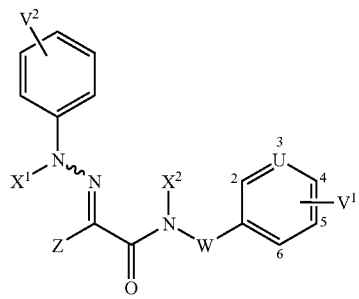

| No. | U | V¹ | V² | W | X¹ | X² | Z | E/Z |
|---|---|---|---|---|---|---|---|---|
| 141 | CH | 4-Me | 4-Cl | CH₂ | H | H | Et | E |
| 142 | CH | 4-CF₃ | 4-Cl | CH₂ | H | H | Et | Z |
| 143 | CH | 4-CF₃ | 4-Cl | CH₂ | H | H | Et | E |
| 144 | CH | 4-F | 4-CF₃ | CH₂ | H | H | Et | E |
| 145 | CH | 4-Cl | 4-CF₃ | CH₂ | H | H | Et | E |
| 146 | N | 4-Cl | 4-CF₃ | CH₂ | H | H | Et | E |
| 147 | CH | 4-CF₃ | 4-CF₃ | CH₂ | H | H | Et | E |
| 148 | CH | 4-Br | 4-Cl | CH₂CH₂ | H | H | Et | E |
| 149 | CH | H | 4-Cl | CH₂ | H | H | Pr | Z |
| 150 | CH | H | 4-Cl | CH₂ | H | H | Pr | E |
| 151 | CH | 4-Cl | 4-Cl | CH₂ | H | H | Pr | Z |
| 152 | CH | 4-Cl | 4-Cl | CH₂ | H | H | Pr | E |
| 153 | N | 4-Cl | 4-CF₃ | CH₂ | H | H | Pr | E |
| 154 | CH | 4-Me | 4-Cl | CH₂ | H | H | Pr | Z |
| 155 | CH | 4-Me | 4-Cl | CH₂ | H | H | Pr | E |
| 156 | CH | H | 4-Cl | CH₂ | H | H | i-Pr | E |
| 157 | CH | 4-Cl | 4-Cl | CH₂ | H | H | i-Pr | E |
| 158 | CH | 4-Br | 4-Cl | CH₂ | H | H | i-Pr | E |
| 159 | CH | 4-CF₃ | 4-Cl | CH₂ | H | H | i-Pr | Z |
| 160 | CH | 4-CF₃ | 4-Cl | CH₂ | H | H | i-Pr | E |
| 161 | CH | 4-Cl | 4-CF₃ | CH₂ | H | H | i-Pr | Z |
| 162 | N | 4-Cl | 4-CF₃ | CH₂ | H | H | i-Pr | Z |
| 163 | CH | H | 4-Cl | CH₂ | H | H | s-Bu | Z |
| 164 | CH | H | 4-Cl | CH₂ | H | H | s-Bu | E |
| 165 | CH | 4-Cl | 4-Cl | CH₂ | H | H | s-Bu | Z |
| 166 | CH | 4-Cl | 4-Cl | CH₂ | H | H | s-Bu | E |
| 167 | CH | 4-CF₃ | 4-Cl | CH₂ | H | H | s-Bu | Z |
| 168 | CH | 4-CF₃ | 4-Cl | CH₂ | H | H | s-Bu | E |
| 169 | CH | 4-CF₃ | 4-CF₃ | NH | H | H | CF₃ | E |
| 170 | N | 4-Cl | 4-CF₃ | CH₂ | H | H | CH₂OEt | E |
| 171 | N | 4-Cl | 4-CF₃ | CH₂ | H | H | CH₂SMe | E |
| 172 | CH | H | 4-Cl | CH₂ | H | H | CN | |
| 173 | CH | H | 4-Cl | CH₂ | H | H | CN | |
| 174 | CH | H | 4-CF₃ | CH₂ | H | H | CN | |
| 175 | CH | H | 4-CF₃ | CH₂ | H | H | CN | |
| 176 | CH | 4-Cl | 4-Cl | CH₂ | H | H | CN | |
| 177 | CH | 4-Cl | 4-Cl | CH₂ | H | H | CN | |
| 178 | CH | 4-Cl | 4-Br | CH₂ | H | H | CN | |
| 179 | N | 4-Cl | 4-CN | CH₂ | H | H | CN | |
| 180 | CH | 4-Cl | 4-Me | CH₂ | H | H | CN | |
| 181 | CH | 4-Cl | 4-Me | CH₂ | H | H | CN | |
| 182 | CH | 4-Cl | 4-CF₃ | CH₂ | H | H | CN | |
| 183 | CH | 4-Cl | 4-CF₃ | CH₂ | H | H | CN | |
| 184 | N | 4-Cl | 4-CF₃ | CH₂ | H | H | CN | |
| 185 | N | 4-Cl | 4-CF₃ | CH₂ | H | H | CN | |
| 186 | N | 4-Cl | 4-NO₂ | CH₂ | H | H | CN | |
| 187 | CH | 4-CF₃ | 4-Cl | CH₂ | H | H | CN | |
| 188 | CH | 4-CF₃ | 4-Cl | CH₂ | H | H | CN | |
| 189 | CH | 4-CF₃ | 4-CF₃ | CH₂ | H | H | CN | |
| 190 | CH | 4-CF₃ | 4-CF₃ | CH₂ | H | H | CN | |
| 191 | N | 4-Cl | 4-CF₃ | CH₂ | H | H | NHMe | E |
| 192 | N | 4-Cl | 4-CF₃ | CH₂ | H | H | NMe₂ | E |

In case where Z is CN, geometrical isomerism (E/Z) was not determined.

TABLE 2

| No. | A | U | X¹ |
|---|---|---|---|
| 193 | 2-pyridyl | CH | H |
| 194 | 6-chloropyridin-3-yl | CH | H |
| 195 | 6-chloropyridin-3-yl | N | H |
| 196 | 5-trifluoromethylpyridin-2-yl | CH | H |
| 197 | 5-trifluoromethylpyridin-2-yl | N | H |
| 198 | 4-trifluoromethylpyrimidin-2-yl | CH | H |
| 199 | 5-trifluoromethylpyridin-2-yl | N | Me |
| 200 | 5-trifluoromethylpyridin-2-yl | CH | Me |

TABLE 3

| No. | Q | W | Z |
|---|---|---|---|
| 201 | 2-naphthyl | CH₂ | Me |
| 202 | 2-furyl | CH₂ | Me |
| 203 | 5-methylfuran-2-yl | CH₂ | Me |
| 204 | tetrahydrofuran-2-yl | CH₂ | Me |
| 205 | tetrahydrofuran-3-yl | CH₂ | Me |
| 206 | 5-bromoisoxazol-3-yl | CH₂ | Me |
| 207 | 2-thienyl | CH₂ | Me |
| 208 | 5-chlorothiophen-2-yl | CH₂ | Me |
| 209 | 2,5-dichlorothiophen-3-yl | CH₂ | Me |
| 210 | 4-bromothiophen-2-yl | CH₂ | Me |
| 211 | 5-bromothiophen-2-yl | CH₂ | Me |
| 212 | 2-chlorothiazol-5-yl | CH₂ | Me |
| 213 | 2-methylthiazol-4-yl | CH₂ | Me |
| 214 | 2-pyridyl | CH₂ | Me |
| 215 | 4-pyridyl | CH₂ | Me |
| 216 | 2-fluoropyridin-4-yl | CH₂ | Me |
| 217 | 2-chloropyridin-4-yl | CH₂ | Me |
| 218 | 6-chloropyridin-2-yl | CH₂ | Me |
| 219 | 2,6-dichloropyridin-4-yl | CH₂ | Me |
| 220 | 2-chloro-6-methylpyridin-4-yl | CH₂ | Me |
| 221 | 5-trifluoromethylpyridin-2-yl | NMe | Me |
| 222 | 3-chloro-5-trifluoromethylpyridin-2-yl | CH₂ | Me |
| 223 | pyrazin-2-yl | CH₂ | Et |
| 224 | 5-methylpyrazin-2-yl | CH₂ | Me |
| 225 | 2-chloropyrimidin-5-yl | CH₂ | Me |
| 226 | 6-chloropyridazin-3-yl | CH₂ | Me |

TABLE 4

| No. | U | V¹ | V² | W | X¹ | X² | Z | E/Z |
|---|---|---|---|---|---|---|---|---|
| 227 | CH | 3,4-Cl | 4-CF₃ | CH₂ | H | H | H | E |
| 228 | CH | 4-Cl | H | CH₂ | H | H | H | E |
| 229 | CH | 4-Cl | 4-Me | CH₂ | H | H | H | E |
| 230 | CH | 4-Cl | 4-CF₃ | CH₂ | H | H | H | E |
| 231 | CH | 4-Me | 4-CF₃ | CH₂ | H | H | H | E |
| 232 | CH | 3,4-Cl | 4-CF₃ | CH₂ | H | H | Cl | E |
| 233 | CH | 4-Me | 4-CF₃ | CH₂ | H | H | Cl | E |

TABLE 4-continued

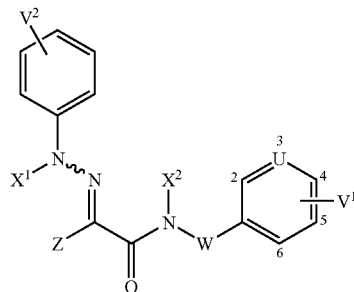

| No. | U | V¹ | V² | W | X¹ | X² | Z | E/Z |
|---|---|---|---|---|---|---|---|---|
| 234 | N | 4-Cl | 4-CF₃ | CH₂ | Me | H | Cl | E |
| 235 | CH | 3,4,5-F | 4-Cl | CH₂ | H | H | Me | E |
| 236 | CH | 3,4,5-F | 4-CF₃ | CH₂ | H | H | Me | E |
| 237 | CH | 3-F-4-Cl | 4-CF₃ | CH₂ | H | H | Me | E |
| 238 | CH | 3-Cl-4-F | 4-CF₃ | CH₂ | H | H | Me | E |
| 239 | CH | 3-OMe-4-F | 4-CF₃ | CH₂ | H | H | Me | E |
| 240 | CH | 4-Cl | 3,4-F | CH₂ | H | H | Me | E |
| 241 | N | 4-Cl | 3,4-F | CH₂ | H | H | Me | E |
| 242 | CH | 4-Cl | 3-Cl-4-F | CH₂ | H | H | Me | E |
| 243 | N | 4-Cl | 3-Cl-4-F | CH₂ | H | H | Me | E |
| 244 | CH | 4-Cl | 2,3,5,6-F-4-CF₃ | CH₂ | H | H | Me | E |
| 245 | CH | 4-Cl | 2,3,5,6-F-4-CF₃ | CH₂ | H | H | Me | Z |
| 246 | N | 4-Cl | 2,3,5,6-F-4-CF₃ | CH₂ | H | H | Me | E,Z |
| 247 | CH | 4-Cl | 3-F-5-CF₃ | CH₂ | H | H | Me | E |
| 248 | N | 4-Cl | 3-F-5-CF₃ | CH₂ | H | H | Me | E |
| 249 | N | 4-Cl | 3,5-F-4-CF₃ | CH₂ | H | H | Me | E |
| 250 | N | 4-Cl | 3-Cl-4-CF₃ | CH₂ | H | H | Me | E |
| 251 | N | 4-Cl | 3,5-Cl-4-CF₃ | CH₂ | H | H | Me | E |
| 252 | CH | 4-Cl | 3,5-CF₃-4-Cl | CH₂ | H | H | Me | E |
| 253 | CH | 4-Cl | 3,5-CF₃-4-Cl | CH₂ | H | H | Me | Z |
| 254 | N | 4-Cl | 3,5-CF₃-4-Cl | CH₂ | H | H | Me | E |
| 255 | CH | 4-Cl | 3-CF₃-4-Br | CH₂ | H | H | Me | E |
| 256 | N | 4-Cl | 3-CF₃-4-Br | CH₂ | H | H | Me | E |
| 257 | N | 4-Cl | 4-I | CH₂ | H | H | Me | E |
| 258 | N | 4-Cl | 3,4-CF₃ | CH₂ | H | H | Me | E |
| 259 | N | 4-Cl | 4-CF₃ | CH₂ | H | H | Me | Z |
| 260 | N | 4-Cl | 4-CF₂CF₃ | CH₂ | H | H | Me | E |
| 261 | N | 4-Cl | 4-(4'-CF₃—Ph) | CH₂ | H | H | Me | E |
| 262 | N | 4,5-Cl | 3-F-4-CF₃ | CH₂ | H | H | Me | E |
| 263 | N | 4,5-Cl | 3,5-F-4-CF₃ | CH₂ | H | H | Me | E |
| 264 | N | 4,5-Cl | 3,5-F-4-CF₃ | CH₂ | H | H | Me | Z |
| 265 | CH | 3,4-Br | 4-CF₃ | CH₂ | H | H | Me | E |
| 266 | CH | 3-Me-4-Br | 4-CF₃ | CH₂ | H | H | Me | E |
| 267 | CH | 3,4-Me | 4-CF₃ | CH₂ | H | H | Me | E |
| 268 | CH | 3,5-Me | 4-Et | CH₂ | H | H | Me | E |
| 269 | CH | 4-CN | 4-Cl | CH₂ | H | H | Me | E |
| 270 | CH | 4-CN | 4-CF₃ | CH₂ | H | H | Me | E |
| 271 | CH | 4-CO₂Me | 4-Cl | CH₂ | H | H | Me | E |
| 272 | CH | 4-NO₂ | 4-Cl | CH₂ | H | H | Me | E |
| 273 | CH | 3-OMe-4-OH | 4-Cl | CH₂ | H | H | Me | E |
| 274 | CH | 3,4-OMe | 4-Cl | CH₂ | H | H | Me | E |
| 275 | N | 4-OCH₂CF₃ | 4-CF₃ | CH₂ | H | H | Me | E |
| 276 | CH | 4-OPh | 4-Cl | CH₂ | H | H | Me | E |
| 277 | N | 4-OPh | 4-CF₃ | CH₂ | H | H | Me | E |
| 278 | CH | 4-O(4'-Cl—Ph) | 4-Cl | CH₂ | H | H | Me | E |
| 279 | CH | 4-O(4'-Me—Ph) | 4-Cl | CH₂ | H | H | Me | E |
| 280 | CH | 4-O(4'-CF₃—Ph) | 4-Cl | CH₂ | H | H | Me | E |
| 281 | CH | H | 4-CF₃ | CH₂CH₂O | H | H | Me | E |
| 282 | CH | 4-Cl | 4-CF₃ | CH₂CH₂O | H | H | Me | E |
| 283 | N | 4-Cl | 4-CF₃ | CH₂CH₂O | H | H | Me | E |
| 284 | CH | 4-CF₃ | 4-CF₃ | NH | H | H | Me | E |
| 285 | CH | H | 4-CF₃ | OCH₂ | H | H | Me | E |
| 286 | CH | 4-Cl | 4-CF₃ | OCH₂ | H | H | Me | E |
| 287 | CH | 3,4,5-F | 4-CF₃ | CH₂ | Me | H | Me | E |
| 288 | CH | 3-F-4-Cl | 4-CF₃ | CH₂ | Me | H | Me | E |
| 289 | N | 4-Cl | 3-F-4-CF₃ | CH₂ | Me | H | Me | E |
| 290 | N | 4-Cl | 3,5-F-4-CF₃ | CH₂ | Me | H | Me | E |
| 291 | N | 4-Cl | 4-CF₂CF₃ | CH₂ | Me | H | Me | E |
| 292 | N | 4,5-Cl | 3-F-4-CF₃ | CH₂ | Me | H | Me | E |

TABLE 4-continued

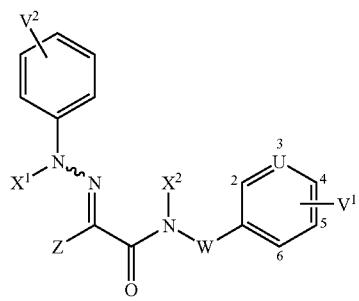

| No. | U | V¹ | V² | W | X¹ | X² | Z | E/Z |
|---|---|---|---|---|---|---|---|---|
| 293 | N | 4,5-Cl | 4-CF₃ | CH₂ | Me | H | Me | E |
| 294 | N | 4-Cl | 3-F-4-CF₃ | CH₂ | i-Pr | H | Me | E |
| 295 | N | 4,5-Cl | 3-F-4-CF₃ | CH₂ | i-Pr | H | Me | E |
| 296 | N | 4,5-Cl | 4-CF₃ | CH₂ | i-Pr | H | Me | E |
| 297 | N | 4-Cl | 4-CF₃ | CH₂ | t-BuOCO | H | Me | E |
| 298 | N | 4-Cl | 4-CF₃ | CH₂ | Me | H | Et | E |
| 299 | N | 4-Cl | 4-CF₃ | CH₂ | i-Pr | H | Et | E |
| 300 | CH | 3,4-Cl | 4-CF₃ | CH₂ | H | H | CN | |
| 301 | N | 4-Cl | 3-F-4-CF₃ | CH₂ | H | H | CN | |
| 302 | CH | 4-Me | 4-CF₃ | CH₂ | H | H | CN | |
| 303 | CH | 4-CN | 4-CF₃ | CH₂ | H | H | CN | |
| 304 | CH | 3,4-Cl | 4-CF₃ | CH₂ | H | H | NHMe | E |
| 305 | CH | 4-Cl | H | CH₂ | H | H | NHMe | E |
| 306 | CH | 4-Cl | 4-Me | CH₂ | H | H | NHMe | E |
| 307 | CH | 4-Cl | 4-CF₃ | CH₂ | H | H | NHMe | E |
| 308 | CH | 4-Me | 4-CF₃ | CH₂ | H | H | NHMe | E |
| 309 | N | 4-Cl | 4-CF₃ | CH₂ | Me | H | NHMe | E |
| 310 | N | 4-Cl | 4-CF₃ | CH₂ | H | H | N(CH₂CH₂)₂CH₂ | E |
| 311 | N | 4-Cl | 4-CF₃ | CH₂ | H | H | N(CH₂CH₂)₂O | E |

In case where Z is CN, geometrical isomerism (E/Z) was not determined.

TABLE 5

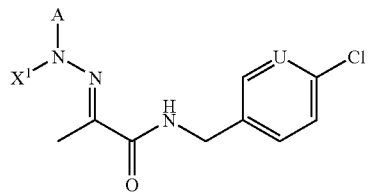

| No. | A | U | X¹ |
|---|---|---|---|
| 312 | 6-fluorobenzotiazol-2-yl | CH | H |
| 313 | 6-fluorobenzotiazol-2-yl | N | H |
| 314 | 6-chlorobenzotiazol-2-yl | CH | H |
| 315 | 6-chlorobenzotiazol-2-yl | N | H |
| 316 | 6-trifluoromethylbenzotiazol-2-yl | CH | H |
| 317 | 6-trifluoromethylbenzotiazol-2-yl | N | H |

TABLE 6

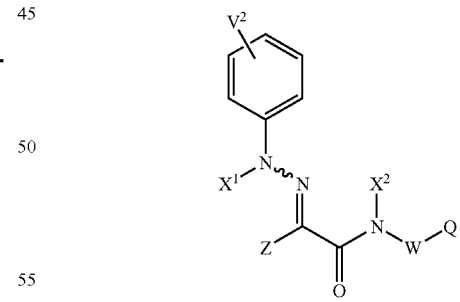

| No. | Q | V² | W | X¹ | X² | Z | E/Z |
|---|---|---|---|---|---|---|---|
| 318 | 2-chlorothiazol-5-yl | 4-CF₃ | CH₂ | H | H | H | E |
| 319 | 2-chlorothiazol-5-yl | 4-CF₃ | CH₂ | H | H | Cl | E |
| 320 | 2-chlorothiazol-5-yl | 3,4-F | CH₂ | H | H | Me | E |
| 321 | 2-chlorothiazol-5-yl | 3,4,5-F | CH₂ | H | H | Me | E |
| 322 | 2-chlorothiazol-5-yl | 3-Cl-4-F | CH₂ | H | H | Me | E |
| 323 | 2-chlorothiazol-5-yl | 3-F-4-CF₃ | CH₂ | H | H | Me | E |
| 324 | 2-chlorothiazol-5-yl | 3,5-F-4-CF₃ | CH₂ | H | H | Me | E |
| 325 | 2-chlorothiazol-5-yl | 3-F-5-CF₃ | CH₂ | H | H | Me | E |
| 326 | 2-chlorothiazol-5-yl | 3-CF₃-4-F | CH₂ | H | H | Me | E |

TABLE 6-continued

| No. | Q | V² | W | X¹ | X² | Z | E/Z |
|-----|---|----|----|----|----|---|-----|
| 327 | 2-chlorothiazol-5-yl | 3,4-Cl | CH₂ | H | H | Me | E |
| 328 | 2-chlorothiazol-5-yl | 3-Cl-4-CF₃ | CH₂ | H | H | Me | E |
| 329 | 2-chlorothiazol-5-yl | 3,5-Cl-4-CF₃ | CH₂ | H | H | Me | E |
| 330 | 2-chlorothtazol-5-yl | 3-CF₃-4-Cl | CH₂ | H | H | Me | E |
| 331 | 2-chlorothiazol-5-yl | 4-Br | CH₂ | H | H | Me | E |
| 332 | 2-chlorothiazol-5-yl | 3-CF₃-4-Br | CH₂ | H | H | Me | E |
| 333 | 2-chlorothiazol-5-yl | 3-CF₃ | CH₂ | H | H | Me | E |
| 334 | 2-chlorothiazol-5-yl | 3,4-CF₃ | CH₂ | H | H | Me | E |
| 335 | 2-chlorothiazol-5-yl | 4-OCF₃ | CH₂ | H | H | Me | E |
| 336 | 2-chlorothiazol-5-yl | 3-F-4-CF₃ | CH₂ | Me | H | Me | E |
| 337 | 2-chlorothiazol-5-yl | 3,5-F-4-CF₃ | CH₂ | Me | H | Me | E |
| 338 | 2-chlorothiazol-5-yl | 4-CF₃ | CH₂ | Me | H | Me | E |
| 339 | 2-chlorothiazol-5-yl | 3,5-F-4-CF₃ | CH₂ | Me | Me | Me | E, Z |
| 340 | 2-chlorothiazol-5-yl | 3-F-4-CF₃ | CH₂ | i-Pr | H | Me | E |
| 341 | 2-chlorothiazol-5-yl | 4-CF₃ | CH₂ | i-Pr | H | Me | E |
| 342 | 2-chlorothiazol-5-yl | 4-CF₃ | CH₂ | H | H | CN | |
| 343 | 2-chlorothiazol-5-yl | 4-CF₃ | CH₂ | H | H | NHMe | E |

In case where Z is CN, geometrical isomerism (E/Z) was not determined.

TABLE 7

| No. | U | V¹ | V² | W | X¹ | X² | Z | E/Z |
|-----|---|----|----|----|----|----|---|-----|
| 344 | N | 4,5-Cl | 4-Cl | CH₂ | H | H | Me | E |
| 345 | N | 4,5-Cl | 3-CF₃ | CH₂ | H | H | Me | E |
| 346 | N | 4,5-Cl | 3,4-CF₃ | CH₂ | H | H | Me | E |

TABLE 8

| No. | Q | V² | W | X¹ | X² | Z | E/Z |
|-----|---|----|----|----|----|---|-----|
| 347 | 2-chlorothiazol-5-yl | 4-Cl | CH₂ | H | H | Me | E |

Compound No.: Physical Properties (melting point (mp), refractive index, ¹H NMR)

1: mp 201° C.; ¹H NMR (400 MHz, DMSO-d₆) δ4.37 (2H, d), 7.14 (1H, s), 7.21 (2H, d), 7.30 (4H, t), 7.38 (2H, d), 8.32 (1H, s).
2: mp 174° C.; ¹H NMR (400 MHz, CDCl₃) δ4.64 (2H, d), 6.99(2H, d), 7.25 (2H, d), 7.44 (2H, d), 7.61 (2H, d), 8.07 (1H, s), 8.32 (1H, s), 8.68 (1H, t), 10.97 (1H, s).
3: mp 138–140° C.; ¹H NMR (400 MHz, CDCl₃) δ4.57 (2H, d), 5.18 (2H, s), 6.71 (1H, s), 7.04 (1H, brt), 7.26–7.49 (8H, m), 7.67 (3H, m), 8.37 (1H, s).
4: mp 142–145° C.; ¹H NMR (400 MHz, CDCl₃) δ4.58 (2H, d), 6.99 (1H, brs), 7.04 (2H, d), 7.26–7.35 (6H, m), 8.13 (1H, s).
6: ¹H NMR (400 MHz, CDCl₃) δ2.14 (3H, s), 4.59 (2H, d), 6.95 (1H, t), 7.08 (2H, dd), 7.26–7.36 (8H, m), 7.46 (1H, s).
7: mp 178–179° C.; ¹H NMR (400 MHz, CDCl₃) δ2.13 (3H, s), 4.58 (2H, d), 7.01 (2H, d), 7.23 (2H, d), 7.26–7.38 (5H, m), 7.46 (1H, brs).
8: mp 183° C.; ¹H NMR (400 MHz, CDCl₃) δ2.17 (3H, s), 4.59 (2H, d), 7.14 (2H, d), 7.26–7.40 (6H, m), 7.52 (2H, d), 7.61 (1H, brs).
9: mp 192° C.; ¹H NMR (400 MHz, CDCl₃) δ2.17 (3H, s), 4.60 (2H, d), 7.16 (2H, d), 7.29 (1H, ddd), 7.35 (1H, brt), 7.54 (2H, d), 7.65 (1H, s), 7.69 (1H, ddd), 8.55 (1H, dd), 8.61 (1H, d).
10: mp 116–117° C.; ¹H NMR (400 MHz, CDCl₃) δ2.14 (3H, s), 4.57 (2H, d), 6.97 (1H, ddd), 7.03 (2H, d), 7.03 (1H, dd), 7.10 (1H, d), 7.24 (2H, d), 7.31 (1H, ddd), 7.32 (1H, brt), 7.48 (1H, brs).
11: mp 91–93° C.; ¹H NMR (400 MHz, CDCl₃) δ2.13 (3H, s), 4.52 (2H, d), 7.02–7.07 (1H, m), 7.03 (2H, d), 7.08–7.18 (2H, m), 7.25 (2H, d), 7.33 (1H, brt), 7.49 (1H, brs).
12: n_D²⁵ 1.5390; ¹H NMR (400 MHz, CDCl₃) δ2.16 (3H, s), 4.54 (2H, d), 7.06–7.33 (6H, m), 7.54 (2H, d), 7.63 (1H, s).
13: mp 159–160° C.; ¹H NMR (400 MHz, CDCl₃) δ2.13 (3H, s), 4.54 (2H, d), 7.01 (2H, d), 7.03 (2H, d), 7.24 (2H, d), 7.30 (2H, dd), 7.44 (1H, brs).
14: mp 140° C.; ¹H NMR (400 MHz, CDCl₃) δ2.18 (3H, s), 4.55 (2H, d), 7.03 (2H, dd), 7.19 (1H, dd), 7.31 (2H, dd), 7.31 (1H, brt), 7.33 (1H, d), 7.36 (1H, d), 7.85 (1H, s).
15: mp 133° C.; ¹H NMR (400 MHz, CDCl₃) δ2.12 (3H, s), 4.54 (2H, d), 6.97 (2H, d), 7.03 (2H, dd), 7.29 (1H, brt), 7.30 (2H, dd), 7.38 (2H, d), 7.48 (1H, brs).
16: mp 106–108° C.; ¹H NMR (400 MHz, CDCl₃) δ2.16 (3H, s), 4.54 (2H, d), 7.04 (2H, dd), 7.14 (2H, d), 7.30 (2H, d), 7.31 (1H, t), 7.53 (2H, d), 7.63 (1H, brs).
17: mp 207° C.; ¹H NMR (400 MHz, CDCl₃) δ2.16 (3H, s), 4.58 (2H, d), 6.92 (1H, dd), 7.15 (2H, d), 7.36 (1H, brt), 7.54 (2H, d), 7.64 (1H, brs), 7.81 (1H, ddd), 8.20 (1H, d).
18: mp 162–163° C.; ¹H NMR (400 MHz, CDCl₃) δ2.10 (3H, s), 4.65 (2H, d), 7.03 (2H, d), 7.23 (1H, dd), 7.25 (2H, d), 7.37–7.43 (3H, m), 7.49 (1H, brs), 7.51 (1H, t).
19: mp 132° C.; ¹H NMR (400 MHz, CDCl₃) δ2.14 (3H, s), 4.62 (2H, d), 7.16 (2H, d), 7.23 (1H, dd), 7.36 (1H, d), 7.41 (1H, d), 7.49 (1H, brt), 7.55 (2H, d), 7.61 (1H, s).
20: mp 125–127° C.; ¹H NMR (400 MHz, CDCl₃) δ2.14 (3H, s), 4.55 (2H, d), 7.03 (2H, d), 7.20–7.29 (3H, m), 7.25 (2H, d), 7.32 (1H, brs), 7.32 (1H, t), 7.48 (1H, brs).
21: mp 130° C.; ¹H NMR (400 MHz, CDCl₃) δ2.13 (3H, s), 4.55 (2H, d), 6.98 (2H, d), 7.19–7.28 (4H, m), 7.32 (1H, brt), 7.39 (2H, d), 7.47(1H, brs).
22: n_D²⁵ 1.5537; ¹H NMR (400 MHz, CDCl₃) δ4.54 (2H, d), 7.18 (3H, t), 7.35 (1H, brs), 7.41 (2H, d), 7.55 (2H, d), 7.66 (1H, s).
23: ¹H NMR (400 MHz, CDCl₃) δ2.16 (3H, s), 4.53 (2H, d), 7.17 (2H, d), 7.20 (2H, d), 7.27 (1H, t), 7.39 (1H, brt), 7.54 (2H, d), 7.75 (1H, brs).
24: mp 102–104° C.; ¹H NMR (400 MHz, CDCl₃) δ2.16 (3H, s), 4.55 (2H, d), 6.52–6.58 (1H, m), 6.97–7.04 (1H, m), 7.09–7.15 (1H, m), 7.27 (2H, d), 7.32 (2H, d), 7.57 (1H, brs).

TABLE 8-continued

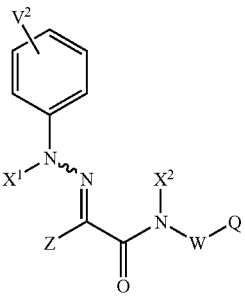

| No. | Q | V² | W | X¹ | X² | Z | E/Z |
|---|---|---|---|---|---|---|---|

25: mp 128–130° C.; ¹H NMR (400 MHz, CDCl₃) δ2.11 (3H, s), 4.54 (2H, d), 6.64 (1H, dddd), 6.79 (1H, ddd), 6.87 (1H, ddd), 7.23 (1H, ddd), 7.27 (2H, d), 7.31 (1H, t), 7.32 (2H, d), 7.51 (1H, brs).
26: mp 165° C.; ¹H NMR (400 MHz, CDCl₃) δ2.13 (3H, s), 4.54 (2H, d), 6.70 (2H, ddd), 7.24 (1H, brt), 7.27 (2H, d), 7.32 (2H, d), 7.41 (1H, s).
27: mp 191° C.; ¹H NMR (400 MHz, CDCl₃) δ2.12 (3H, s), 4.56 (2H, d), 6.71 (2H, ddd), 7.29 (1H, brt), 7.31 (1H, d), 7.43 (1H, s), 7.67 (1H, dd), 8.37 (1H, d).
28: mp 151–152° C.; ¹H NMR (400 MHz, CDCl₃) δ2.14 (3H, s), 4.54 (2H, d), 6.39 (1H, tt), 6.61 (2H, dd), 7.27 (2H, d), 7.28 (1H, brt), 7.32(2H, d), 7.52 (1H, brs).
29: mp 221–222° C.; ¹H NMR (400 MHz, CDCl₃) δ2.13 (3H, s), 4.57 (2H, d), 6.40 (1H, tt), 6.62 (2H, dd), 7.31 (1H, d), 7.33 (1H, brt), 7.55(1H, brs), 7.67 (1H, dd), 8.38 (1H, d).
30: mp 53° C.; ¹H NMR (400 MHz, CDCl₃) δ2.16 (3H, s), 4.55 (2H, d), 6.83(1H, dd), 6.96 (1H, dd), 7.27 (2H, d), 7.28 (1H, brt), 7.32 (2H, d), 7.48 (1H, t), 7.68 (1H, s).
31: mp 194° C.; ¹H NMR (400 MHz, CDCl₃) δ2.16 (3H, s), 4.57 (2H, d), 6.84 (1H, dd), 6.97 (1H, dd), 7.31 (1H, d), 7.34 (1H, brt), 7.49 (1H, dd), 7.67 (1H, dd), 7.69 (1H, brs), 8.38 (1H, d).
32: mp 154° C.; ¹H NMR (400 MHz, CDCl₃) δ2.12 (3H, s), 4.54 (2H, d), 7.00 (2H, dd), 7.03 (2H, dd), 7.25 (2H, d), 7.31 (2H, d), 7.44 (1H, brs).
33: mp 159–160° C.; ¹H NMR (400 MHz, CDCl₃) δ2.12 (3H, s), 4.55 (2H, d), 6.99 (2H, dd), 7.04 (2H, dd), 7.29 (1H, d), 7.36 (1H, brt), 7.47(1H, s), 7.66 (1H, dd), 8.36 (1H, d).
34: mp 171° C.; ¹H NMR (400 MHz, CDCl₃) δ2.15(3H, s), 4.55 (2H, d), 7.14 (1H, dd), 7.22 (1H, dd), 7.24 (1H, dd), 7.27 (2H, d), 7.28 (1H, brt), 7.32 (2H, d), 7.48 (1H, s).
35: mp 184–186° C.; ¹H NMR (400 MHz, CDCl₃) δ2.14 (3H, s), 4.57 (2H, d), 7.15 (1H, dd), 7.23 (1H, ddd), 7.25 (1H, dd), 7.29 (1H, brt), 7.30 (1H, d), 7.50 (1H, s), 7.67 (1H, dd), 8.37 (1H, d).
36: mp 133° C.; ¹H NMR (400 MHz, CDCl₃) δ2.18 (3H, s), 4.55 (2H, d), 6.89 (1H, ddd), 7.23 (1H, dd), 7.27 (2H, d), 7.32 (1H, d), 7.32 (2H, dd), 7.44 (1H, dd), 7.94 (1H, brs).
37: mp 185° C.; ¹H NMR (400 MHz, CDCl₃) δ2.17 (3H, s), 4.57 (2H, d), 7.20 (1H, dd), 7.31 (1H, d), 7.32 (1H, brt), 7.34 (1H, d), 7.37 (1H, d), 7.67 (1H, dd), 7.88 (1H, s), 8.37 (1H, d).
38: ¹H NMR (400 MHz, CDCl₃) δ2.14 (3H, s), 4.54 (2H, d), 7.19 (1H, dd), 7.26 (2H, d), 7.29 (1H, brt), 7.31 (1H, d), 7.38 (1H, d), 7.39 (1H, d), 7.67 (1H, brs).
39: mp 193–194° C.; ¹H NMR (400 MHz, CDCl₃) δ2.15 (3H, s), 4.57 (2H, d), 7.20 (1H, dd), 7.31 (1H, d), 7.31 (1H, brt), 7.38 (1H, d), 7.41(1H, d), 7.57 (1H, brs), 7.67 (1H, dd), 8.38 (1H, d).
40: mp 88° C.; ¹H NMR (400 MHz, CDCl₃) δ2.19 (3H, s), 4.50 (2H, d), 7.23(2H, d), 7.30 (2H, d), 7.38 (1H, brt), 7.58 (2H, s), 7.80 (1H, s).
41: mp 100° C.; ¹H NMR (400 MHz, CDCl₃) δ2.19 (3H, s), 4.52 (2H, d), 7.29 (1H, d), 7.43 (1H, brt), 7.59 (2H, s), 7.62 (1H, dd), 7.80 (1H, s), 8.33 (1H, s).
42: mp 157–159° C.; ¹H NMR (400 MHz, CDCl₃) δ2.13 (3H, s), 4.55 (2H, d), 6.91–6.93 (2H, m), 7.14 (1H, dd), 7.20 (1H, dd), 7.29 (1H, d), 7.31 (2H, d), 7.31 (1H, d), 7.48 (1H, brs).
43: (E:Z = 5:1); mp 152–153° C.; ¹H NMR (400 MHz, CDCl₃) δ2.13 (3H, s), 4.55 (2H, d), 6.90 (1H, dd), 7.24 (1H, d), 7.27 (2H, d), 7.31 (2H, d), 7.31 (1H, d), 7.46 (1H, brs).
44: mp 166–167° C.; ¹H NMR (400 MHz, CDCl₃) δ2.13 (3H, s), 4.57 (2H, d), 6.90 (1H, dd), 7.24 (1H, d), 7.31 (1H, d), 7.33 (1H, d), 7.35 (1H, brt), 7.50 (1H, s), 7.67 (1H, dd), 8.38 (1H, d).
45: mp 175° C.; ¹H NMR (400 MHz, DMSO-d₆) δ2.06 (3H, s), 4.40 (2H, d), 7.30 (2H, d), 7.35 (2H, d), 7.66 (2H, s), 8.89 (1H, brt), 9.85 (1H, s).
46: mp 170° C.; ¹H NMR (400 MHz, CDCl₃) δ2.17 (3H, s), 4.50(2H, d), 6.08 (1H, brt), 7.18 (2H, d), 7.25 (1H, d), 7.34 (2H, d), 12.93 (1H, s).
47: mp 245° C.; ¹H NMR (400 MHz, DMSO-d₆) δ2.04 (3H, s), 4.42 (2H, d), 7.47 (1H, d), 7.67 (1H, d), 7.75 (1H, dd), 8.35 (1H, d), 8.91 (1H, brt), 9.87 (1H, s).

TABLE 8-continued

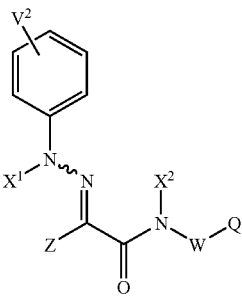

| No. | Q | V² | W | X¹ | X² | Z | E/Z |
|---|---|---|---|---|---|---|---|

48: mp 186–189° C.; ¹H NMR (400 MHz, CDCl₃) δ2.13 (3H, s), 4.55 (2H, d), 6.93 (1H, t), 6.98 (2H, d), 7.27 (2H, d), 7.31 (1H, t), 7.32 (2H, d), 7.48 (1H, brs).
49: mp 153–156° C.; ¹H NMR (400 MHz, CDCl₃) δ2.12 (3H, s), 4.53 (2H, d), 7.02 (2H, d), 7.23 (2H, d), 7.25 (2H, d), 7.28 (2H, d), 7.31 (1H, brd), 7.56 (1H, brs).
50: mp 156–160° C.; ¹H NMR (400 MHz, CDCl₃) δ2.12 (3H, s), 4.56 (2H, d), 7.02 (2H, d), 7.25 (2H, d), 7.30 (1H, d), 7.33 (1H, brt), 7.49 (1H, s), 7.66 (1H, dd), 8.37 (1H, d).
51: mp 153° C.; ¹H NMR (400 MHz, CDCl₃) δ2.13 (3H, s), 4.55 (2H, d), 6.97 (1H, ddd), 7.07 (1H, ddd), 7.14 (1H, dd), 7.27 (2H, d), 7.28–7.31 (2H, m), 7.31 (2H, d), 7.45 (1H, brs).
52: mp 166° C.; ¹H NMR (400 MHz, CDCl₃) δ2.12 (3H, s), 4.53 (2H, d), 6.97 (2H, d), 7.26 (2H, d), 7.31 (2H, d), 7.38 (2H, d), 7.48 (1H, brs).
53: mp 163° C.; ¹H NMR (400 MHz, CDCl₃) δ2.12 (3H, s), 4.56 (2H, d), 6.97 (2H, d), 7.30 (1H, d), 7.34 (1H, brt), 7.39 (2H, d), 7.48 (1H, brs), 7.66 (1H, dd), 8.37 (1H, d).
54: mp 128° C.; ¹H NMR (400 MHz, CDCl₃) δ2.17 (3H, s), 4.54 (2H, d), 7.14 (2H, d), 7.26 (2H, d), 7.32 (2H, d), 7.56 (2H, d), 7.77 (1H, s).
55: mp 160° C.; ¹H NMR (400 MHz, CDCl₃) δ2.11 (3H, s), 2.30 (3H, s), 4.54 (2H, d), 6.98 (2H, d), 7.09 (2H, d), 7.27 (2H, d), 7.31 (2H, d), 7.34 (1H, brt), 7.42 (1H, brs).
56: ¹H NMR (400 MHz, CDCl₃) δ1.21 (3H, t), 2.12 (3H, s), 2.59 (2H, q), 4.54 (2H, d), 7.01 (2H, d), 7.12 (2H, d), 7.26–7.32 (5H, m), 7.42 (1H, s).
57: mp 132–139° C.; ¹H NMR (400 MHz, CDCl₃) δ1.30 (9H, s), 2.11 (3H, s), 4.53 (2H, d), 7.02 (2H, d), 7.26 (2H, d), 7.31 (2H, d), 7.44 (1H, brs).
58: mp 125° C.; ¹H NMR (400 MHz, CDCl₃) δ2.16 (3H, s), 4.55 (2H, d), 7.01 (1H, dd), 7.27 (2H, d), 7.32 (2H, d), 7.48 (1H, dd), 7.53 (1H, dd), 7.58 (1H, d), 7.97 (1H, brs).
59: mp 135–137° C.; ¹H NMR (400 MHz, CDCl₃) δ2.15 (3H, s), 4.55 (2H, d), 7.20 (1H, d), 7.25 (1H, d), 7.27 (2H, d), 7.31 (2H, d), 7.32 (1H, brs), 7.40 (1H, dd), 7.59 (1H, brs).
60: mp 181–182° C.; ¹H NMR (400 MHz, CDCl₃) δ2.15 (3H, s), 4.58 (2H, d), 7.23 (1H, dd), 7.31 (1H, d), 7.32 (1H, brs), 7.37 (1H, d), 7.41 (1H, dd), 7.58 (1H, s), 7.64 (1H, dd), 8.38 (1H, d).
61: mp 111° C.; ¹H NMR (400 MHz, CDCl₃) δ2.18 (3H, s), 4.59 (2H, d), 7.31 (1H, d), 7.38 (1H, brt), 7.44 (1H, brs), 7.50 (2H, brs), 7.68 (1H, dd), 7.82 (1H, brs), 8.39 (1H, d).
64: mp 137° C.; ¹H NMR (400 MHz, CDCl₃) δ2.14 (3H, s), 4.54 (2H, d), 7.07 (2H, d), 7.15 (2H, d), 7.26 (2H, d), 7.31 (2H, d), 7.48 (1H, brs).
65: mp 131–133° C.; ¹H NMR (400 MHz, CDCl₃) δ2.13 (3H, s), 4.56 (2H, d), 7.09 (2H, d), 7.16 (2H, d), 7.30 (1H, d), 7.35 (1H, brt), 7.66 (1H, dd), 8.37 (1H, d).
66: mp 148° C.; ¹H NMR (400 MHz, CDCl₃) δ2.16 (3H, s), 4.54 (2H, d), 7.11 (2H, d), 7.27 (2H, d), 7.32 (2H, d), 7.56 (2H, d), 7.60 (1H, brs).
67: mp 130–131° C.; ¹H NMR (400 MHz, CDCl₃) δ2.19 (3H, s), 4.51 (2H, d), 6.06 (1H, brt), 7.16 (2H, d), 7.26 (2H, d), 7.34 (2H, d), 7.52 (2H, d), 11.01 (1H, brs).
68: (E:Z = 3:1); mp 178° C.; ¹H NMR (400 MHz, CDCl₃) (E isomer) δ2.15 (3H, s), 4.56 (2H, d), 7.12 (2H, d), 7.30 (1H, d), 7.35 (1H, brt), 7.57 (2H, d), 7.65 (1H, s), 7.66 (1H, dd), 8.36 (1H, s); (Z isomer) δ2.19 (3H, s), 4.54 (2H, d), 7.16(2H, d), 7.33 (2H, d), 7.54 (2H, d), 7.65 (1H, s), 7.66 (1H, dd), 12.95 (1H, brs).
69: mp 182–183° C.; ¹H NMR (400 MHz, CDCl₃) δ2.16 (3H, s), 4.5 (1H, brs), 4.57 (2H, d), 7.17 (2H, d), 7.55 (2H, d), 7.64 (2H, d), 7.79 (1H, d), 8.29 (1H, d).
70: mp 179° C.; ¹H NMR (400 MHz, CDCl₃) δ2.13 (3H, s), 4.53 (2H, d), 6.89 (1H, dd), 7.21 (2H, d), 7.23 (2H, d), 7.29 (1H, brt), 7.32 (1H, d), 7.45 (1H, brs), 7.47 (2H, d).
71: mp 167° C.; ¹H NMR (400 MHz, CDCl₃) δ2.13 (3H, s), 4.52 (2H, d), 7.01 (2H, d), 7.21 (2H, d), 7.24 (2H, d), 7.29 (1H, t), 7.46 (1H, brs), 7.46 (1H, brs).

TABLE 8-continued

| No. | Q | V² | W | X¹ | X² | Z | E/Z |
|---|---|---|---|---|---|---|---|

72: mp 164–166° C.; ¹H NMR (400 MHz, CDCl₃) δ2.12 (3H, s), 4.52 (2H, d), 6.97 (2H, d), 7.21 (2H, d), 7.28 (1H, brt), 7.38 (2H, d), 7.46 (2H, d), 7.48 (1H, brs).
73: mp 127–129° C.; ¹H NMR (400 MHz, CDCl₃) δ2.16 (3H, s), 4.53 (2H, d), 7.14 (2H, d), 7.22 (2H, d), 7.30 (1H, brt), 7.47 (2H, d), 7.53 (2H, d), 7.62 (1H, brs).
74: mp 151° C.; ¹H NMR (400 MHz, CDCl₃) δ2.16 (3H, s), 4.55 (2H, d), 7.15 (2H, d), 7.37 (1H, brt), 7.46 (1H, d), 7.54 (2H, d), 7.56 (1H, dd), 7.66 (1H, brs), 8.36 (1H, d).
75: ¹H NMR (400 MHz, CDCl₃) δ2.18 (3H, s), 4.59 (2H, d), 7.17 (2H, d), 7.38 (1H, brs), 7.55 (2H, d), 7.65 (1H, s), 7.83 (1H, s), 8.52 (1H, d), 8.61 (1H, d).
76: ¹H NMR (400 MHz, CDCl₃) δ2.13 (3H, s), 2.25 (3H, s), 2.31 (3H, s), 4.58 (2H, d), 6.99 (2H, d), 7.10–7.15 (4H, m), 7.25 (2H, d), 7.41 (1H, s).
77: ¹H NMR (400 MHz, CDCl₃) δ1.20 (3H, t), 2.11 (3H, s), 2.58 (2H, q), 4.58 (2H, d), 6.98 (2H, d), 7.07–7.16 (6H, m), 7.39 (1H, s).
78: mp 173° C.; ¹H NMR (400 MHz, CDCl₃) δ2.13 (3H, s), 2.35 (3H, s), 4.53 (2H, d), 7.00 (2H, d), 7.17 (2H, d), 7.23 (2H, d), 7.23 (2H, d), 7.42 (1H, brs).
79: mp 197–198° C.; ¹H NMR (400 MHz, CDCl₃) δ2.16 (3H, s), 2.55 (3H, s), 4.56 (2H, d), 7.14 (2H, d), 7.28 (1H, brs), 7.53 (2H, d), 7.58 (1H, dd), 7.62 (1H, s), 8.48 (1H, d).
80: ¹H NMR (400 MHz, CDCl₃) δ1.23 (3H, t), 2.11 (3H, s), 2.28 (6H, s), 2.64 (2H, q), 4.56 (2H, d), 6.60 (1H, s), 6.71 (2H, s), 7.18 (2H, d), 7.26–7.36 (4H, m).
81: ¹H NMR (400 MHz, CDCl₃) δ1.23 (3H, t), 2.13 (3H, s), 2.65 (2H, q), 4.52 (2H, q), 7.00 (2H, d), 7.18–7.27 (7H, m), 7.43 (1H, s).
82: ¹H NMR (400 MHz, CDCl₃) δ1.30 (3H, t), 2.16 (3H, s), 2.82 (2H, q), 4.56 (2H, d), 7.13–7.16 (3H, m), 7.28 (1H, brs), 7.53 (2H, d), 7.60 (2H, m), 8.51 (1H, d).
83: ¹H NMR (400 MHz, CDCl₃) δ0.94 (3H, t), 1.63 (2H, m), 2.13 (3H, s), 2.58 (2H, t), 4.54 (2H, d), 7.01 (2H, d), 7.16 (2H, d), 7.22–7.26 (5H, m), 7.41 (1H, s).
84: ¹H NMR (400 MHz, CDCl₃) δ0.94 (3H, t), 1.21 (3H, t), 1.63 (2H, m), 2.12 (3H, s), 2.59 (2H, q), 4.54 (2H, d), 7.00 (2H, d), 7.10 (2H, d), 7.15 (2H, d), 7.25 (2H, d), 7.39 (1H, brt), 7.39 (1H, s).
85: mp 142–144° C.; ¹H NMR (400 MHz, CDCl₃) δ0.94 (3H, t), 1.38 (2H, tq), 1.70 (2H, U), 2.16 (3H, s), 2.79(2H, t), 4.56 (2H, d), 7.13 (2H, d), 7.14 (2H, d), 7.31 (1H, brt), 7.53 (2H, d), 7.60 (1H, dd), 7.63 (1H, brs), 8.50 (1H, d).
86: mp 158° C.; ¹H NMR (400 MHz, CDCl₃) δ1.32 (9H, s), 2.13 (3H, s), 4.55 (2H, d), 7.01 (2H, d), 7.23 (2H, d), 7.27 (2H, d), 7.38 (2H, d), 7.45 (1H, brs).
87: mp 114–116° C.; ¹H NMR (400 MHz, CDCl₃) δ2.14 (3H, s), 4.63 (2H, d), 7.03 (2H, d), 7.25 (2H, d), 7.37 (1H, brt), 7.45–7.56 (4H, m), 7.58 (1H, brs).
88: mp 82–83° C.; ¹H NMR (400 MHz, CDCl₃) δ2.14 (3H, s), 4.69 (2H, d), 7.05 (2H, d), 7.26 (2H, d), 7.45 (1H, brt), 7.52 (1H, s), 7.78 (2H, s), 7.78 (1H, s).
89: mp 61–63° C.; ¹H NMR (400 MHz, CDCl₃) δ2.14 (3H, s), 4.64 (2H, d), 6.90 (1H, dd), 7.24 (2H, d), 7.32 (1H, d), 7.36 (1H, brt), 7.44 (2H, d), 7.49 (1H, brs), 7.60 (2H, d).
90: mp 147–149° C.; ¹H NMR (400 MHz, CDCl₃) δ2.14 (3H, s), 4.63 (2H, d), 7.03 (2H, d), 7.25 (2H, d), 7.38 (1H, t), 7.44 (1H, d), 7.49 (1H, brs), 7.60 (2H, d).
91: mp 116–118° C.; ¹H NMR (400 MHz, CDCl₃) δ2.14 (3H, s), 4.64 (2H, d), 7.15 (2H, d), 7.38 (1H, brt), 7.45 (2H, d), 7.54 (2H, d), 7.61 (2H, d), 7.62 (1H, brs).
92: mp 139–141° C.; ¹H NMR (400 MHz, CDCl₃) δ2.17 (3H, s), 4.68 (2H, d), 7.17 (2H, d), 7.45 (1H, brt), 7.55 (2H, d), 7.67 (2H, d), 7.88 (1H, s), 8.72 (1H, s).
94: mp 161–163° C.; ¹H NMR (400 MHz, CDCl₃) δ2.16 (3H, s), 3.91 (3H, s), 4.51, (2H, d), 6.74 (2H, d), 7.14 (2H, d), 7.25 (1H, brs), 7.53 (2H, d), 7.60 (2H, m), 8.14 (1H, s).
95: mp 138–139° C.; ¹H NMR (400 MHz, CDCl₃) δ1.39 (3H, t), 2.16 (3H, s), 4.35 (2H, q), 4.50 (2H, d), 6.72 (1H, d), 7.14 (2H, d), 7.25 (1H, brs), 7.53 (2H, d), 7.59 (1H, d), 8.12 (1H, s).
96: ¹H NMR (400 MHz, CDCl₃) δ2.17 (3H, s), 4.59 (2H, d), 7.15 (2H, d), 7.19 (2H, d), 7.35 (1H, brt), 7.36 (1H, d), 7.54 (2H, d), 7.64 (1H, brs).
97: mp 164–165° C.; ¹H NMR (400 MHz, CDCl₃) δ2.15 (3H, s), 3.09 (6H, s), 4.43 (2H, d), 6.51 (1H, d), 7.12 (2H, m), 7.47 (1H, dd), 7.52 (2H, d), 7.60 (1H, s), 8.14 (1H, d).
98: mp 185–186° C.; ¹H NMR (400 MHz, CDCl₃) δ2.15 (3H, s), 2.93 (3H, s), 4.43 (2H, d), 4.55 (1H, brs), 6.39 (1H, d), 7.13 (3H, m), 7.46 (1H, dd), 7.53 (2H, d), 7.59 (1H, s), 8.07 (1H, s).
99: ¹H NMR (400 MHz, CDCl₃) δ2.18 (3H, s), 4.63 (2H, d), 7.16 (2H, d), 7.37 (1H, brt), 7.39 (2H, d), 7.54 (2H, d), 7.63 (2H, d), 7.65 (1H, brs).
100: mp 158° C.; ¹H NMR (400 MHz, CDCl₃) δ1.55 (3H, d), 2.08 (3H, s), 5.15 (1H, dt), 7.02 (2H, d), 7.16 (1H, brd), 7.27 (2H, d), 7.29 (2H, d), 7.31 (2H, d), 7.44 (1H, brs).
101: mp 145–146° C.; ¹H NMR (400 MHz, CDCl₃) δ2.08 (3H, s), 2.86 (2H, t), 3.60 (2H, dt), 6.91 (2H, d), 6.97 (1H, t), 7.18 (2H, d), 7.26 (2H, d), 7.31 (2H, d), 7.42 (1H, brs).
102: mp 155–158° C.; ¹H NMR (400 MHz, CDCl₃) δ2.11 (3H, s), 6.09 (1H, brs), 6.82 (2H, d), 7.01 (1H, t), 7.15 (2H, d), 7.18 (2H, d), 7.34 (2H, dd), 7.63 (1H, brs), 8.58 (1H, brs).
103: mp 171–172° C.; ¹H NMR (400 MHz, CDCl₃) δ2.06 (3H, s), 2.24 (3H, s), 6.38 (1H, d), 6.95 (1H, d), 7.21 (2H, d), 7.29 (1H, brs), 7.31 (2H, d).
106: mp 227–229° C.; ¹H NMR (400 MHz, CDCl₃) δ2.16 (3H, s), 6.09 (1H, d), 7.18 (1H, d), 7.20 (1H, d), 7.22 (1H, d), 7.59 (2H, d), 7.78 (1H, s), 8.07 (1H, brs), 8.55 (1H, brs).
107: mp 163–165° C.; ¹H NMR (400 MHz, CDCl₃) δ2.15 (3H, s), 7.08 (2H, d), 7.21 (2H, d), 7.29 (2H, d), 7.57 (2H, d), 7.68 (1H, brs), 9.64 (1H, brs).
108: ¹H NMR (400 MHz, CDCl₃) δ2.13 (3H, s), 7.16 (2H, d), 7.20 (2H, d), 7.52 (2H, d), 7.52 (2H, d), 8.10 (1H, brs), 9.81 (1H, brs).
111: (E:Z = 3:2); n_D²⁵ 1.5578; ¹H NMR (400 MHz, CDCl₃) (E isomer) δ2.23 (3H, s), 3.14 (3H, s), 3.26 (3H, s), 4.68 (2H, s), 7.00 (1H, d), 7.35 (1H, d), 7.53 (2H, d), 7.69 (1H, dd), 8.37 (1H, d); (Z isomer) δ2.21 (3H, s), 2.98(3H, s), 3.19 (3H, s), 4.76 (2H, s), 6.85 (1H, d), 7.33 (1H, d), 7.42 (2H, d), 7.75 (1H, dd), 8.34 (1H, s).
112: n_D²⁵ 1.5532; ¹H NMR (400 MHz, CDCl₃) δ2.24 (3H, s), 3.20 (3H, s), 3.78 (3H, s), 4.94 (2H, d), 6.98 (2H, d), 7.31 (1H, d), 7.51 (2H, d), 7.75 (1H, dd), 8.43 (1H, d).
113: mp 107–111° C.; ¹H NMR (400 MHz, CDCl₃) δ1.21 (3H, t), 1.98 (3H, s), 3.71 (2H, q), 4.56 (2H, d), 6.96 (2H, d), 7.33 (1H, d), 7.53 (2H, d), 7.67 (1H, brs), 7.68 (1H, d), 8.38 (1H, s).
114: mp 88° C.; ¹H NMR (400 MHz, CDCl₃) δ0.94 (3H, t), 1.70 (2H, m), 1.95 (3H, s), 3.60 (2H, t), 4.56(2H, d), 6.92(2H, d), 7.32 (2H, d), 7.52 (2H, d), 7.66 (1H, brs), 7.68 (1H, dd), 8.38 (1H, d).
115: mp 81–82° C.; ¹H NMR (400 MHz, CDCl₃) δ1.22 (6H, d), 1.69 (3H, s), 3.89 (1H, m), 4.57 (2H, d), 6.92 (2H, d), 7.33 (1H, d), 7.52 (2H, d), 7.61 (1H, brs), 7.68 (1H, dd), 8.38 (1H, d).
116: mp 110° C.; ¹H NMR (400 MHz, CDCl₃) δ0.93 (3H, t), 1.45 (2H, m), 1.61 (2H, m), 1.95(3H, s), 3.64(2H, t), 4.56 (2H, d), 6.92 (2H, d), 7.33 (1H, d), 7.52 (2H, d), 7.68 (1H, brs), 7.68 (1H, dd), 8.38 (1H, d).
117: ¹H NMR (400 MHz, CDCl₃) δ0.18 (2H, q), 0.50 (2H, q), 1.08 (1H, m), 1.90(3H, s), 3.52 (2H, d), 4.56(2H, d), 6.96 (2H, d), 7.33 (1H, d), 7.52 (2H, d), 7.66–7.68 (2H, m), 8.38 (1H, s).
118: mp 134–135° C.; ¹H NMR (400 MHz, CDCl₃) δ0.95 (6H, d), 1.86 (3H, s), 1.95(1H, m), 3.47 (2H, d), 4.56(2H, d), 6.88 (2H, d), 7.33 (1H, d), 7.51 (2H, d), 7.68 (1H, dd), 8.38 (1H, s).
119: mp 117° C.; ¹H NMR (400 MHz, CDCl₃) δ0.95 (3H, t), 1.19 (3H, d), 1.6(1H, m), 1.7(1H, m), 3.59(1H, m), 4.56 (2H, d), 6.89 (2H, d), 7.33 (1H, d), 7.52 (2H, d), 7.58 (1H, brt), 7.68 (1H, dd), 8.38 (1H, d).
120: mp 103° C.; ¹H NMR (400 MHz, CDCl₃) δ2.09 (3H, s), 4.28 (2H, d), 4.55 (2H, d), 5.24 (2H, t), 5.90 (1H, m), 7.00 (2H, d), 7.32 (1H, d), 7.53 (2H, d), 7.66 (1H, brs), 7.67 (1H, d), 8.37 (1H, d).

TABLE 8-continued

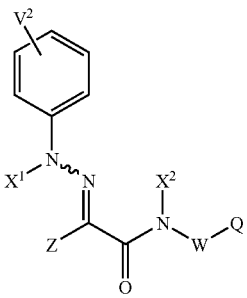

| No. | Q | V² | W | X¹ | X² | Z | E/Z |
|---|---|---|---|---|---|---|---|

121: mp 104° C.; ¹H NMR (400 MHz, CDCl₃) δ1.78 (3H, s), 2.11 (3H, s), 4.18 (2H, s), 4.55 (2H, d), 4.88 (1H, s), 4.98 (1H, s), 6.97 (2H, d), 7.32 (1H, d), 7.52 (2H, d), 7.59 (1H, brt), 7.67 (1H, dd), 8.37 (1H, d).
122: mp 137–140° C.; ¹H NMR (400 MHz, CDCl₃) δ1.85 (3H, s) 4.34 (2H, s), 4.56 (2H, d), 7.10 (2H, d), 7.34 (1H, d), 7.65 (2H, d), 7.69 (1H, d), 8.40 (1H, s).
123: mp 111° C.; ¹H NMR (400 MHz, CDCl₃) δ1.89 (3H, s), 3.91 (1H, t), 3.98 (1H, t), 4.55 (2H, d), 4.67 (1H, t), 6.95 (2H, d), 7.33 (1H, d), 7.54 (2H, d), 7.6 (1H, brt), 7.67 (1H, dd), 8.38 (1H, d).
124: $n_D^{25}$ 1.5022; ¹H NMR (400 MHz, CDCl₃) δ1.85 (3H, s), 4.19 (2H, q), 4.57 (2H, d), 6.94 (2H, d), 7.34 (1H, d), 7.57 (2H, d), 7.6 (1H, brt), 7.68 (1H, dd), 8.39 (1H, d).
125: mp 88–89° C.; ¹H NMR (400 MHz, CDCl₃) δ1.95 (3H, s), 3.37 (3H, s), 4.55 (2H, d), 4.96 (2H, s), 7.03 (2H, d), 7.32 (1H, d), 7.57 (2H, d), 8.69 (1H, m), 8.38 (1H, d).
126: mp 61–62° C.; ¹H NMR (400 MHz, CDCl₃) δ1.20 (3H, t), 1.98 (3H, s), 3.55 (2H, q), 4.53 (2H, d), 5.01 (2H, s), 7.04 (2H, d), 7.28 (2H, d), 7.33 (2H, d) 7.54 (2H, d), 7.60 (1H, brs).
128: mp 77–80° C.; ¹H NMR (400 MHz, CDCl₃) δ1.16 (6H, d), 1.97 (3H, s), 3.74 (1H, m), 4.55 (2H, d), 5.01 (2H, s), 7.06 (2H, d), 7.32 (1H, d), 7.55 (2H, d), 7.67 (2H, m), 8.37 (1H, d).
129: mp 86° C.; ¹H NMR (400 MHz, CDCl₃) δ0.87 (6H, d), 1.83 (1H, m), 1.98 (3H, s), 3.25 (2H, d), 4.55(2H, d), 5.00 (2H, d), 7.05 (2H, d), 7.32 (1H, d), 7.55 (2H, d), 7.67 (2H, dd), 8.38 (1H, d).
130: mp 63–64° C.; ¹H NMR (400 MHz, CDCl₃) δ1.94 (3H, s), 3.35 (3H, s), 3.53 (2H, m), 3.66 (2H, m), 4.55 (2H, d), 5.09 (2H, s), 7.06 (2H, d), 7.32 (1H, d), 7.55 (2H, d), 7.68 (2H, m), 8.38 (1H, d).
131: mp 94–96° C.; ¹H NMR (400 MHz, CDCl₃) δ1.25 (3H, t), 2.00 (3H, s), 4.22 (2H, q), 4.40 (2H, s), 4.54 (2H, d), 6.94 (2H, d), 7.32 (1H, d), 7.54 (2H, d), 7.6 (1H, brt), 7.67 (1H, dd), 8.37 (1H, d).
132: mp 115–116° C.; ¹H NMR (400 MHz, CDCl₃) δ2.00 (3H, s), 4.52 (2H, d), 4.90 (2H, s), 6.97 (2H, d), 7.22 (2H, d), 7.32 (4H, m), 7.51 (2H, d), 7.57 (1H, brt), 7.63 (1H, dd), 8.35 (1H, d).
133: mp 132–133° C.; ¹H NMR (400 MHz, CDCl₃) δ1.91 (3H, s), 4.52 (2H, d), 4.86 (2H, s), 7.05 (1H, d), 7.13 (1H, d), 7.26–7.37 (5H, m), 7.40 (1H, brt), 7.63 (3H, m), 8.35 (1H, d).
134: mp 143–146° C.; ¹H NMR (400 MHz, CDCl₃) δ1.97 (3H, s), 4.52 (2H, d), 4.91 (2H, s), 6.92 (2H, d), 7.33 (3H, m), 7.53 (3H, m), 7.63 (3H, m), 8.55 (1H, s).
135: mp 129° C.; ¹H NMR (400 MHz, CDCl₃) δ2.00 (3H, s), 2.34 (3H, s), 4.53 (2H, d), 4.85 (2H, s), 6.97 (2H, d), 7.11 (4H, m), 7.31 (1H, d), 7.50 (2H, d), 7.57 (1H, brs), 7.63 (1H, dd), 8.35 (1H, dd).
136: ¹H NMR (400 MHz, CDCl₃) δ1.85 (3H, brs), 2.26 (3H, brs), 4.53 (2H, d), 7.32 (2H, d), 7.35 (2H, d), 7.50 (1H, brt), 7.65 (1H, dd), 7.69 (2H, d), 8.36 (1H, d).
137: $n_D^{25}$ 1.5372; ¹H NMR (400 MHz, CDCl₃) δ1.89 (3H, s), 2.05 (3H, s), 4.55 (2H, d), 4.77 (2H, s), 7.05 (2H, d), 7.32 (1H, d), 7.57 (2H, d), 7.60 (1H, brs), 7.65 (1H, dd), 8.05 (1H, s), 8.38 (1H, s).
138: $n_D^{25}$ 1.5290; ¹H NMR (400 MHz, CDCl₃) δ1.10 (3H, t), 1.20 (3H, t), 2.02 (3H, s), 3.85 (2H, q), 3.99 (2H, s), 4.18 (2H, s), 4.20 (2H, q), 4.26 (2H, d), 4.74 (2H, s), 4.82 (2H, s), 6.94 (4H, m), 7.32 (1H, d), 7.52 (2H, d), 7.70 (1H, dd), 7.85 (1H, dd), 8.39 (1H, d).
139: mp 132–134° C.; ¹H NMR (400 MHz, CDCl₃) δ1.16 (3H, t), 2.67 (2H, q), 4.58 (2H, d), 7.00 (2H, d), 7.23 (2H, d), 7.35 (5H, m), 7.58 (1H, s).
140: mp 137° C.; ¹H NMR (400 MHz, CDCl₃) δ1.15 (3H, t), 2.66 (2H, q), 4.51 (2H, d), 7.00 (2H, d), 7.23 (4H, m), 7.47 (2H, d), 7.60 (1H, s).
141: mp 156–157° C.; ¹H NMR (400 MHz, CDCl₃) δ1.15 (3H, t), 2.35 (3H, s), 2.66 (2H, q), 4.53 (2H, d), 6.99 (1H, d), 7.16 (2H, d), 7.22 (4H, m), 7.59 (1H, s).
142: $n_D^{25}$ 1.5845; ¹H NMR (400 MHz, CDCl₃) δ1.25 (3H, t), 2.48 (2H, q), 4.60 (2H, d), 6.15 (1H, brs), 7.09 (2H, d), 7.21 (2H, d), 7.43 (2H, d), 7.62 (2H, d), 12.84 (1H, s).

TABLE 8-continued

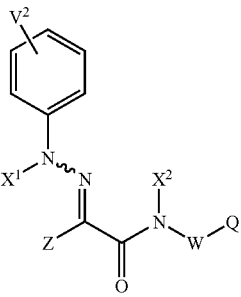

| No. | Q | V² | W | X¹ | X² | Z | E/Z |
|---|---|---|---|---|---|---|---|

143: $n_D^{25}$ 1.5771; ¹H NMR (400 MHz, CDCl₃) δ1.16 (3H, t), 2.65 (2H, q), 4.63 (2H, d), 7.02 (2H, d), 7.25 (2H, d), 7.35 (1H, brt), 7.45 (2H, d), 7.61 (3H, t).
144: mp 123° C.; ¹H NMR (400 MHz, CDCl₃) δ1.17 (3H, t), 2.68 (2H, q), 4.55 (2H, d), 7.04 (2H, t), 7.12 (2H, d), 7.25 (1H, brs), 7.31 (2H, t), 7.53 (2H, d), 7.75 (1H, s).
145: mp 134–135° C.; ¹H NMR (400 MHz, CDCl₃) δ1.17 (3H, t), 2.69 (2H, q), 4.55 (2H, d), 7.13 (2H, d), 7.27 (3H, m), 7.33 (2H, d), 7.76 (1H, s).
146: mp 149–150° C.; ¹H NMR (400 MHz, CDCl₃) δ1.16 (3H, t), 2.68 (2H, q), 4.57 (2H, d), 7.14 (2H, d), 7.31 (1H, d), 7.31 (1H, brt), 7.54 (2H, d), 7.67 (1H, dd), 7.79 (1H, s), 8.38 (1H, d).
147: $n_D^{25}$ 1.5127; ¹H NMR (400 MHz, CDCl₃) δ1.15 (3H, t), 2.70 (2H, q), 4.64 (2H, d), 7.15 (2H, d), 7.34 (1H, brs), 7.45 (2H, d), 7.54 (2H, d), 7.61 (2H, d), 7.80 (1H, s).
148: ¹H NMR (400 MHz, CDCl₃) δ1.11 (3H, t), 2.60 (2H, q), 2.84 (2H, t), 3.60 (2H, q), 6.90 (2H, d), 6.92 (1H, brs), 7.13 (2H, d), 7.27 (2H, d), 7.47 (3H, m), 7.54 (1H, s).
149: ¹H NMR (400 MHz, CDCl₃) δ1.00 (3H, t), 1.70 (2H, m), 2.39 (2H, t), 4.54 (2H, d), 6.06 (1H, brs), 7.07 (2H, d), 7.24 (2H, d), 7.30–7.40 (5H, m).
150: ¹H NMR (400 MHz, CDCl₃) δ1.04 (3H, t), 1.59 (2H, m), 2.63 (2H, t), 4.57 (2H, d), 7.00 (2H, d), 7.24–7.36 (7H, m), 7.61 (1H, s).
151: ¹H NMR (400 MHz, CDCl₃) δ1.00 (3H, t), 1.70 (2H, m), 2.40 (2H, q), 4.50 (2H, d), 6.06 (1H, brs), 7.08 (2H, d), 7.22 (4H, m), 7.33 (2H, d).
152: ¹H NMR (400 MHz, CDCl₃) δ 1.03 (3H, t), 1.65 (2H, m), 2.62 (2H, t), 4.53 (2H, d), 7.00 (2H, d), 7.20–7.33 (7H, m), 7.60 (1H, s).
153: mp 129–130° C.; ¹H NMR (400 MHz, CDCl₃) δ1.04 (3H, t), 1.60 (2H, m), 2.64 (2H, t), 4.56 (2H, d), 7.14 (2H, d), 7.33 (2H, m), 7.54 (2H, d), 7.66 (1H, dd), 7.81 (1H, s), 8.38 (1H, d).
154: ¹H NMR (400 MHz, CDCl₃) δ0.99 (3H, t), 1.68 (2H, m), 2.38 (2H, t), 4.49 (2H, d), 6.0 (1H, brs), 7.07 (2H, d), 7.19–7.22 (6H, m).
155: ¹H NMR (400 MHz, CDCl₃) δ1.03 (3H, t), 1.57 (2H, m), 2.61 (2H, t), 4.52 (2H, d), 6.99 (2H, d), 7.13 (2H, d), 7.24 (4H, m), 7.59 (1H, s).
156: mp 131–132° C.; ¹H NMR (400 MHz, CDCl₃) δ1.24 (6H, d), 2.67 (1H, m), 4.55 (2H, d), 6.14 (1H, brs), 7.08 (2H, d), 7.21 (2H, d), 7.33 (5H, m).
157: mp 123–124° C.; ¹H NMR (400 MHz, CDCl₃) δ1.24 (6H, d), 1.54 (3H, s), 2.67 (1H, m), 4.51 (2H, d), 6.15 (1H, brs), 7.07 (2H, d), 7.24 (4H, m), 7.34 (2H, d).
158: mp 114–115° C.; ¹H NMR (400 MHz, CDCl₃) δ1.24 (6H, d), 2.67 (1H, m), 4.50 (2H, d), 6.3 (1H, brs), 7.08 (2H, d), 7.20 (4H, m), 7.49 (2H, d).
159: mp 135° C.; ¹H NMR (400 MHz, CDCl₃) δ1.25 (6H, d), 2.69 (1H, m), 4.60 (2H, d), 6.23 (1H, brs), 7.08 (2H, d), 7.21 (2H, d), 7.43 (2H, d), 7.63 (2H, d), 12.69 (1H, s).
160: $n_D^{25}$ 1.5403; ¹H NMR (400 MHz, CDCl₃) δ1.38 (6H, d), 3.25 (1H, m), 4.60 (2H, d), 6.98 (2H, d), 7.23 (2H, d), 7.43 (2H, d), 7.60 (2H, d), 7.83 (1H, s).
161: mp 141° C.; ¹H NMR (400 MHz, CDCl₃) δ1.25 (6H, d), 2.69 (1H, m), 4.52 (2H, d), 6.20 (1H, brs), 7.19 (2H, d), 7.25 (2H, d), 7.35 (2H, d), 7.50 (2H, d), 12.80 (1H, s).
162: mp 141° C.; ¹H NMR (400 MHz, CDCl₃) δ1.25 (6H, d), 2.69 (1H, m), 4.55 (2H, d), 6.28 (1H, brs), 7.19 (2H, d), 7.34 (1H, d), 7.50 (2H, d), 7.66 (1H, dd), 8.37 (1H, d), 12.76 (1H, s).
163: mp 90° C.; ¹H NMR (400 MHz, CDCl₃) δ0.93 (3H, t), 1.21 (3H, d), 1.53 (1H, m), 1.79(1H, m), 2.42 (1H, m), 4.54(2H, m), 6.13 (1H, brs), 7.07 (2H, d), 7.21 (2H, d), 7.30–7.40 (5H, m), 12.74 (1H, s).
164: $n_D^{25}$ 1.5729; ¹H NMR (400 MHz, CDCl₃) δ0.94 (3H, t), 1.36 (3H, d), 1.76(1H, m), 1.94 (1H, m), 3.03(1H, m), 4.55 (2H, d), 6.97 (2H, d), 7.22–7.38 (8H, m), 7.81 (1H, s).
165: mp 117° C.; ¹H NMR (400 MHz, CDCl₃) δ0.94 (3H, t), 1.21 (3H, d), 1.53(1H, m), 1.79 (1H, m), 2.42(1H, m), 4.51 (2H, d), 6.14 (1H, s), 7.06 (2H, d), 7.20–7.26 (4H, m), 7.34 (2H, d), 12.72 (1H, s).

TABLE 8-continued

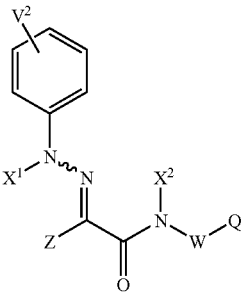

| No. | Q | V² | W | X¹ | X² | Z | E/Z |

166: $n_D^{25}$ 1.5759; ¹H NMR (400 MHz, CDCl₃) δ0.91 (3H, t), 1.12 (3H, d), 1.45 (1H, m), 1.77 (1H, m), 3.52(1H, q), 4.43 (2H, d), 7.2–7.4 (8H, m).
167: mp 97–99° C.; ¹H NMR (400 MHz, CDCl₃) δ0.95 (3H, t), 1.23 (3H, d), 1.53 (1H, m), 1.81 (1H, m), 2.43 (1H, m), 4.61 (2H, d), 6.2 (1H, brs), 7.07 (2H, d), 7.21 (2H, d), 7.43 (2H, d), 7.63 (2H, d).
168: $n_D^{25}$ 1.5525; ¹H NMR (400 MHz, CDCl₃) δ0.94 (3H, t), 1.35 (3H, d), 1.75 (1H, m), 1.94 (1H, m), 3.04 (1H, m), 4.60 (2H, d), 6.98 (2H, d), 7.25 (2H, d), 7.28 (1H, brs), 7.44 (2H, d), 7.60 (2H, d), 7.84 (1H, s).
169: mp 120° C.; ¹H NMR (400 MHz, CDCl₃) δ7.15 (2H, d), 7.37 (2H, d), 7.52 (2H, d), 7.60 (2H, d), 7.69 (1H, s), 7.80 (1H, s).
171: mp 121–126° C.; ¹H NMR (400 MHz, CDCl₃) δ2.11 (3H, s), 3.83 (2H, s), 4.57 (2H, d), 7.18 (2H, d), 7.32 (1H, d), 7.34 (1H, brs), 7.56 (2H, d), 7.66 (1H, d), 8.38 (1H, d), 9.00 (1H, s).
172: mp 171–173° C.; ¹H NMR (400 MHz, CDCl₃) δ4.53 (2H, d), 6.55 (1H, brs), 7.23–7.39 (9H, m).
173: mp 171–172° C.; ¹H NMR (400 MHz, CDCl₃) δ4.62 (2H, d), 6.8 (1H, brs), 7.15 (2H, d), 7.34–7.38 (7H, m), 9.03 (1H, s).
174: mp 157–158° C.; ¹H NMR (400 MHz, CDCl₃) δ4.54 (2H, d), 6.57 (1H, brt), 7.32–7.40 (7H, m), 7.63 (2H, d).
175: mp 158° C.; ¹H NMR (400 MHz, CDCl₃) δ4.63 (2H, d), 6.85 (1H, brs), 7.29–7.39 (7H, m), 7.64 (2H, d), 9.13 (1H, s).
176: mp 189–190° C.; ¹H NMR (400 MHz, CDCl₃) δ4.49 (2H, d), 6.57 (1H, brs), 7.25 (4H, d), 7.34 (4H, m).
177: mp 190° C.; ¹H NMR (400 MHz, CDCl₃) δ4.57 (2H, d), 6.82 (1H, brt), 7.17 (2H, d), 7.27 (2H, d), 7.35 (4H, m), 9.15 (1H, s).
178: mp 191–192° C.; ¹H NMR (400 MHz, CDCl₃) δ4.49 (2H, d), 6.6 (1H, brs), 7.19 (2H, d), 7.25 (2H, d), 7.35 (2H, d), 7.49 (2H, d).
179: mp 233–234° C.; ¹H NMR (400 MHz, CDCl₃) δ4.44 (2H, d), 7.49 (1H, d), 7.80 (4H, m), 8.14 (1H, s), 8.37 (1H, s), 9.0 (1H, brs).
180: ¹H NMR (400 MHz, CDCl₃) δ2.34 (3H, s), 4.49 (2H, d), 6.60 (1H, brs), 7.19 (4H, m), 7.25 (2H, d), 7.35 (2H, d).
181: ¹H NMR (400 MHz, CDCl₃) δ2.34 (3H, s), 4.58 (2H, d), 6.80 (1H, brs), 7.11 (2H, d), 7.18 (2H, d), 7.28 (2H, d), 7.33 (2H, d), 9.10(1H, brs).
182: mp 155–156° C.; ¹H NMR (400 MHz, CDCl₃) δ4.59 (2H, d), 6.85 (1H, brs), 7.27–7.36 (6H, m), 7.65 (2H, d), 9.2 (1H, s).
183: mp 228–233° C.; ¹H NMR (400 MHz, CDCl₃) δ4.50 (2H, d), 6.13 (1H, d), 6.90 (2H, d), 7.24 (2H, d), 7.34 (2H, d), 7.50 (2H, d), 7.6 (1H, brs), 9.03 (1H, s).
186: mp 239–241° C.; ¹H NMR (400 MHz, DMSO-d₆) δ4.47 (2H, d), 7.50 (1H, d), 6.83 (3H, m), 8.24 (2H, d), 8.39 (1H, d), 9.15 (1H, brt).
187: mp 187–188° C.; ¹H NMR (400 MHz, CDCl₃) δ4.58 (2H, d), 6.69 (1H, brs), 7.25 (2H, d), 7.34 (2H, d), 7.44 (2H, d), 7.64 (2H, d).
188: mp: 188–189° C.; ¹H NMR (400 MHz, CDCl₃) δ4.67 (2H, d), 6.90 (1H, t), 7.18 (2H, d), 7.36 (2H, d), 7.46 (2H, d), 7.62 (2H, d), 9.13 (1H, s).
189: mp 161–162° C.; ¹H NMR (400 MHz, CDCl₃) δ4.60 (2H, d), 6.70 (1H, brs), 7.39 (2H, d), 7.45 (2H, d), 7.64 (4H, m).
190: mp 172–176° C.; ¹H NMR (400 MHz, CDCl₃) δ4.68 (2H, d), 6.92 (1H, brt), 7.32 (2H, d), 7.47 (2H, d), 7.64 (4H, t), 9.13 (1H, s).
192: mp 140–141° C.; ¹H NMR (400 MHz, CDCl₃) δ2.64 (6H, s), 4.53 (2H, d), 7.08 (2H, d), 7.34 (1H, d), 7.37 (1H, bus), 7.47 (2H, d), 7.65 (1H, dd), 8.37 (1H, d), 11.15 (1H, s).
193: mp 153–154° C.; ¹H NMR (400 MHz, CDCl₃) δ2.16 (3H, s), 4.54 (2H, d), 6.88 (1H, ddd), 7.20 (1H, brd), 7.27 (1H, d), 7.31 (1H, t), 7.32 (2H, d), 7.63 (1H, ddd), 8.11 (1H, brs), 8.19 (1H, ddd).
194: mp 218° C.; ¹H NMR (400 MHz, CDCl₃) δ2.16 (3H, s), 4.53 (2H, d), 7.24 (2H, d), 7.26 (1H, d), 7.26 (1H, brt), 7.32 (2H, d), 7.42 (1H, dd), 7.48 (1H, brs), 8.19 (1H, d).
195: mp 224–225° C.; ¹H NMR (400 MHz, CDCl₃) δ2.16 (3H, s), 4.56 (2H, d), 7.25 (2H, d), 7.31(1H, d), 7.44 (1H, dd), 7.48 (1H, brs), 7.66 (1H, dd), 8.20 (1H, d), 8.37 (1H, d).
196: mp 169° C.; ¹H NMR (400 MHz, CDCl₃) δ2.20 (3H, s), 5.55 (2H, d), 7.26 (1H, d), 7.26 (1H, t), 7.27 (1H, d), 7.33 (1H, d), 7.82 (1H, dd), 8.35 (1H, brs), 8.44 (1H, d).

TABLE 8-continued

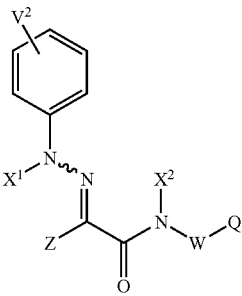

| No. | Q | V² | W | X¹ | X² | Z | E/Z |

197: mp 153–155° C.; ¹H NMR (400 MHz, CDCl₃) δ2.19 (3H, s), 4.56 (2H, d), 7.30 (1H, d), 7.30 (1H, d), 7.50 (1H, brt), 7.66 (1H, dd), 7.80 (1H, dd), 8.34 (1H, d), 8.43 (1H, s), 8.51 (1H, brs).
198: mp 125° C.; ¹H NMR (400 MHz, CDCl₃) δ2.22 (3H, s), 4.54 (2H, d), 7.19 (1H, d), 7.27 (2H, d), 7.30 (2H, d), 7.82 (1H, t), 8.50 (1H, brs), 8.73 (1H, d).
199: mp 151–152° C.; ¹H NMR (400 MHz, CDCl₃) δ2.33 (3H, s), 3.55 (3H, s), 4.56 (2H, d), 7.01 (1H, d), 7.32 (1H, d), 7.56 (1H, brt), 7.68 (1H, dd), 7.74 (1H, dd), 8.37 (1H, d), 8.52 (1H, s).
200: mp 113–114° C.; ¹H NMR (400 MHz, CDCl₃) δ2.34 (3H, s), 3.54 (3H, s), 4.54 (2H, d), 7.00 (1H, d), 7.27 (2H, d), 7.32 (2H, d), 7.47 (1H, brt), 7.72 (1H, dd), 8.51 (1H, brs).
201: mp 137–138° C.; ¹H NMR (400 MHz, CDCl₃) δ2.19 (3H, s), 4.76 (2H, d), 7.15 (2H, d), 7.4 (1H, brs), 7.50(5H, m), 7.61 (1H, s), 7.79 (1H, s), 7.85 (3H, m).
202: mp 162–163° C.; ¹H NMR (400 MHz, CDCl₃) δ2.14 (3H, s), 4.57 (2H, d), 6.28 (1H, dd), 6.35 (1H, dd), 7.15 (2H, d), 7.28 (1H, brt), 7.39 (1H, dd), 7.54 (2H, d), 7.64 (1H, brs).
203: mp 138–140° C.; ¹H NMR (400 MHz, CDCl₃) δ2.14 (3H, s), 2.29 (3H, s), 4.51 (2H, d), 5.91 (1H, dq), 6.15 (1H, d), 7.16 (2H, d), 7.23 (1H, brt), 7.54 (2H, d), 7.60 (1H, brs).
204: mp 158° C.; ¹H NMR (400 MHz, CDCl₃) δ1.54–1.64 (1H, m), 1.90–2.08 (3H, m), 2.13 (3H, s), 3.35 (1H, ddd), 3.64 (1H, ddd), 3.80 (1H, ddd), 3.92 (1H, ddd), 4.06 (1H, dddd), 7.18 (2H, d), 7.31 (1H, brt), 7.55 (2H, d), 7.60 (1H, brs).
205: mp 136–137° C.; ¹H NMR (400 MHz, CDCl₃) δ1.67 (1H, dddd), 2.05–2.14 (1H, m), 2.13 (3H, s), 2.58 (1H, dddddd), 3.41 (2H, dd), 3.63 (1H, dd), 3.77 (1H, ddd), 3.84 (1H, dd), 3.96 (1H, ddd), 7.17 (2H, d), 7.19 (1H, brt), 7.55 (2H, d), 7.70 (1H, brs).
206: mp 186° C.; ¹H NMR (400 MHz, CDCl₃) δ2.15 (3H, s), 4.69 (2H, d), 6.33 (1H, s), 7.18 (2H, d), 7.42 (1H, brt), 7.56 (2H, d), 7.68 (1H, brs).
207: mp 109–112° C.; ¹H NMR (400 MHz, CDCl₃) δ2.16 (3H, s), 4.75 (2H, d), 6.98 (1H, dd), 7.04 (1H, dd), 7.15 (2H, d), 7.24 (1H, dd), 7.32 (1H, brt), 7.53 (2H, d), 7.62 (1H, m).
208: mp 132° C.; ¹H NMR (400 MHz, CDCl₃) δ2.15 (3H, s), 4.63 (2H, dd), 6.77 (1H, d), 6.80 (1H, dt), 7.15 (2H, d), 7.32 (1H, brt), 7.55 (2H, d), 7.63 (1H, s).
209: ¹H NMR (400 MHz, CDCl₃) δ2.15 (3H, s), 4.44 (2H, d), 6.82 (1H, s), 7.17 (2H, d), 7.30 (1H, brt), 7.55 (2H, d), 7.69 (1H, brs).
210: ¹H NMR (400 MHz, CDCl₃) δ2.15 (3H, s), 4.70 (2H, d), 6.94 (1H, s), 7.13 (1H, s), 7.16 (1H, d), 7.34 (1H, brs), 7.55 (2H, d), 7.66 (1H, s).
211: ¹H NMR (400 MHz, CDCl₃) δ2.15 (3H, s), 4.65 (2H, d), 6.78 (1H, d), 6.91 (1H, d), 7.16 (2H, d), 7.32 (1H, brs), 7.55 (2H, d), 7.65 (1H, s).
212: mp 210° C.; ¹H NMR (400 MHz, CDCl₃) δ2.15 (3H, s), 4.66 (2H, dd), 7.16 (2H, d), 7.38 (1H, brt), 7.46 (1H, t), 7.55 (2H, d), 7.65 (1H, s).
213: mp 160° C.; ¹H NMR (400 MHz, CDCl₃) δ2.14 (3H, s), 2.72 (3H, s), 4.63 (2H, d), 7.03 (1H, s), 7.19 (2H, d), 7.54 (2H, d), 7.58 (1H, brt), 7.64 (1H, s).
214: mp 190° C.; ¹H NMR (400 MHz, CDCl₃) δ2.16 (3H, s), 4.70 (2H, d), 7.24 (2H, d), 7.24 (1H, brs), 7.32 (1H, d), 7.56 (2H, d), 7.63 (1H, s), 7.68 (1H, t), 8.04 (1H, brs), 8.61 (1H, d).
215: mp 184–185° C.; ¹H NMR (400 MHz, CDCl₃) δ2.18 (3H, s), 4.61 (2H, d), 7.17 (2H, d), 7.25 (1H, d), 7.42 (1H, brs), 7.55 (2H, d), 7.73 (1H, s), 8.57 (2H, m).
216: mp 163–164° C.; ¹H NMR (400 MHz, CDCl₃) δ2.18 (3H, s), 4.64 (2H, d), 6.85 (1H, s), 7.15 (1H, d), 7.18 (2H, d), 7.45 (1H, brs), 7.56 (2H, d), 7.68 (1H, s), 8.18 (1H, d).
217: mp 163–164° C.; ¹H NMR (400 MHz, CDCl₃) δ2.18 (3H, s), 4.59 (2H, d), 7.17 (3H, m), 7.27 (1H, d), 7.4 (1H, brt), 7.56 (2H, d), 7.68 (1H, s), 8.35 (1H, d).
218: mp 163–166° C.; ¹H NMR (400 MHz, CDCl₃) δ2.15 (3H, s), 4.65 (2H, d), 7.27 (2H, d), 7.56 (2H, d), 7.65 (2H, t), 8.08 (1H, brs).
219: mp 186° C.; ¹H NMR (400 MHz, CDCl₃) δ2.18 (3H, s), 4.57 (2H, d), 7.19 (2H, d), 7.22 (2H, s), 7.33 (1H, brt), 7.56 (2H, d), 7.69 (1H, s).

TABLE 8-continued $$\text{[Structure: V}^2\text{-phenyl-N(X}^1\text{)-N=C(Z)-C(=O)-N(X}^2\text{)-W-Q]}$$

| No. | Q | V² | W | X¹ | X² | Z | E/Z |
|---|---|---|---|---|---|---|---|

220: mp 193° C.; ¹H NMR (400 MHz, CDCl₃) δ2.18 (3H, s), 2.52 (3H, s), 4.54 (2H, d), 7.02 (1H, s), 7.09 (1H, s), 7.18 (2H, d), 7.39 (1H, brt), 7.56 (2H, d), 7.67 (1H, s).
221: mp 195–196° C.; ¹H NMR (400 MHz, CDCl₃) δ2.18 (3H, s), 3.48 (3H, s), 6.79 (1H, d), 7.23 (2H, d), 7.58 (2H, d), 7.66 (1H, dd), 7.78 (1H, brs), 8.47 (1H, d), 8.83 (1H, s).
222: mp 225° C.; ¹H NMR (400 MHz, CDCl₃) δ2.17 (3H, d), 4.85 (2H, d), 7.25 (1H, d), 7.59 (2H, d), 7.67 (1H, brs), 7.96 (1H, d), 8.35 (1H, brt), 8.81 (1H, d).
223: mp 196–201° C.; ¹H NMR (400 MHz, CDCl₃) δ1.17 (3H, t), 2.68 (2H, q), 4.75 (2H, d), 7.20 (2H, d), 7.56 (2H, d), 7.80 (1H, s), 7.85 (1H, brs), 8.52 (1H, d), 8.57 (1H, d), 8.66 (1H, s).
224: mp 220–221° C.; ¹H NMR (400 MHz, CDCl₃) δ2.15 (3H, s), 2.57 (3H, s), 4.70 (2H, d), 7.20 (2H, d), 7.56 (2H, d), 7.65 (1H, s), 7.83 (1H, brs), 8.44 (1H, d), 8.53 (1H, s).
225: ¹H NMR (400 MHz, CDCl₃) δ2.15 (3H, s), 4.57 (2H, d), 7.16 (2H, d), 7.42 (1H, brs), 7.56 (2H, d), 7.66 (1H, s), 8.65 (2H, s).
226: mp 185–186° C.; ¹H NMR (400 MHz, CDCl₃) δ2.15 (3H, s), 4.86 (2H, d), 7.15 (2H, d), 7.50 (1H, d), 7.56 (3H, m), 7.68 (1H, s), 7.87 (1H, brs).
227: mp 195–196° C.; ¹H NMR (400 MHz, CDCl₃) δ4.55 (2H, d), 6.95 (1H, brt), 7.13 (2H, d), 7.17 (1H, s), 7.18 (1H, d), 7.42 (1H, d), 7.55 (2H, d), 8.20 (1H, s).
228: mp 160–162° C.; ¹H NMR (400 MHz, CDCl₃) δ4.55 (2H, d), 6.97 (2H, t), 7.05 (2H, d), 7.11 (1H, d), 7.26–7.31 (6H, m).
229: mp 178° C.; ¹H NMR (400 MHz, CDCl₃) δ2.29 (3H, s), 4.55 (2H, d), 6.95 (2H, d), 6.96 (1H, brt), 7.08 (1H, d), 7.09 (2H, d), 7.26–7.33 (4H, m), 8.01 (1H, s).
230: mp 197–199° C.; ¹H NMR (400 MHz, DMSO-d₆) δ4.39 (2H, d), 7.28 (1H, s), 7.31–7.40 (6H, m), 7.58 (2H, d), 9.80(1H, t).
231: mp 199–201° C.; ¹H NMR (400 MHz, CDCl₃) δ2.36 (3H, s), 4.55 (2H, d), 6.90 (1H, t), 7.10 (2H, d), 7.18 (2H, d), 7.18 (1H, brs), 7.25 (2H, d), 7.52 (2H, d), 8.20 (1H, brs).
232: mp 110–111° C.; ¹H NMR (400 MHz, CDCl₃) δ4.57 (2H, d), 7.02 (1H, brt), 7.18 (3H, d), 7.43 (2H, d), 7.58 (2H, d), 8.28 (1H, s).
233: mp 144–145° C.; ¹H NMR (400 MHz, CDCl₃) δ2.36 (3H, s), 4.58 (2H, d), 6.95 (1H, brt).
234: mp 135–137° C.; ¹H NMR (400 MHz, CDCl₃) δ3.78 (3H, s), 4.59 (2H, d), 7.15 (1H, brt), 7.20 (1H, d), 7.32 (1H, d), 7.59 (2H, d), 7.69 (1H, dd), 8.37 (1H, d).
235: mp 144–146° C.; ¹H NMR (400 MHz, CDCl₃) δ2.13 (3H, s), 4.50 (2H, d), 6.95 (2H, t), 7.05 (2H, d), 7.26 (2H, d), 7.35 (1H, brt), 7.49 (1H, s).
236: n_D²⁵ 1.5489; ¹H NMR (400 MHz, CDCl₃) δ2.17 (3H, s), 4.52 (2H,d), 6.96 (1H, t), 7.17 (2H, d), 7.37 (1H, brt), 7.55 (2H, d), 7.66 (1H, brs).
237: n_D²⁵ 1.5227; ¹H NMR (400 MHz, CDCl₃) δ2.17 (3H, s), 4.55 (2H, d), 7.06–7.17 (4H, m), 7.36 (1H, t), 7.36 (1H, brt), 7.55 (2H, d), 7.64 (1H, brs).
238: mp 103–105° C.; ¹H NMR (400 MHz, CDCl₃) δ2.17 (3H, s), 4.53 (2H, d), 7.09–7.17 (4H, m), 7.30 (1H, brt), 7.37 (1H, dd), 7.55 (2H, d), 7.62 (1H, s).
239: mp 165° C.; ¹H NMR (400 MHz, CDCl₃) δ2.17 (3H, s), 3.89 (3H, s), 4.54 (2H, d), 6.82 (1H, m), 6.92 (1H, dd), 6.96 (1H, dd), 7.15 (2H, d), 7.30 (1H, brt), 7.54 (2H, d), 7.62 (1H, s).
240: mp 159–160° C.; ¹H NMR (400 MHz, CDCl₃) δ2.13 (3H, s), 4.54 (2H, d), 6.69–6.74 (1H, m), 6.97 (1H, ddd), 7.07 (1H, ddd), 7.26 (1H, brt), 7.27 (2H, d), 7.31 (2H, d), 7.39 (1H, brs).
241: mp 176–177° C.; ¹H NMR (400 MHz, CDCl₃) δ2.12 (3H, s), 4.57 (2H, d), 6.69–6.75 (1H, m), 6.98 (1H, dd), 7.08 (1H, d), 7.30 (1H, d), 7.32 (1H, brt), 7.43 (1H, s), 7.66 (1H, dd), 8.37 (1H, d).
242: mp 180–183° C.; ¹H NMR (400 MHz, CDCl₃) δ2.12 (3H, s), 4.54 (2H, d), 6.89 (1H, ddd), 7.06 (1H, dd), 7.17 (1H, dd), 7.27 (2H, d), 7.28 (1H, brt), 7.32 (2H, d), 7.41 (1H, s).
243: mp 166–169° C.; ¹H NMR (400 MHz, CDCl₃) δ2.12 (3H, s), 4.57 (2H, d), 6.90 (1H, ddd), 7.07 (1H, dd), 7.18 (1H, dd), 7.30 (1H, d), 7.35 (1H, brt), 7.45 (1H, s), 7.67 (1H, dd), 8.37 (1H, d).
244: mp 129–130° C.; ¹H NMR (400 MHz, CDCl₃) δ2.18 (3H, s), 4.51 (2H, d), 7.23 (2H, d), 7.31 (1H, d), 7.33 (1H, brs), 7.50 (1H, brt).
245: ¹H NMR (400 MHz, CDCl₃) δ2.20 (3H, s), 4.52 (2H, d), 6.17 (1H, brt), 7.25 (2H, d), 7.34 (2H, d), 12.29 (1H, brs).
246: mp 118° C.; ¹H NMR (400 MHz, CDCl₃) δ(E isomer) 2.18 (3H, s), 4.53 (2H, d), 7.30 (1H, d), 7.37 (1H, brt), 7.52 (1H, brt), 7.63 (1H, dd), 8.35 (1H, d).
247: mp 197° C.; ¹H NMR (400 MHz, CDCl₃) δ2.16 (3H, s), 4.55 (2H, d), 6.89 (1H, d), 7.03 (1H, ddd), 7.06 (1H, brs), 7.27 (2H, d), 7.29 (1H, brt), 7.32 (1H, d), 7.62 (1H, s).
248: mp 208° C.; ¹H NMR (400 MHz, CDCl₃) δ2.15 (3H, s), 4.58 (2H, d), 6.90 (1H, d), 7.05 (1H, ddd), 7.06 (1H, brs), 7.30 (1H, d), 7.34 (1H, brt), 7.64 (1H, s), 7.67 (1H, dd), 8.38 (1H, d).
249: mp 207° C.; ¹H NMR (400 MHz, CDCl₃) δ2.16 (3H, s), 4.57 (2H, d), 6.72 (2H, d), 7.31 (1H, d), 7.36 (1H, brt), 7.67 (1H, dd), 7.95 (1H, brs), 8.38 (1H, d).
250: mp 169° C.; ¹H NMR (400 MHz, CDCl₃) δ2.16 (3H, s), 4.58 (2H, d, J = 6.4 Hz), 6.98 (1H, dd, J = 2.4, 8.4 Hz), 7.25 (1H, s), 7.31 (1H, d, J = 8.4 Hz), 7.36 (1H, brt, J = 6.4 Hz), 7.58 (1H, d, J = 8.4 Hz), 7.64 (1H, s), 7.67 (1H, dd, J = 2.8, 8.4 Hz), 8.38 (1H, d, J = 2.8 Hz).
251: mp 206–208° C.; ¹H NMR (400 MHz, CDCl₃) δ2.16 (3H, s), 4.58 (2H, d, J = 6.4 Hz), 7.12 (2H, s), 7.31 (1H, d, J = 8.4 Hz), 7.33 (1H, brt, J = 6.4 Hz), 7.62 (1H, s), 7.67 (1H, dd, J = 2.8, 8.4 Hz), 8.38 (1H, d, J = 2.8 Hz).
252: ¹H NMR (400 MHz, CDCl₃) δ2.16 (3H, s), 4.54 (2H, d), 7.24 (2H, d), 7.29 (1H, brt), 7.30 (1H, d), 7.59 (2H, s), 7.95 (1H, s).
253: mp 144–148° C.; ¹H NMR (400 MHz, CDCl₃) δ2.20 (3H, s), 4.51 (2H, d), 6.14 (1H, brt), 7.25 (2H, d), 7.34 (2H, d), 7.62 (2H, d), 13.21 (1H, s).
254: mp 204° C.; ¹H NMR (400 MHz, CDCl₃) δ7.17 (3H, s), 4.58 (2H, d), 7.29 (1H, brt), 7.31 (2H, d), 7.59 (2H, s), 7.67 (1H, s), 7.73 (1H, s), 8.38 (1H, d).
255: ¹H NMR (400 MHz, CDCl₃) δ2.15 (3H, s), 4.54 (2H, d), 7.12 (1H, dd), 7.27 (2H, d), 7.28 (1H, brt), 7.31 (2H, d), 7.38 (1H, d), 7.57 (1H, s), 7.58 (1H, d).
256: mp 189–191° C.; ¹H NMR (400 MHz, CDCl₃) δ2.15 (3H, s), 4.57 (2H, d), 7.13 (1H, dd), 7.31 (1H, d), 7.31 (1H, brt), 7.39 (1H, d), 7.57 (1H, s), 7.59 (1H, d), 7.67 (1H, dd), 8.38 (1H, d).
257: mp 177° C.; ¹H NMR (400 MHz, CDCl₃) δ2.12 (3H, s), 4.56 (2H, d), 6.87 (2H, d), 7.30 (1H, d), 7.34 (1H, brt), 7.47 (1H, brs), 7.57 (2H, d), 7.66 (1H, dd), 8.36 (1H, d).
258: mp 176° C.; ¹H NMR (400 MHz, CDCl₃) δ2.19 (3H, s), 4.58 (2H, d, J = 6.4 Hz), 7.31 (1H, d, J=8.0 Hz), 7.33 (1H, d, J = 8.0 Hz), 7.34 (1H, brt, J = 6.4 Hz), 7.48 (1H, d, J = 2.0 Hz), 7.67 (1H, dd, J = 2.8, 8.0 Hz), 7.75 (1H, d, J = 8.8 Hz), 7.79 (1H, s), 8.38 (1H, d, J = 2.8 Hz).
259: mp 163–164° C.; ¹H NMR (400 MHz, CDCl₃) δ2.20 (3H, s), 4.53 (2H, d, J = 6.0 Hz), 6.17(1H, brt, J=6.0 Hz), 7.19(2H, d, J = 8.4 Hz), 7.33 (1H, d, J = 8.4 Hz), 7.50 (2H, d, J = 8.4 Hz), 7.66 (1H, dd, J = 2.4, 8.4 Hz), 8.36 (1H, d, J = 2.4 Hz), 12.97 (1H, s).
260: mp 150° C.; ¹H NMR (400 MHz, CDCl₃) δ2.16 (3H, s), 4.57 (2H, d), 7.17 (2H, d), 7.31 (1H, d), 7.36 (1H, brt), 7.51 (2H,), 7.66 (1H, s), 7.67 (1H, dd), 8.37 (1H, d).
261: mp 207–210° C.; ¹H NMR (400 MHz, CDCl₃) δ2.16 (3H, s), 4.58 (2H, d), 7.19 (2H, d), 7.31 (1H, d), 7.40 (1H, brt), 7.56 (1H, d), 7.60 (1H, s), 7.66 (2H, d), 7.67 (1H, s), 7.68 (1H, dd), 8.39 (1H, d).
262: mp 175° C.; ¹H NMR (400 MHz, CDCl₃) δ2.16 (3H, s), 4.57 (2H, d), 6.84 (2H, d), 6.98 (1H, d), 7.37 (1H, d), 7.50 (1H, dd), 7.68 (1H, s), 7.79 (1H, s), 8.29 (1H, s).
263: mp 183° C.; ¹H NMR (400 MHz, CDCl₃) δ2.17 (3H, s), 4.57 (2H, d, J = 6.4 Hz), 6.71 (2H, d, J=11.2 Hz), 7.36(1H, brt, J = 6.4 Hz), 7.71 (1H, s), 7.79 (1H, d, J = 2.4 Hz), 8.29 (1H, d, J = 2.4 Hz).

TABLE 8-continued

[Structure diagram: phenyl group with V² substituent connected to N-X¹ and N=, with Z and C(=O)-N(X²)-W-Q chain]

| No. | Q | V² | W | X¹ | X² | Z | E/Z |

264: mp 151° C.; ¹H NMR (400 MHz, CDCl₃) δ2.12 (3H, s), 4.52 (2H, d, J = 6.0 Hz), 6.44 (1H, brs), 6.72 (2H, d, J = 11.2 Hz), 7.78 (1H, d, J=2.0 Hz), 8.25 (1H, d, J = 2.0 Hz), 13.00 (1H, d, J = 2.0 Hz).
265: n_D²⁵ 1.5748; ¹H NMR (400 MHz, CDCl₃) δ2.16(3H, s), 4.52 (2H,), 7.16 (2H, d), 7.25 (1H, d), 7.34 (1H, brt), 7.42 (1H, d), 7.54–7.59 (3H, m), 7.66 (1H, s).
266: mp 136° C.; ¹H NMR (400 MHz, CDCl₃) δ2.17 (3H, s), 2.39 (3H, s), 4.50 (2H, d), 7.02 (1H, d), 7.15 (2H, d), 7.20 (1H, s), 7.30 (1H, brt), 7.48–7.54 (3H, m), 7.67 (1H, s).
267: mp 157° C.; ¹H NMR (400 MHz, CDCl₃) δ2.11 (3H, s), 2.26 (3H, s), 2.27 (3H, s), 4.52 (2H, d), 7.12 (5H, m), 7.20 (1H, rt), 7.52 (2H, d), 7.60 (1H, s).
268: mp 144–145° C.; ¹H NMR (400 MHz, CDCl₃) δ1.21 (3H, t), 2.12 (3H, s), 2.31 (6H, s), 2.59 (2H, q), 4.50 (2H, d), 6.92 (1H, d), 6.95 (2H, s), 7.01 (2H, d), 7.11 (2H, d), 7.29 (1H, rt), 7.39 (1H, s).
269: mp 176–177° C.; ¹H NMR (400 MHz, CDCl₃) δ2.13 (3H, s), 4.63 (2H, d), 7.03 (2H, d), 7.26 (2H, d), 7.40 (1H, brt), 7.43 (2H, d), 7.48 (1H, s), 7.64 (2H, d).
270: mp 193–194° C.; ¹H NMR (400 MHz, CDCl₃) δ2.17 (3H, s), 4.64 (2H, d), 7.16 (2H, d), 7.42 (1H, brt), 7.44 (2H, d), 7.55 (2H, d), 7.64 (2H, d), 7.64 (1H, brs).
271: mp 170° C.; ¹H NMR (400 MHz, CDCl₃) δ2.14 (3H, s), 3.91 (3H, s), 4.64 (2H, d), 7.03 (2H, d), 7.24 (2H, d), 7.35 (1H, brt), 7.40 (2H, d), 7.47 (1H, s), 8.02 (2H, d).
272: mp 173° C.; ¹H NMR (400 MHz, CDCl₃) δ2.14 (3H, s), 4.67 (2H, d), 7.04 (2H, d), 7.27 (2H, d), 7.45 (1H, brt), 7.49 (3H, m), 8.20 (2H, d).
273: mp 79–80° C.; ¹H NMR (400 MHz, CDCl₃) δ2.13 (3H, s), 3.89 (3H, s), 4.49 (2H, d), 5.58 (1H, s), 6.87 (3H, m), 7.00 (2H, d), 7.23 (2H, d), 7.23 (1H, brt), 7.43 (1H, s).
274: mp 180–181° C.; ¹H NMR (400 MHz, CDCl₃) δ2.13 (3H, s), 3.88 (6H, s), 4.51 (2H, d), 6.84 (3H, m), 7.01 (2H, d), 7.23 (2H, d), 7.24 (1H, brt), 7.42 (1H, s).
275: mp 115–116° C.; ¹H NMR (400 MHz, CDCl₃) δ2.16 (3H, s), 4.53 (2H, d), 4.76 (2H, q), 6.85 (1H, d), 7.14 (2H, d), 7.26 (1H, brt), 7.54 (2H, d), 7.60 (1H, s), 7.66 (1H, s), 8.12 (1H, s).
276: mp 101–102° C.; ¹H NMR (400 MHz, CDCl₃) δ2.14 (3H, s), 4.54 (2H, d), 7.00–7.03 (6H, m), 7.24–7.31 (8H, m), 7.44 (1H, s).
277: mp 175° C.; ¹H NMR (400 MHz, CDCl₃) δ2.16 (3H, s), 4.54 (2H, d), 6.89 (1H, d), 7.14 (4H, m), 7.18 (1H, t), 7.30 (1H, rt), 7.40 (2H, t), 7.54 (2H, d), 7.60 (1H, s), 7.73 (1H, dd), 8.17 (1H, d).
278: mp 135–136° C.; ¹H NMR (400 MHz, CDCl₃) δ2.13 (3H, s), 4.55 (2H, d), 6.92–7.03 (6H, m), 7.24–7.30 (7H, m), 7.43 (1H, s).
279: mp 199–200° C.; ¹H NMR (400 MHz, CDCl₃) δ2.13 (3H, s), 2.33 (3H, s), 4.54 (2H, d), 6.91 (2H, d), 6.95 (2H, d), 7.02 (2H, d), 7.15 (2H, d), 7.23–7.29 (5H, m), 7.43 (1H, s).
280: mp 136° C.; ¹H NMR (400 MHz, CDCl₃) δ2.14 (3H, s), 4.58 (2H, d), 7.02–7.05 (6H, m), 7.25 (1H, brt), 7.34 (2H, d), 7.35 (2H, d), 7.46 (1H, s), 7.57 (2H, d).
281: mp 151° C.; ¹H NMR (400 MHz, CDCl₃) δ2.13 (3H, s), 3.80 (2H, dt), 4.13 (2H, t), 6.94 (2H, d), 6.98 (1H, t), 7.16 (2H, d), 7.31 (2H, dd), 7.44 (1H, brt), 7.54 (2H, d), 7.60 (1H, s).
282: mp 163° C.; ¹H NMR (400 MHz, CDCl₃) δ2.13 (3H, s), 3.77 (1/2H, dt), 3.78 (3/2H, dt), 4.09 (1/2H, t), 4.10 (3/2H, t), 6.86 (2H, d), 7.03 (1/2H, d), 7.15 (3/2H, d), 7.24 (1H, d), 7.37 (1H, brt), 7.40 (1/2H, d), 7.54 (1H, s), 7.57 (3/2H, d).
283: mp 166–168° C.; ¹H NMR (400 MHz, CDCl₃) δ2.13 (3H, s), 3.80 (2H, dt), 4.15 (2H, t), 7.17 (2H, d), 7.21 (2H, d), 7.24 (2H, dd), 7.40 (1H, brt), 7.53 (2H, d), 7.84 (1H, dd), 8.08 (1H, dd).
284: mp 111° C.; ¹H NMR (400 MHz, CDCl₃) δ2.17 (3H, s), 6.19 (1H, d, J = 3.2 Hz), 6.94 (2H, d, J=8.4 Hz), 7.23 (2H, d, J = 8.4 Hz), 7.49 (2H, d, J = 8.4 Hz), 7.59 (2H, d, J = 8.4 Hz), 7.75 (1H, s), 8.57 (1H, d, J = 3.2 Hz).
285: mp 160–163° C.; ¹H NMR (400 MHz, CDCl₃) δ2.13 (3H, s), 5.00 (2H, s), 7.03 (2H, d), 7.40–7.44 (3H, m), 7.45–7.49 (2H, m), 7.51 (2H, d), 7.62 (1H, s), 9.15 (1H, s).
286: mp 149° C.; ¹H NMR (400 MHz, CDCl₃) δ2.13 (3H, s), 4.96 (2H, s), 7.06 (2H, d), 7.37 (2H, d), 7.40 (2H, d), 7.54 (2H, d), 7.66 (1H, s), 9.16 (1H, s).
287: mp 116–122° C.; ¹H NMR (400 MHz, CDCl₃) δ2.24 (3H, s), 3.34 (3H, s), 4.50 (2H, d), 6.96 (2H, t), 7.05 (2H, d), 7.55 (2H, d), 7.57 (1H, brt).
288: mp 94–95° C.; ¹H NMR (400 MHz, CDCl₃) δ2.24 (3H, s), 3.33 (3H, s), 4.53 (2H, d), 7.04 (2H, d), 7.06 (2H, d), 7.13 (1H, d), 7.36 (1H, t), 7.55 (2H, d), 7.56 (1H, brt).
289: mp 151° C.; ¹H NMR (400 MHz, CDCl₃) δ2.26 (3H, s), 3.30 (3H, s), 4.56 (2H, d), 6.74 (1H, dd), 6.76 (1H, dd), 7.31 (1H, d), 7.49 (1H, dd), 7.55 (1H, brs), 7.67 (1H, dd), 8.38 (1H, d).
290: mp 155° C.; ¹H NMR (400 MHz, CDCl₃) δ2.27 (3H, s), 3.27 (3H, s), 4.56 (2H, d), 6.52 (2H, d), 7.32 (1H, d), 7.52 (1H, brt), 7.67 (1H, dd), 8.38 (1H, d).
291: mp 105–106° C.; ¹H NMR (400 MHz, CDCl₃) δ2.24 (3H, s), 3.33 (3H, s), 4.55 (2H, d), 7.05 (2H, d), 7.31 (1H, d), 7.51 (2H, d), 7.60 (1H, brt), 7.67 (1H, dd), 8.37 (1H, d).
292: mp 143–144° C.; ¹H NMR (400 MHz, CDCl₃) δ2.27 (3H, s), 3.32 (3H, s), 4.56 (2H, d), 6.76 (2H, d), 6.78 (1H, d), 7.50 (1H, dd), 7.59 (1H, brt), 7.80 (1H, d), 8.29 (1H, d).
293: mp 131° C.; ¹H NMR (400 MHz, CDCl₃) δ2.23 (3H, s), 3.34 (3H, s), 4.55 (2H, d), 7.05 (2H, d), 7.55 (2H, d), 7.62 (1H, brt), 7.80 (1H, s), 8.29 (1H, s).
294: ¹H NMR (400 MHz, CDCl₃) δ 1.22 (6H, d), 1.81 (3H, s), 3.97 (1H, septet), 4.57 (2H, d), 6.59 (1H, d), 6.62 (1H, d), 7.34 (1H, dd), 7.47 (1H, dd), 7.62 (1H, brt), 7.69 (1H, dd), 8.39 (1H, d).
295: mp 106° C.; ¹H NMR (400 MHz, CDCl₃) δ1.23 (6H, d), 1.80 (3H, s), 3.97 (1H, septet). 4.56 (2H, d), 6.60 (1H, d), 6.64 (1H, d), 7.48 (1H, dd), 7.65 (1H, brt), 7.82 (1H, dd), 8.29 (1H, d).
296: mp 112–114° C.; ¹H NMR (400 MHz, CDCl₃) δ1.24 (6H, d), 1.68 (3H, s), 3.89 (1H, m), 4.56 (2H, d), 6.93 (2H, d), 7.54 (2H, d), 7.65 (1H, brt), 7.81 (1H, s), 8.30 (1H, s).
297: ¹H NMR (400 MHz, CDCl₃) δ1.48 (9H, s), 1.98 (3H, s), 4.52 (2H, d, J = 6.4 Hz), 7.30 (1H, d, J = 8.4 Hz), 7.37 (2H, d, J = 8.4 Hz), 7.61 (2H, d, J = 8.4 Hz), 7.64 (1H, dd, J = 2.4, 8.4 Hz), 7.69 (1H, brt, J = 6.4 Hz), 8.35 (1H, d, J = 2.4 Hz).
298: mp 128–129° C.; ¹H NMR (400 MHz, CDCl₃) δ1.19 (3H, t), 2.73 (2H, q), 3.34 (3H, s), 4.55 (2H, d), 7.01 (2H, d), 7.32 (1H, d), 7.54 (3H, d), 7.66 (1H, dd), 8.38 (1H, d).
299: mp 115–116° C.; ¹H NMR (400 MHz, CDCl₃) δ0.84 (3H, t), 1.20 (6H, d), 2.25 (2H, q), 3.86 (1H, m), 4.57 (2H, d), 6.96 (2H, d), 7.33 (1H, d), 7.52 (2H, d), 7.60 (1H, brt), 7.68 (1H, dd), 8.39 (1H, d).
300: mp 175–176° C.; ¹H NMR (400 MHz, CDCl₃) δ4.49 (2H, d), 6.68 (1H, brt), 7.17 (1H, d), 7.43 (4H, m), 7.64 (2H, d).
301: mp 188–189° C.; ¹H NMR (400 MHz, CDCl₃) δ4.58 (2H, d), 7.23 (1H, d), 7.23 (1H, brs), 7.32 (1H, d), 7.39 (1H, d), 7.54 (2H, m), 7.72 (1H, dd), 8.38 (1H, d).
302: mp 211° C.; ¹H NMR (400 MHz, CDCl₃) δ2.36 (3H, s), 4.58 (2H, d), 6.80 (1H, brt), 7.10–7.30 (6H, m), 7.64 (2H, d), 9.10 (1H, brs).
303: mp 185–189° C.; ¹H NMR (400 MHz, DMSO-d₆) δ4.52 (2H, d), 7.50 (2H, d), 7.71 (2H, d), 7.82 (4H, m), 9.08 (1H, brt).
304: mp 103° C.; ¹H NMR (400 MHz, CDCl₃) δ2.96 (3H, s), 4.50 (2H, d), 5.13 (1H, brd), 7.06 (2H, m), 7.16 (2H, m), 7.42 (2H, m), 7.50 (2H, d), 7.50 (1H, brs).
305: n_D²⁵ 1.6149; ¹H NMR (400 MHz, CDCl₃) δ2.90 (3H, s), 4.51 (2H, d), 4.90 (1H, brd), 6.89 (1H, t), 7.02 (3H, m), 7.24–7.33 (6H, m), 7.5 (1H, brs).
306: mp 90–93° C.; ¹H NMR (400 MHz, CDCl₃) δ2.26 (3H, s), 3.02 (3H, s), 4.51 (2H, d), 5.25 (1H, brd), 7.00 (1H, d), 7.10 (1H, s), 7.23 (4H, m), 7.32 (2H, d), 7.32 (1H, brs), 7.51 (1H, brs).
307: n_D²⁵ 1.5520; ¹H NMR (400 MHz, CDCl₃) δ2.96 (3H, s), 4.52 (2H, d), 5.16 (1H, brd), 7.04 (2H, d), 7.15 (1H, s), 7.25 (2H, d), 7.33 (2H, d), 7.49 (2H, d), 7.49 (1H, brs).

TABLE 8-continued

|       |   |    |   |    |   |     |
|-------|---|----|---|----|---|-----|
| No.   | Q | V² | W | X¹ | X² | Z | E/Z |

308: $n_D^{25}$ 1.5662; ¹H NMR (400 MHz, CDCl₃) δ2.35 (3H, s), 2.94 (3H, d), 4.51 (2H, d), 5.20 (1H, brd), 7.03 (2H, d), 7.17 (3H, m), 7.21 (2H, d), 7.44 (1H, brs), 7.47 (2H, d).
309: mp 116–118° C.; ¹H NMR (400 MHz, CDCl₃) δ3.00 (3H, d), 3.03 (3H, s), 4.51 (2H, d), 6.15 (1H, brd), 6.86 (2H, d), 7.32 (1H, d), 7.48 (2H, d), 7.64 (1H, dd), 8.13 (1H, brt), 8.37 (1H, d).
310: mp 157–164° C.; ¹H NMR (400 MHz, CDCl₃) δ1.54–1.64 (6H, m), 2.89–3.08 (4H, m), 4.52 (2H, d), 7.08 (2H, d), 7.34 (1H, d), 7.47 (2H, d), 7.50 (1H, d), 7.65 (1H, dd), 8.37 (1H, d).
311: mp 160–167° C.; ¹H NMR (400 MHz, CDCl₃) δ3.18 (4H, m), 3.83 (4H, m), 4.53 (2H, d), 7.12 (2H, d), 7.32 (1H, d), 7.53 (2H, d), 7.65 (1H, m), 8.37 (1H, d), 8.70 (1H, d).
312: mp 211° C.; ¹H NMR (400 MHz, DMSO-d₆) δ2.11 (3H, s), 4.40(2H, d), 7.18 (1H, ddd), 7.33 (2H, d), 7.39 (2H, d), 7.48 (1H, brs), 7.75 (1H, ddd), 8.42 (1H, brt).
313: mp 204–206° C.; ¹H NMR (400 MHz, DMSO-d₆) δ2.10 (3H, s), 4.43 (2H, d), 7.17 (1H, ddd), 7.47 (1H, brt), 7.73 (1H, brt), 7.79 (1H, dd), 8.37 (1H, d).
314: mp 219° C.; ¹H NMR (400 MHz, DMSO-d₆) δ2.12 (3H, s), 4.40 (2H, d), 7.33 (2H, d), 7.34–7.39 (3H, m), 7.39 (2H, d), 7.93 (1H, d), 8.42 (1H, brt).
315: mp 249° C.; ¹H NMR (400 MHz, DMSO-d₆) δ2.11 (3H, s), 4.42 (2H, d), 7.35 (1H, dd), 7.43 (1H, brt), 7.49 (1H, dd), 7.79 (1H, dd), 7.91 (1H, brs), 8.36 (1H, d), 8.51 (1H, brt).
316: mp 222° C.; ¹H NMR (400 MHz, DMSO-d₆) δ2.13 (3H, d), 4.40 (2H, d), 7.34 (2H, d), 7.40 (2H, d), 7.58–7.71 (3H, m), 8.21 (1H, brs), 8.49 (1H, brt).
317: mp 247° C.; ¹H NMR (400 MHz, DMSO-d₆) δ2.12 (3H, s), 4.43 (2H, d), 7.50 (1H, d), 7.55 (1H, s), 7.63 (1H, brd), 7.80 (1H, dd), 8.21 (1H, brs), 8.38 (1H, d), 8.54 (1H, brt).
318: mp 180–183° C.; ¹H NMR (400 MHz, CDCl₃) δ7.46 (2H, d), 7.09–7.41 (4H, m), 7.46 (1H, s), 7.54 (2H, d), 8.55 (1H, brs).
319: mp 97–114° C.; ¹H NMR (400 MHz, CDCl₃) δ4.70 (2H, d), 7.15 (1H, brd), 7.21 (2H, d), 7.49 (1H, s), 7.59 (2H, d), 8.33 (1H, s).
320: mp 202° C.; ¹H NMR (400 MHz, CDCl₃) δ2.11 (3H, s), 4.65 (2H, dd, J = 0.8, 6.4 Hz), 6.70–6.75 (1H, m), 6.99 (1H, ddd, J = 2.8, 6.8, 12.0 Hz), 7.09 (1H, ddd, J = 8.8, 8.8, 9.6 Hz), 7.33 (1H, brt, J = 6.4 Hz), 7.42 (1H, s), 7.46 (1H, t, J = 0.8 Hz).
321: mp 176° C.; ¹H NMR (400 MHz, CDCl₃) δ2.12 (3H, s), 4.65 (2H, d, J = 6.0 Hz), 6.73 (2H, dd, J = 6.0, 9.2 Hz), 7.35 (1H, brt, J = 6.0 Hz), 7.46 (1H, s), 7.61 (1H, s).
322: mp 177–178° C.; ¹H NMR (400 MHz, CDCl₃) δ2.11 (3H, s), 4.65 (2H, dd, J = 0.8, 6.0 Hz), 6.90 (1H, ddd, J = 2.8, 4.0, 9.2 Hz), 7.08 (1H, dd, J = 8.4, 9.2 Hz), 7.19 (1H, dd, J = 2.8, 6.0 Hz), 7.37 (1H, brt, J = 6.0 Hz), 7.45 (1H, s), 7.46 (1H, t, J = 0.8 Hz).
323: mp 198° C.; ¹H NMR (400 MHz, CDCl₃) δ2.16 (3H, s), 4.66 (2H, d), 6.84 (1H, d), 6.99 (1H, d), 7.35 (1H, brt), 7.48 (1H, s), 7.52 (1H, d), 7.66 (1H, s).
324: mp 146° C.; ¹H NMR (400 MHz, CDCl₃) δ2.16 (3H, s), 4.66 (2H, d, J = 6.4 Hz), 6.72 (1H, d, J=10.8 Hz), 7.34 (1H, brt, J = 6.4 Hz), 7.47 (1H, s), 7.81 (1H, s).
325: mp 167–168° C.; ¹H NMR (400 MHz, CDCl₃) δ2.15 (3H, s), 4.66 (2H, dd , J = 0.8, 6.4 Hz), 6.91 (1H, brd, J = 8.4 Hz), 7.05 (1H, ddd, J = 2.0, 2.0, 1.0 Hz), 7.08 (1H, brs), 7.36 (1H, brt, J = 6.4 Hz), 7.47 (1H, t, J = 0.8 Hz), 7.68 (1H, s).
326: mp 164° C.; ¹H NMR (400 MHz, CDCl₃) δ2.13 (3H, s), 4.65 (2H, dd, J = 0.8, 6.4 Hz), 7.15 (1H, dd, J = 9.2, 9.2 Hz), 7.24 (1H, dd, J = 2.4, 3.6, 9.2 Hz), 7.29 (1H, dd, J = 2.4, 6.0 Hz), 7.33 (1H, brt, J = 6.4 Hz), 7.46 (1H, t, J = 0.8 Hz), 7.53 (1H, s).
327: mp 162° C.; ¹H NMR (400 MHz, CDCl₃) δ2.12 (3H, s), 4.65 (2H, dd, J = 0.8, 6.4 Hz), 6.90 (1H, dd, J = 2.8, 8.8 Hz), 7.25 (1H, d, J = 2.8 Hz), 7.34 (1H, d, J = 8.8 Hz), 7.36 (1H, brt, J = 6.4 Hz), 7.46 (1H, s).
328: mp 209° C.; ¹H NMR (400 MHz, CDCl₃) δ2.16 (3H, s), 4.67 (2H, d, J = 5.6 Hz),. 6.98 (1H, dd, J 2.4, 8.8 Hz), 7.26 (1H, brs), 7.37 (1H, brt, J = 5.6 Hz), 7.48 (1H, s), 7.59 (1H, d, J = 8.8 Hz), 7.63 (1H, s).
329: mp 182° C.; ¹H NMR (400 MHz, CDCl₃) δ2.15 (3H, s), 4.67 (2H, d, J = 6.4 Hz), 7.13 (2H, s), 7.34 (1H, brt, J=6.4 Hz), 7.48 (1H, s), 7.64 (1H, s).
330: mp 118° C.; ¹H NMR (400 MHz, CDCl₃) δ2.14 (3H, s), 4.66 (2H, dd, J = 0.8, 6.0 Hz), 7.21 (1H, dd, J = 2.8, 8.4 Hz), 7.33 (1H, brt, J = 6.0 Hz), 7.39 (1H, d, J = 2.8 Hz), 7.41 (1H, d, J = 8.4 Hz), 7.46 (1H, t, J = 0.8 Hz), 7.64 (1H, brs).
331: mp 183–185° C.; ¹H NMR (400 MHz, CDCl₃) δ2.11 (3H, s), 4.64 (2H, dd, J = 0.8, 6.0 Hz), 6.98(2H, d, J = 8.8 Hz), 7.35 (1H, brt, J = 6.0 Hz), 7.40 (2H, d, J = 8.8 Hz), 7.45 (1H, t, J = 0.8 Hz), 7.48 (1H, s).
332: mp 118° C.; ¹H NMR (400 MHz, CDCl₃) δ2.14 (3H, s), 4.65 (2H, dd, J = 0.8, 6.0 Hz), 7.14 (1H, dd, J = 2.8, 8.8 Hz), 7.34 (1H, brt, J = 6.0 Hz), 7.40 (1H, d, J = 2.8 Hz), 7.46 (1H, t, J = 0.8 Hz), 7.59 (1H, d, J = 8.8 Hz), 7.69 (1H, brs).
333: mp 152–154° C.; ¹H NMR (400 MHz, CDCl₃) δ2.14 (3H, s), 4.66 (2H, d, J = 6.4 Hz), 7.21–7.26 (2H, m), 7.34 (1H, s), 7.39–7.44 (2H, m), 7.47 (1H, s), 7.64 (1H, s).
334: mp 144° C.; ¹H NMR (400 MHz, CDCl₃) δ2.18 (3H, s), 4.67 (2H, dd, J = 0.8, 6.0 Hz), 7.30–7.38 (2H, m), 7.47 (1H, s), 7.49 (1H, d, J = 0.8 Hz), 7.75 (1H, s), 7.78 (1H, d, J = 5.6 Hz).
335: mp 161° C.; ¹H NMR (400 MHz, CDCl₃) δ2.13 (3H, s), 4.64 (2H, dd, J = 0.8, 6.4 Hz), 7.09 (2H, d, J = 9.2 Hz), 7.17 (2H, d, J = 9.2 Hz), 7.35 (1H, brt, J = 6.4 Hz), 7.45 (1H, s), 7.52 (1H, s).
336: mp 151° C.; ¹H NMR (400 MHz, CDCl₃) δ2.26 (3H, s), 3.30 (3H, s), 4.65 (2H, dd), 6.76 (1H, d), 6.78 (1H, d), 7.47 (1H, s), 7.50 (1H, dd), 7.56 (1H, brt).
337: mp 141–142° C.; ¹H NMR (400 MHz, CDCl₃) δ2.28 (3H, s), 3.28 (3H, s), 4.66(2H, dd, J = 6.0, 0.8 Hz), 6.54 (2H, d, J = 11.6 Hz), 7.47 (1H, s), 7.55 (1H, brt, J = 6.0 Hz).
338: mp 143° C.; ¹H NMR (400 MHz, CDCl₃) δ2.23 (3H, s), 3.33 (3H, s), 4.64 (2H, d), 7.04 (2H, d), 7.45 (1H, s), 7.55 (2H, d), 7.62 (1H, brt).
339: mp 77° C. (E:Z = 2.8:1); ¹H NMR (400 MHz, CDCl₃) δ(E isomer) 2.24 (3H, s), 3.17 (3H, s), 3.24 (3H, s), 4.70 (2H, s), 6.51 (2H, d, J = 12.0 Hz), 7.50 (1H, s); (Z) 2.26 (3H, s), 3.03 (3H, s), 3.24 (3H, s), 4.82 (2H, s), 6.45 (2H, d, J = 12.0 Hz), 7.46 (1H, s).
340: ¹H NMR (400 MHz, CDCl₃) δ1.23 (6H, d), 1.79 (3H, s), 3.96 (1H, septet), 4.66 (2H, dd), 6.59 (1H, d), 6.12 (1H, d), 7.47 (1H, s), 7.48 (1H, dd), 7.62 (1H, brt).
341: ¹H NMR (400 MHz, CDCl₃) δ1.23 (6H, d), 1.67 (3H, s), 3.88 (1H, septet), 4.64 (2H, d), 6.92 (2H, d), 7.47 (1H, s), 7.53 (2H, d), 7.62 (1H, brt).
342: mp 213–215° C.; ¹H NMR (400 MHz, DMSO-d₆) δ4.55 (2H, d), 7.61 (1H, s), 7.72 (2H, d), 7.82 (2H, d), 9.15 (1H, brt).
343: mp 169–170° C.; ¹H NMR (400 MHz, CDCl₃) δ2.94 (3H, d), 4.63 (2H, d), 5.06 (1H, brs), 7.05 (2H, d), 7.17 (1H, s), 7.46–7.52 (4H, m).
344: mp 180–181° C.; ¹H NMR (400 MHz, CDCl₃) δ2.13 (3H, s), 4.55 (2H, d, J=6.4 Hz), 7.04 (2H, d, J=8.8 Hz), 7.26 (2H, d, J=8.8 Hz), 7.39 (1H, brt, J=6.4), 7.51 (1H, brs), 7.78 (1H, d, J=2.4 Hz), 8.28 (1H, d, J=2.4 Hz).
345: mp 154–155° C.; ¹H NMR (400 MHz, CDCl₃) δ2.15 (3H, s), 4.57 (2H, d, J=6.4 Hz), 7.23 (1H, dd, J=8.0, 8.0 Hz), 7.26 (1H, d, J=8.0 Hz), 7.35 (1H, s), 7.40 (1H, d, J=8.0 Hz), 7.42 (1H, brt, J=6.4 Hz), 7.63 (1H, s), 7.80 (1H, d, J=2.4 Hz), 8.29 (1H, d, J=2.4 Hz).
346: mp 151° C.; ¹H NMR (400 MHz, CDCl₃) δ2.19 (3H, s), 4.58 (2H, d, J=6.4 Hz), 7.33 (1H, d, J=8.4 Hz), 7.38 (1H, brt, J=6.4 Hz), 7.50 (1H, brs), 7.76 (1H, d, J=8.4 Hz), 7.80 (1H, d, J=2.0 Hz), 7.81 (1H, s), 8.29 (1H, d, J=2.0 Hz).
347: mp 176–178° C.; ¹H NMR (400 MHz, CDCl₃) δ2.12 (3H, s), 4.64 (2H, d, J=6.4 Hz), 7.03 (2H, d, J=8.8 Hz), 7.26 (2H, d, J=8.8 Hz), 7.36 (1H, brt, J=6.4 Hz), 7.45 (1H, s), 7.50(1H, brs).

Hereinafter, formulation example and test examples of the pesticides according to the present invention will be described. In the meanwhile, Compound No. indicated in each of the tests corresponds to Compound No. in Tables 1 to 8.

FORMULATION EXAMPLE 1

Wettable Powder

A wettable powder containing 20% by weight of an active ingredient was prepared by homogeneously mixing and milling 20 parts by weight of a compound of the present invention, 20 parts by weight of Carplex #80 (white carbon, Shionogi & Co., Ltd., trade name), 52 parts by weight of ST Kaolincray (kaolinite, Tsuchiya Kaolin Co., Ltd., trade name), 5 parts by weight of Sorpol 9047K (anionic surfactant, Toho Chemical Industry Co., Ltd., trade name), and 3 parts by weight of Lenox P65L (an anionic surfactant, Toho Chemical Industry Co., Ltd., trade name).

FORMULATION EXAMPLE 2

Dust

A dust containing 2% by weight of an active ingredient was prepared by homogeneously mixing and milling 2 parts by weight of a compound of the present invention, 93 parts by weight of cray (manufactured by Nippon Talc Co., Ltd.), and 5 parts by weight of Carplex #80 (white carbon, Shionogi & Co., Ltd., trade name).

FORMULATION EXAMPLE 3

Emulsifiable Concentrate

A emulsifiable concentrate containing 20% by weight of an active ingredient was prepared by dissolving 20 parts by weight of a compound of the present invention in a mixed solvent of 35 parts by weight of xylene and 30 parts by weight of dimethylformamide, and adding 15 parts by weight of Sorpol 3005X (mixture of nonionic surfactant and anionic surfactant, Toho Chemical Industry Co., Ltd., trade name).

FORMULATION EXAMPLE 4

Flowable Agent

A flowable agent containing 20% by weight of an active ingredient was prepared by wet-milling 30 parts by weight of a compound of the present invention with 5 parts by weight of Sorpol 9047K (ditto), 3 parts by weight of SorbonT-20 (nonionic surfactant, Toho Chemical Industry Co., Ltd., trade name), 8 parts by weight of ethylene glycol and 44 parts by weight of water by means of Dyno-Mill (manufactured by Shinmaru Enterprises Corporation) to obtain a slurry mixture, adding 10 parts by weight of 1% by weight aqueous solution of xanthane gum (natural polymer) to the slurry mixture, and fully mixing and milling.

TEST EXAMPLE 1

Insecticidal Effect Against Larvae of Cabbage Moth (*Plutella xylostera*)

A piece of cabbage leaf (diameter: 6 cm) was immersed for 1 minute in a water-diluted solution of the insecticide (wettable powder) of the present invention prepared according to the prescription of Formulation Example 1. After immersion, the cabbage was air-dried and placed in a plastic cup (inner diameter: 7 cm), and then inoculated with 5 larvae of cabbage moth in the third stage therein (1-concentration, 2-repetion). The cup was allowed to stand in a room thermostated at 25° C. Four days after the inoculation, dead or alive larvae or suffuring larvae were counted, and mortality (%) was calculated wherein a suffering larva was regarded as 0.5 dead larva. When compounds of Compound Nos. described below were subjected to the test, the mortality was 100% in a compound concentration of 500 ppm. In the meanwhile, the Compounds Nos. correspond to ones in Tables 1 to 8.

Compounds Nos. 1, 5, 7, 8, 9, 10, 11, 12, 13, 15, 16, 17, 18, 19, 20, 21, 22, 23, 24, 25, 26, 27, 28, 29, 30, 31, 32, 33, 34, 35, 38, 42, 43, 44, 45, 47, 49, 50, 51, 52, 53, 54, 55, 59, 60, 61, 62, 63, 64, 65, 66, 68, 69, 70, 71, 72, 73, 74, 75, 78, 79, 81, 82, 85, 87, 88, 89, 90, 91, 92, 93, 94, 95, 96, 97, 98, 99, 102, 104, 105, 106, 107, 108, 109, 110, 111, 112, 113, 114, 115, 116, 117, 118, 119, 120, 121, 122, 123, 124, 125, 126, 127, 128, 129, 130, 131, 132, 134, 136, 137, 139, 140, 141, 142, 143, 144, 145, 146, 147, 149, 150, 151, 152, 153, 155, 156, 157, 158, 159, 160, 162, 163, 164, 165, 166, 167, 168, 170, 171, 172, 173, 175, 177, 181, 182, 184, 185, 191, 192, 194, 195, 196, 197, 199, 200, 201, 202, 203, 204, 205, 206, 207, 208, 209, 210, 211, 212, 214, 215, 216, 217, 218, 219, 220, 221, 225, 226, 227, 230, 232, 233, 234, 235, 236, 237, 238, 239, 240, 241, 242, 243, 245, 246, 247, 248, 249, 250, 251, 252, 254, 255, 256, 257, 258, 259, 260, 262, 263, 264, 265, 266, 267, 269, 270, 272, 275, 276, 284, 285, 286, 287, 288, 289, 290, 291, 292, 293, 294, 295, 296, 297, 298, 299, 300, 301, 302, 304, 305, 306, 307, 308, 309, 318, 319, 320, 321, 322, 323, 324, 325, 326, 328, 329, 330, 331, 332, 333, 334, 335, 336, 337, 338, 339, 340, 341, 342, 343, 344, 345, 346 and 347.

TEST EXAMPLE 2

Insecticidal Effect Against Larvae of Common Cutworm (*Spodoptera litura*)

A piece of cabbage leaf (diameter: 6 cm) was immersed for 1 minute in a water-diluted solution of the insecticide (wettable powder),of the present invention prepared according to the prescription of Formulation Example 1. After immersion, the cabbage was air-dried and placed in a plastic cup (inner diameter: 7 cm), and then inoculated with 5 larvae of common cutworm in the third stage therein (1-concentration, 2-repetion). The cup was allowed to stand in a room thermostated at 25° C. Four days after the inoculation, dead or alive larvae or suffuring larvae were counted, and mortality (%) was calculated wherein a suffering larva was regarded as 0.5 dead larva. When compounds of Compound Nos. described below were subjected to the test, the mortality was 100% in a compound concentration of 500 ppm. In the meanwhile, the Compounds Nos. correspond to ones in Tables 1 to 8.

Compounds Nos. 6, 7, 8, 9, 11, 12, 13, 15, 16, 17, 19, 20, 21, 22, 23, 25, 26, 27, 28, 29, 30, 31, 32, 33, 34, 35, 38, 39, 42, 43, 44, 45, 47, 49. 50, 51, 52, 53, 54, 59, 60, 61, 62, 63, 64, 65, 69, 70, 71, 72, 73, 74, 75, 78, 79, 81, 82, 85, 87, 88, 89, 90, 91, 92, 94, 95, 96, 97, 98, 99, 104, 105, 106, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 143, 144, 145, 146, 147, 152, 153, 155, 157, 158, 159, 160, 161, 162, 165, 166, 167, 168, 171, 174, 175, 176, 177, 180, 182, 184, 185, 188, 189, 190, 191, 192, 194, 195, 196, 197, 199, 200, 201, 205, 206, 207, 208, 209, 210, 211, 212, 215, 216, 217, 219, 220, 221, 225, 226, 227, 230, 232, 235, 236, 237, 238, 239, 240, 241, 242, 243, 245, 246, 247, 248, 249, 250, 251, 255, 256, 257, 258, 259, 262, 263, 264, 265, 266, 267, 269, 270, 272, 275, 276, 284, 287, 288, 289, 290, 291, 292, 293, 294, 295, 296, 297, 298, 299, 300, 301, 302, 303, 304, 307, 308, 309, 318, 319, 320, 321, 322, 323, 324, 325, 326, 327, 328, 329, 330, 331, 332, 333, 334, 335, 336, 337, 338, 339, 340, 341, 342, 343, 344, 345, 346 and 347.

TEST EXAMPLE 3

Insecticidal Effect Against Larvae of Smaller Tea Tortrix (*Adoxophyes fasciata*)

A piece of artificial feed (diameter: ca. 5 cm; one eighth of a circle; thickness: 0.5 cm) was immersed for 10 seconds in a water-diluted solution of the insecticide (wettable powder) of the present invention prepared according to the prescription of Formulation Example 1. After immersion, the feed was placed in a plastic cup (inner diameter: 4 cm), and then inoculated with 5 larvae of smaller tea tortrix in the third stage therein (1-concentration, 2-repetion). The cup was allowed to stand in a room thermostated at 25° C. Four days after the inoculation, dead or alive larvae or suffering larvae were counted, and mortality (%) was calculated wherein a suffering larva was regarded as 0.5 dead larva. When compounds of Compound Nos. described below were subjected to the test, the mortality was 100% in a compound concentration of 500 ppm. In the meanwhile, the Compounds Nos. correspond to ones in Tables 1 to 8.

Compounds Nos. 8, 11, 12, 13, 16, 17, 20, 21, 22, 24, 26, 27, 28, 29, 30, 31, 34, 35, 37, 38, 39, 43, 44, 45, 47, 49, 52, 53, 54, 59, 60, 63, 64, 65, 68, 69, 71, 72, 73, 74, 75, 78, 79, 82, 85, 90, 91, 92, 93, 94, 95, 97, 99, 100, 104, 106, 107, 109, 110, 111, 113, 115, 117, 118, 119, 120, 121, 122, 123, 124, 125, 126, 127, 128, 129, 131, 134, 136, 137, 139, 144, 145, 146, 147, 152, 153, 155, 157, 159, 160, 162, 163, 166, 168, 171, 174, 175, 176, 177, 178, 182, 184, 185, 189, 190, 191, 192, 194, 195, 196, 197, 201, 207, 208, 209, 210, 211, 212, 215, 216, 217, 219, 220, 225, 226, 227, 230, 235, 236, 237, 238, 240, 241, 242, 243, 246, 247, 248, 249, 250, 251, 255, 256, 257, 258, 259, 262, 263, 264, 265, 266, 267, 270, 272, 275, 284, 287, 288, 289, 290, 292, 294, 295, 296, 297, 298, 299, 300, 302, 303, 304, 307, 309, 318, 320, 321, 322, 323, 324, 325, 326, 327, 328, 329, 330, 331, 332, 333, 334, 335, 336, 337, 338, 339, 340, 342, 343, 344, 345, 346 and 347.

INDUSTRIAL APPLICABILITY

The insecticides containing hydradine derivatives as active ingredient according to the present invention exert an extremely excellent control effect against pests such as arthropods (insects), nematodes, worms or protozoans in the agriculture and horticulture field, clothing, food and housing-related field, or livestock and pet field, in particular against harmful insects in the agriculture and horticulture field, and therefore the insecticides are useful as controller against these pests.

The invention claimed is:

1. An insecticide characterized by containing as active ingredient a hydrazone derivative of formula (I)

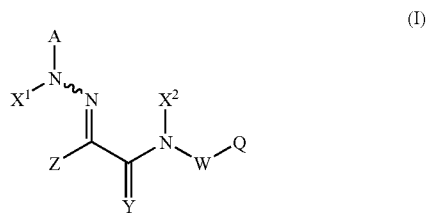

wherein A and Q independently of the other are an unsubstituted or substituted aryl, or an unsubstituted or substituted heterocyclic group, W is oxygen atom, an unsubstituted or substituted alkylene group, an unsubstituted or substituted oxyalkylene group, or an unsubstituted or substituted alkyleneoxy, $X^1$ and $X^2$ independently of the other are hydrogen atom, an unsubstituted or substituted alkyl, an unsubstituted or substituted alkenyl, an unsubstituted or substituted alkynyl, an unsubstituted or substituted aryl, an unsubstituted or substituted heterocyclic group, formyl, an unsubstituted or substituted acyl, an unsubstituted or substituted alkoxycarbonyl, an unsubstituted or substituted aryloxycarbonyl, an unsubstituted or substituted heterocyclic oxycarbonyl, an unsubstituted or substituted alkylsulfinyl, an unsubstituted or substituted arylsulfinyl, an unsubstituted or substituted heterocyclic sulfinyl, an unsubstituted or substituted alkylsulfonyl, an unsubstituted or substituted arylsulfonyl, or an unsubstituted or substituted heterocyclic sulfonyl, Y is oxygen atom, Z is hydrogen atom, a halogen atom, cyano, an unsubstituted or substituted alkyl, an unsubstituted or substituted alkenyl, an unsubstituted or substituted alkynyl, an unsubstituted or substituted amino, an unsubstituted or substituted alkoxy, or an unsubstituted or substituted alkylthio; and further comprising an insecticidal carrier, an insecticidal spreader, an insecticidal emulsifier, an insecticidal wetting agent, an insecticidal dispersing agent or an insecticidal disintegrator.

2. The insecticide according to claim 1, wherein A and Q independently of the other are an aryl or a heterocyclic group which is unsubstituted or substituted by a substituent selected from $G^1$ wherein $G^1$ is a halogen atom, hydroxy, cyano, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl, a haloalkylsulfonyl, an aryl, an aryloxy, an arylthio, a heterocyclic group, a heterocyclic oxy or a heterocyclic thio (the aryl, aryloxy, arylthio, heterocyclic group, heterocyclic oxy and heterocyclic thio may be further substituted by a substituent selected from the group consisting of a halogen atom, hydroxy, cyano, nitro, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl), in case where plurality of $G^1$s are present, adjacent two $G^1$s may form a fused ring together with Q or A, W is oxygen atom, —(C(R$^1$)(R$^2$))$_n$—, —O(C(R$^1$)(R$^2$))$_n$—, or —(C(R$^1$)(R$^2$))$_n$O— wherein n is an integer of 1 to 5, and R$^1$ and R$^2$ independently of the other are hydrogen atom, an alkyl, an alkenyl or alkynyl, or R$^1$ and R$^2$ together form an alkylidene group, $X^1$ and $X^2$ independently of the other are hydrogen atom, formyl, or an alkyl, an alkenyl, an alkynyl, an aryl, a heterocyclic group, an acyl, an alkoxycarbony, an aryloxycarbonyl, a heterocyclic oxycarbonyl, an alkylsulfinyl, an arylsulfinyl, a heterocyclic sulfinyl, an alkylsufonyl, an arylsulfonyl or a heterocyclic sulfonyl which is unsubstituted or substituted by a substituent selected from $G^2$ wherein $G^2$ a halogen atom, hydroxy, cyano, an alkyl, a haloalkyl, an alkenyl, a haloalkenyl, an alkynyl, a haloalkynyl, an alkoxy, a haloalkoxy, an alkoxyalkoxy, formyl, an acyl, an acyloxy, an alkoxycarbonyl, an alkylthio, a haloalkylthio, an alkylsulfinyl, a haloalkylsulfinyl, an alkylsulfonyl, a haloalkylsulfonyl, an aryl, an aryloxy, an arylthio, a heterocyclic group, a heterocyclic oxy or a heterocyclic thio (the aryl, aryloxy, arylthio, heterocyclic group, heterocyclic oxy and heterocyclic thio may be further substituted by a substituent selected from the group consisting of a halogen atom, hydroxy, cyano, an alkyl, a haloalkyl, an alkenyl, a haloalkenyl, an alkynyl, a haloalkynyl, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl), Z is hydrogen atom, a halogen atom, cyano, or an alkyl, an alkenyl, an alkynyl, an alkoxy or an alkylthio which is unsubstituted or substituted by a substituent selected from $G^3$ (wherein $G^3$ is a halogen atom, hydroxy, cyano, a haloalkyl, an alkenyl, a haloalkenyl, an alkynyl, a haloalkynyl, an alkoxy, a haloalkoxy, an alkylthio or a haloalkylthio), or an amino which is unsubstituted or substituted by a substituent selected from $G^4$ (wherein $G^4$ is hydroxy, cyano, an alkyl, a haloalkyl, an alkenyl, a haloalkenyl, an alkynyl, a haloalkynyl, an alkoxy or a haloalkoxy, in case where the amino is substituted by two substituents selected from $G^4$, the $G^4$s are same or different each other, and the $G^4$s optionally forms a ring).

3. The insecticide according to claim 1, wherein Q is an aryl or a heterocyclic group which is unsubstituted or substituted by a substituent selected from the group consisting of a halogen atom, an alkyl, a haloalkyl, an alkylamino, a dialkylamino, an alkoxy, a haloalkoxy, an alkylthio and a haloalkylthio.

4. The insecticide according to claim 1, wherein W is oxygen atom, —(C(R$^1$)(R$^2$))— (wherein R$^1$ and R$^2$ independently of the other are hydrogen atom, an alkyl, an alkenyl or alkynyl, or R$^1$ and R$^2$ together form an alkylidene group).

5. The insecticide according to claim 1, wherein $X^2$ is hydrogen atom, an alkyl or an alkoxycarbonyl.

6. The insecticide according to claim 1, wherein $X^1$ is hydrogen atom, an alkenyl having 1 to 4 carbon atoms, an acyl having 1 to 10 carbon atoms, or an alkyl having 1 to 10 carbon atoms which is unsubstituted or substituted by a substituent selected from the group consisting of a halogen atom, cyano, an alkoxy, an alkylthio, an alkoxycarbonyl and an unsubstituted or substituted aryl.

7. The insecticide according to claim 1, wherein Z is hydrogen atom, cyano, an amino unsubstituted or substituted by one or two alkyl groups having 1 to 4 carbon atoms, or an alkyl unsubstituted or substituted by a substituent selected from the group consisting of a halogen atom, an alkoxy and an alkylthio.

8. The insecticide according to claim 1, wherein A is phenyl or a nitrogen-containing heterocyclic group unsubstituted or substituted by a substituent selected from the group consisting of a halogen atom, cyano, nitro, an alkyl, a haloalkyl, an alkoxy, a haloalkoxy, an alkylthio and a haloalkylthio.

9. A hydrazone derivative of formula (II)

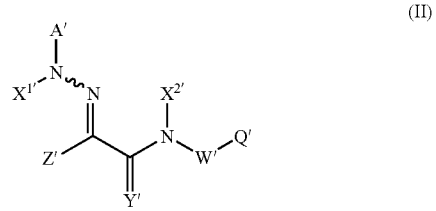

(II)

wherein A' and Q' independently of the other are an aryl or a heterocyclic group which is unsubstituted or substituted by a substituent selected from $G^5$ wherein $G^5$ is a halogen atom, hydroxy, cyano, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl, a haloalkylsulfonyl, an aryl, an aryloxy, an arylthio, a heterocyclic group, a heterocyclic oxy or a heterocyclic thio (the aryl, aryloxy, arylthio, heterocyclic group, heterocyclic oxy and heterocyclic thio may be further substituted by a substituent selected from the group consisting of a halogen atom, hydroxy, cyano, nitro, an alkyl, a haloalkyl, an alkenyl, a haloalkenyl, an alkynyl, a haloalkynyl, amino, an alkylamino, a dialkylamino, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl), W' is oxygen atom, —(C(R$^1$)(R$^2$))$_n$—, —O(C(R$^1$)(R$^2$))$_n$—, or —(C(R$^1$)(R$^2$))$_n$O— wherein n is an integer of 1 to 5, and R$^1$ and R$^2$ independently of the other are hydrogen atom, an alkyl, an alkenyl or alkynyl, or R$^1$ and R$^2$ together form an alkylidene group, $X^{1'}$ and $X^{2'}$ independently of the other are hydrogen atom, formyl, or an alkyl, an alkenyl, an alkynyl, an aryl, a heterocyclic group, an acyl, an alkoxycarbony, an aryloxycarbonyl, a heterocyclic oxycarbonyl, an alkylsulfinyl, an arylsulfinyl, a heterocyclic sulfinyl, an alkylsufonyl, an arylsulfonyl or a heterocyclic sulfonyl which is unsubstituted or substituted by a substituent selected from $G^2$ wherein $G^2$ is a halogen atom, hydroxy, cyano, an alkyl, a haloalkyl, an alkenyl, a haloalkenyl, an alkynyl, a haloalkynyl, an alkoxy, a haloalkoxy, an alkoxyalkoxy, formyl, an acyl, an acyloxy, an alkoxycarbonyl, an alkylthio, a haloalkylthio, an alkylsulfinyl, haloalkylsulfinyl, an alkylsulfonyl, a haloalkylsulfonyl, an aryl, an aryloxy, an arylthio, a heterocyclic group, a heterocyclic oxy or a heterocyclic thio (the aryl, aryloxy, arylthio, heterocyclic group, heterocyclic oxy and heterocyclic thio may be further substituted by a substituent selected from the group consisting of a halogen atom, hydroxy, cyano, an alkyl, a haloalkyl, an alkenyl, a haloalkenyl, an alkynyl, a haloalkynyl, an alkoxy, a haloalkoxy, formyl, an acyl, an acyloxy, an alkoxycarbonyl, an alkylthio, a haloalkylthio, an alkylsulfinyl, a haloalkylsulfinyl, an alkylsulfonyl and a haloalkylsulfonyl), Y' is oxygen atom, Z' is a linear or branched alkyl, a linear or branched alkenyl, or a linear or branched alkynyl which is unsubstituted or substituted by a substituent selected from $G^6$ wherein $G^6$ is a halogen atom, an alkoxy, a haloalkoxy, an alkylthio or a haloalkylthio.

10. The hydrazone derivative according to claim 9, wherein A' is is phenyl or a nitrogen-containing heterocyclic group unsubstituted or substituted by a substituent selected from the group consisting of a halogen atom, an alkyl, a haloalkyl, an alkoxy, a haloalkoxy, an alkylthio and a haloalkylthio.

11. The hydrazone derivative according to claim 10, wherein A' is is phenyl unsubstituted or substituted by a substituent selected from the group consisting of a halogen atom, an alkyl, a haloalkyl and a haloalkoxy.

12. The hydrazone derivative according to claim 9, wherein Q' is an aryl or a heterocyclic group unsubstituted or substituted by a substituent selected from the group consisting of a halogen atom, an alkyl, a haloalkyl, an alkylamino, a dialkylamino, an alkoxy, a haloalkoxy, an alkylthio and a haloalkylthio.

13. The hydrazone derivative according to claim 12, wherein Q' is a heterocyclic group unsubstituted or substituted by a substituent selected from the group consisting of a halogen atom, an alkyl and a haloalkyl.

14. The hydrazone derivative according to claim 9, wherein $X^{2'}$ is hydrogen atom, an alkyl or an alkoxycarbonyl.

15. The hydrazone derivative according to claim 9, wherein $X^{1'}$ is hydrogen atom, an alkenyl having 1 to 4 carbon atoms, an acyl having 1 to 10 carbon atoms, or an alkyl having 1 to 10 carbon atoms which is unsubstituted or substituted by a substituent selected from the group consisting of a halogen atom, cyano, an alkoxy, an alkylthio, an alkoxycarbonyl and an unsubstituted or substituted aryl.

16. The hydrazone derivative according to claim 9, wherein W' is oxygen atom, —C($R^1$)($R^2$)— (wherein $R^1$ and $R^2$ independently of the other are hydrogen atom, an alkyl, an alkenyl or alkynyl, or $R^1$ and $R^2$ together form an alkylidene group).

17. The hydrazone derivative according to claim 9, wherein Z' is a linear or branched alkyl unsubstituted or substituted by a substituent selected from the group consisting of a halogen atom, an alkoxy and an alkylthio.

* * * * *